(12) United States Patent
Crotty et al.

(10) Patent No.: US 7,393,533 B1
(45) Date of Patent: Jul. 1, 2008

(54) H3L ENVELOPE PROTEIN IMMUNIZATION METHODS AND H3L ENVELOPE PASSIVE PROTECTION METHODS

(75) Inventors: Shane Crotty, San Diego, CA (US); Philip L Felgner, Rancho Santa Fe, CA (US); David Huw Davies, Long Beach, CA (US)

(73) Assignee: La Jolla Institute for Allergy and Immunology, La Jolla, CA (US)

( * ) Notice: Subject to any disclaimer, the term of this patent is extended or adjusted under 35 U.S.C. 154(b) by 0 days.

(21) Appl. No.: 11/269,054

(22) Filed: Nov. 8, 2005

Related U.S. Application Data

(60) Provisional application No. 60/701,738, filed on Jul. 21, 2005, provisional application No. 60/626,352, filed on Nov. 8, 2004.

(51) Int. Cl.
*A61K 39/395* (2006.01)
*A61K 39/42* (2006.01)
*A61K 39/38* (2006.01)
*A61K 39/275* (2006.01)
*A61K 39/00* (2006.01)

(52) U.S. Cl. .............. 424/147.1; 424/130.1; 424/141.1; 424/232.1; 424/184.1

(58) Field of Classification Search .................. None
See application file for complete search history.

(56) References Cited

U.S. PATENT DOCUMENTS

| | | | |
|---|---|---|---|
| 6,451,309 B2 * | 9/2002 | Hooper et al. | 424/147.1 |
| 6,620,412 B2 * | 9/2003 | Hooper et al. | 424/147.1 |
| 2006/0062800 A1 * | 3/2006 | Cohen et al. | 424/186.1 |

FOREIGN PATENT DOCUMENTS

WO   03/068151 A2   8/2003

OTHER PUBLICATIONS

Patt H. and Feigin R., Diagnosis and Management of Suspected Cases of Bioterrorism: A Pediatric Perspective, 2002, Pediatrics, vol. 109, No. 4, pp. 685-692.*
Aldaz-Carroll et al., Epitiope-Mapping Studies Define Two Major Neutralization Sites on the Vaccinia Virus Extracellular Enveloped Virus Glycoprotein B5R, 2005, Journal of Virology, vol. 79, No. 10, pp. 6260-6271.*
Boulanger, D., et al., Identification and Characterization of Three Immunodominant Structural Proteins of Fowlpox Virus, J. of Virology, 76(19):9844-9855 (2002).
da Fonseca, F.G., et al., Characterization of the Vaccinia Virus H3L Envelope Protein: Topology and Posttranslational Membrane Insertion via the C-Terminal Hydrophobic Tail, J. of Virology, 74(16):7508-7517 (2000).
da Fonseca, F.G., et al., Effects of Deletion or Stringent Repression to the H3L Envelope Gene on Vaccinia Virus Replication, J. of Virology, 74(16):7518-7528 (2000).
Pedersen, K., et al., Characterization of Vaccinia Virus Intracellular Cores: Implications for Viral Uncoating and Core Structure, J. of Virology, 74(8):3525-3536 (2000).

* cited by examiner

*Primary Examiner*—Bruce Campell
*Assistant Examiner*—Benjamin P Blumel
(74) *Attorney, Agent, or Firm*—Pillsbury Winthrop Shaw Pittman LLP

(57) ABSTRACT

The invention relates to, among other things, methods of protecting against poxvirus infection or pathogenesis and including pox viruses such as small pox (variola major and variola minor), cowpox, monkey pox vaccinia virus, and Molluscum Contagiosum using compositions such as human, humanized and chimeric antibodies that specifically bind to H3L protein.

69 Claims, 7 Drawing Sheets

Figure 3 (con't)
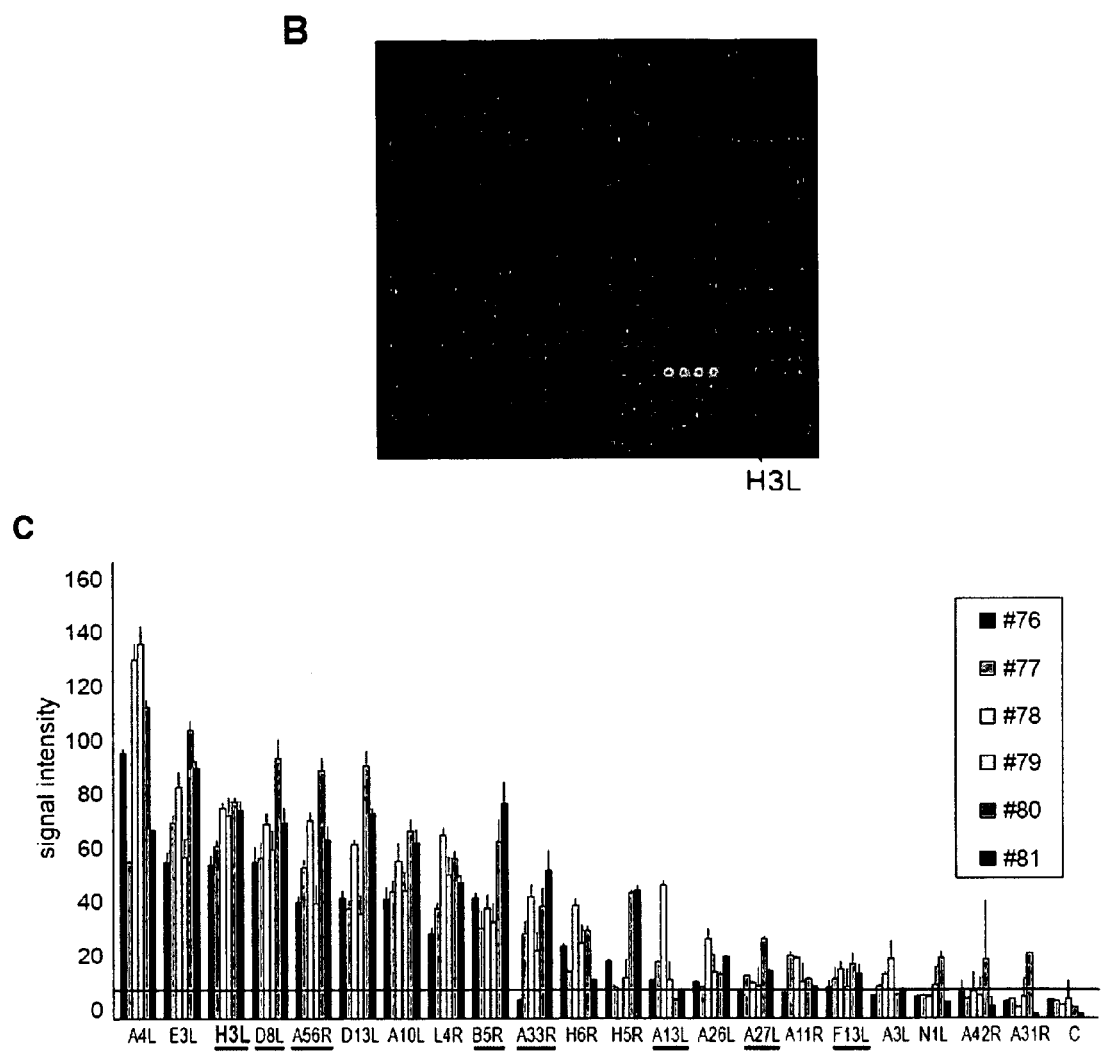

Figure 3 (con't)
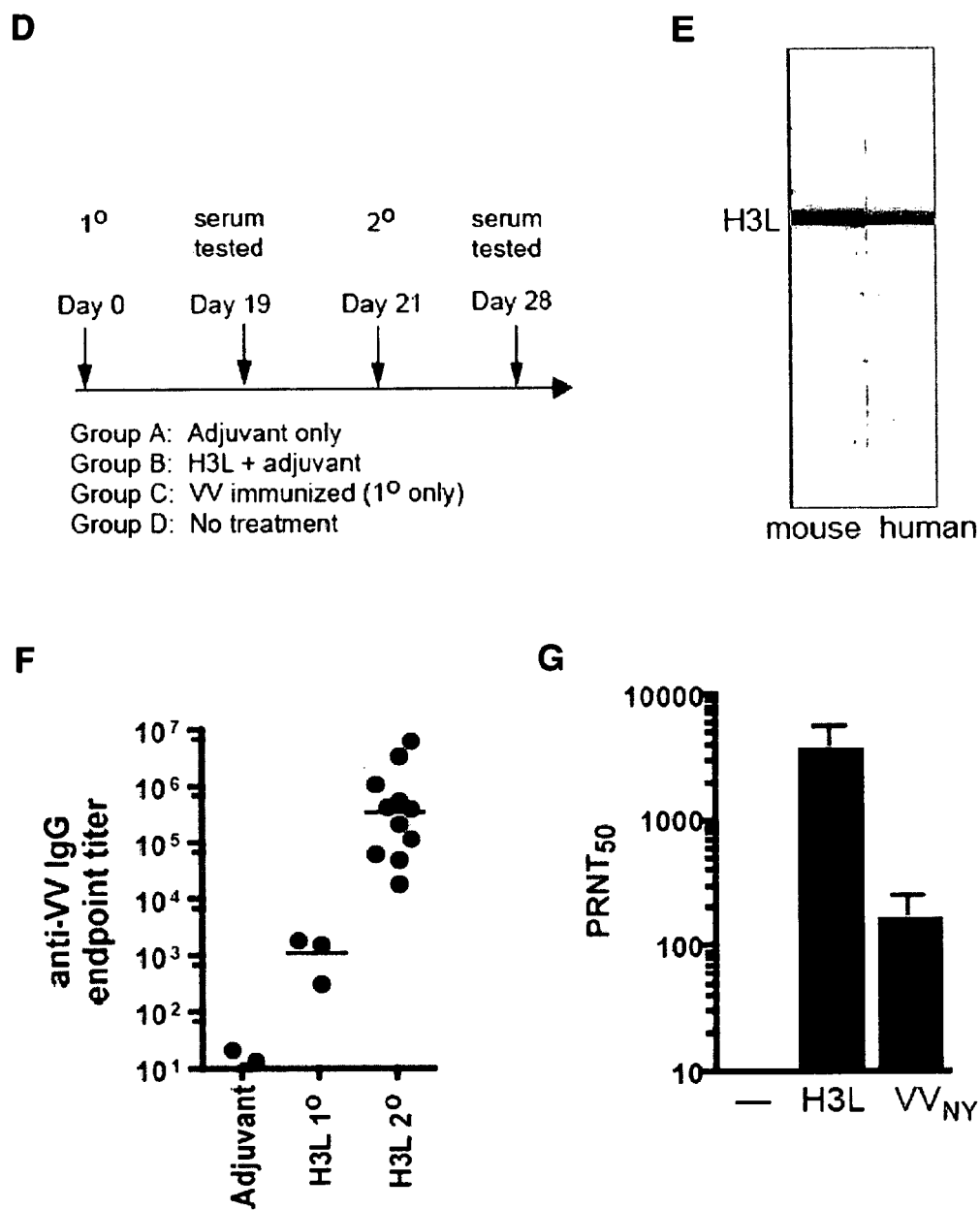

SEQUENCE LISTING

<160> NUMBER OF SEQ ID NOS: 13

<210> SEQ ID NO 1
<211> LENGTH: 324
<212> TYPE: PRT
<213> ORGANISM: Vaccinia virus copenhagen strain

<400> SEQUENCE: 1

```
Met Ala Ala Val Lys Thr Pro Val Ile Val Pro Val Ile Asp Arg
1               5                   10                  15

Pro Pro Ser Glu Thr Phe Pro Asn Val His Glu His Ile Asn Asp Gln
                20                  25                  30

Lys Phe Asp Asp Val Lys Asp Asn Glu Val Met Pro Glu Lys Arg Asn
            35                  40                  45

Val Val Val Lys Asp Asp Pro Asp His Tyr Lys Asp Tyr Ala Phe
        50                  55                  60

Ile Gln Trp Thr Gly Gly Asn Ile Arg Asn Asp Asp Lys Tyr Thr His
65                  70                  75                  80

Phe Phe Ser Gly Phe Cys Asn Thr Met Cys Thr Glu Glu Thr Lys Arg
                85                  90                  95

Asn Ile Ala Arg His Leu Ala Leu Trp Asp Ser Asn Phe Phe Thr Glu
                100                 105                 110

Leu Glu Asn Lys Lys Val Glu Tyr Val Val Ile Val Glu Asn Asp Asn
                115                 120                 125

Val Ile Glu Asp Ile Thr Phe Leu Arg Pro Val Leu Lys Ala Met His
            130                 135                 140

Asp Lys Lys Ile Asp Ile Leu Gln Met Arg Glu Ile Ile Thr Gly Asn
145                 150                 155                 160

Lys Val Lys Thr Glu Leu Val Met Asp Lys Asn His Thr Ile Phe Thr
                165                 170                 175

Tyr Thr Gly Gly Tyr Asp Val Ser Leu Ser Ala Tyr Ile Ile Arg Val
                180                 185                 190

Thr Thr Ala Leu Asn Ile Val Asp Glu Ile Ile Lys Ser Gly Gly Leu
            195                 200                 205

Ser Ser Gly Phe Tyr Phe Glu Ile Ala Arg Ile Glu Asn Glu Met Lys
210                 215                 220

Ile Asn Arg Gln Ile Leu Asp Asn Ala Ala Lys Tyr Val Glu His Asp
225                 230                 235                 240

Pro Arg Leu Val Ala Glu His Arg Phe Glu Asn Met Lys Pro Asn Phe
                245                 250                 255

Trp Ser Arg Ile Gly Thr Ala Ala Lys Arg Tyr Pro Gly Val Met
                260                 265                 270

Tyr Ala Phe Thr Thr Pro Leu Ile Ser Phe Phe Gly Leu Phe Asp Ile
            275                 280                 285

Asn Val Ile Gly Leu Ile Val Ile Leu Phe Ile Met Phe Met Leu Ile
        290                 295                 300

Phe Asn Val Lys Ser Lys Leu Leu Trp Phe Leu Thr Gly Thr Phe Val
305                 310                 315                 320

Thr Ala Phe Ile
```

<210> SEQ ID NO 2
<211> LENGTH: 324
<212> TYPE: PRT
<213> ORGANISM: Vaccinia virus western reserve strain

<400> SEQUENCE: 2

Met Ala Ala Lys Thr Pro Val Ile Val Pro Val Ile Asp Arg
1               5                   10                  15

Leu Pro Ser Glu Thr Phe Pro Asn Val His Glu His Ile Asn Asp Gln
                20                  25                  30

Lys Phe Asp Asp Val Lys Asp Asn Glu Val Met Pro Glu Lys Arg Asn
            35                  40                  45

Val Val Val Lys Asp Asp Pro Asp His Tyr Lys Asp Tyr Ala Phe
    50                  55                  60

Ile Gln Trp Thr Gly Gly Asn Ile Arg Asn Asp Asp Lys Tyr Thr His
65                  70                  75                  80

Phe Phe Ser Gly Phe Cys Asn Thr Met Cys Thr Glu Glu Thr Lys Arg
                85                  90                  95

Asn Ile Ala Arg His Leu Ala Leu Trp Asp Ser Asn Phe Phe Thr Glu
                100                 105                 110

Leu Glu Asn Lys Lys Val Glu Tyr Val Val Ile Val Glu Asn Asp Asn
                115                 120                 125

Val Ile Glu Asp Ile Thr Phe Leu Arg Pro Val Leu Lys Ala Met His
    130                 135                 140

Asp Lys Lys Ile Asp Ile Leu Gln Met Arg Glu Ile Ile Thr Gly Asn
145                 150                 155                 160

Lys Val Lys Thr Glu Leu Val Met Asp Lys Asn His Ala Ile Phe Thr
                165                 170                 175

Tyr Thr Gly Gly Tyr Asp Val Ser Leu Ser Ala Tyr Ile Ile Arg Val
                180                 185                 190

Thr Thr Ala Leu Asn Ile Val Asp Glu Ile Ile Lys Ser Gly Gly Leu
            195                 200                 205

Ser Ser Gly Phe Tyr Phe Glu Ile Ala Arg Ile Glu Asn Glu Met Lys
    210                 215                 220

Ile Asn Arg Gln Ile Leu Asp Asn Ala Ala Lys Tyr Val Glu His Asp
225                 230                 235                 240

Pro Arg Leu Val Ala Glu His Arg Phe Glu Asn Met Lys Pro Asn Phe
                245                 250                 255

Trp Ser Arg Ile Gly Thr Ala Thr Lys Arg Tyr Pro Gly Val Met
                260                 265                 270

Tyr Ala Phe Thr Thr Pro Leu Ile Ser Phe Phe Gly Leu Phe Asp Ile
            275                 280                 285

Asn Val Ile Gly Leu Ile Val Ile Leu Phe Ile Met Phe Met Leu Ile
    290                 295                 300

Phe Asn Val Lys Ser Lys Leu Leu Trp Phe Leu Thr Gly Thr Phe Val
305                 310                 315                 320

Thr Ala Phe Ile

<210> SEQ ID NO 3
<211> LENGTH: 324
<212> TYPE: PRT
<213> ORGANISM: Vaccinia virus MVA strain

<400> SEQUENCE: 3

Met Ala Ala Val Lys Thr Pro Val Ile Val Pro Val Ile Asp Arg
1               5                   10                  15

Pro Pro Ser Glu Thr Phe Pro Asn Val His Glu His Ile Asn Asp Gln
                20                  25                  30

```
Lys Phe Asp Asp Val Lys Asp Asn Glu Val Met Pro Glu Lys Arg Asn
            35                  40                  45

Val Val Val Val Lys Asp Asp Pro Asp His Tyr Lys Asp Tyr Ala Phe
    50                  55                  60

Ile Gln Trp Thr Gly Gly Asn Ile Arg Asn Asp Asp Lys Tyr Thr His
65                  70                  75                  80

Phe Phe Ser Gly Phe Cys Asn Thr Met Cys Thr Glu Glu Thr Lys Arg
                85                  90                  95

Asn Ile Ala Arg His Leu Ala Leu Trp Asp Ser Asn Phe Phe Thr Glu
            100                 105                 110

Leu Glu Asn Lys Lys Val Glu Tyr Val Val Ile Val Glu Asn Asp Asn
            115                 120                 125

Val Ile Glu Asp Ile Thr Phe Leu Arg Pro Val Leu Lys Ala Met His
    130                 135                 140

Asp Lys Lys Ile Asp Ile Leu Gln Met Arg Glu Ile Ile Thr Gly Asn
145                 150                 155                 160

Lys Val Lys Thr Glu Leu Val Met Asp Lys Asn His Ala Ile Phe Thr
                165                 170                 175

Tyr Thr Gly Gly Tyr Asp Val Ser Leu Ser Ala Tyr Ile Ile Arg Val
            180                 185                 190

Thr Thr Ala Leu Asn Ile Val Asp Glu Ile Ile Lys Ser Gly Gly Leu
    195                 200                 205

Ser Ser Gly Phe Tyr Phe Glu Ile Ala Arg Ile Glu Asn Glu Met Lys
210                 215                 220

Ile Asn Arg Gln Ile Leu Asp Asn Ala Ala Lys Tyr Val Glu His Asp
225                 230                 235                 240

Pro Arg Leu Val Ala Glu Tyr Arg Phe Glu Asn Met Lys Pro Asn Phe
                245                 250                 255

Trp Ser Arg Ile Gly Thr Ala Ala Ala Lys Arg Tyr Pro Gly Val Met
            260                 265                 270

Tyr Ala Phe Thr Thr Pro Leu Ile Ser Phe Phe Gly Leu Phe Asp Ile
    275                 280                 285

Asn Val Ile Gly Leu Ile Val Ile Leu Phe Ile Met Phe Met Leu Ile
290                 295                 300

Phe Asn Val Lys Ser Lys Leu Leu Trp Phe Leu Thr Gly Thr Phe Val
305                 310                 315                 320

Thr Ala Phe Ile

<210> SEQ ID NO 4
<211> LENGTH: 324
<212> TYPE: PRT
<213> ORGANISM: Vaccinia virus Acambis MVA strain

<400> SEQUENCE: 4

Met Ala Ala Val Lys Thr Pro Val Ile Val Pro Val Ile Asp Arg
1               5                   10                  15

Pro Pro Ser Glu Thr Phe Pro Asn Val His Glu His Ile Asn Asp Gln
            20                  25                  30

Lys Phe Asp Asp Val Lys Asp Asn Glu Val Met Pro Glu Lys Arg Asn
            35                  40                  45

Val Val Val Val Lys Asp Asp Pro Asp His Tyr Lys Asp Tyr Ala Phe
    50                  55                  60

Ile Gln Trp Thr Gly Gly Asn Ile Arg Asn Asp Asp Lys Tyr Thr His
65                  70                  75                  80
```

-continued

```
Phe Phe Ser Gly Phe Cys Asn Thr Met Cys Thr Glu Glu Thr Lys Arg
                85

```
Val Ile Glu Asp Ile Thr Phe Leu Arg Pro Val Leu Lys Ala Met His
    130                 135                 140

Asp Lys Lys Ile Asp Ile Leu Gln Met Arg Glu Ile Ile Thr Gly Asn
145                 150                 155                 160

Lys Val Lys Thr Glu Leu Val Met Asp Lys Asn His Ala Ile Phe Thr
                165                 170                 175

Tyr Thr Gly Gly Tyr Asp Val Ser Leu Ser Ala Tyr Ile Ile Arg Val
            180                 185                 190

Thr Thr Glu Leu Asn Ile Val Asp Glu Ile Ile Lys Ser Gly Gly Leu
        195                 200                 205

Ser Ser Gly Phe Tyr Phe Glu Ile Ala Arg Ile Glu Asn Glu Met Lys
    210                 215                 220

Ile Asn Arg Gln Ile Leu Asp Asn Ala Ala Lys Tyr Val Glu His Asp
225                 230                 235                 240

Pro Arg Leu Val Ala Glu His Arg Phe Glu Asn Met Lys Pro Asn Phe
                245                 250                 255

Trp Ser Arg Ile Gly Thr Ala Ala Thr Lys Arg Tyr Pro Gly Val Met
            260                 265                 270

Tyr Ala Phe Thr Thr Pro Leu Ile Ser Phe Phe Gly Leu Phe Asp Ile
        275                 280                 285

Asn Val Ile Gly Leu Ile Val Ile Leu Phe Ile Met Phe Met Leu Ile
    290                 295                 300

Phe Asn Val Lys Ser Lys Leu Leu Trp Phe Leu Thr Gly Thr Phe Val
305                 310                 315                 320

Thr Ala Phe Ile

<210> SEQ ID NO 6
<211> LENGTH: 324
<212> TYPE: PRT
<213> ORGANISM: Camelpox J3L vaccinia virus

<400> SEQUENCE: 6

Met Ala Ala Ala Lys Thr Pro Val Ile Val Pro Val Ile Asp Arg
1               5                   10                  15

Pro Pro Ser Glu Thr Phe Pro Asn Val His Glu His Ile Asn Asp Gln
                20                  25                  30

Lys Phe Asp Asp Val Lys Asp Asn Glu Val Met Pro Glu Lys Arg Asp
            35                  40                  45

Val Val Val Lys Asp Pro Asp His Tyr Lys Asp Tyr Ala Phe
        50                  55                  60

Ile Gln Trp Thr Gly Gly Asn Ile Arg Asn Asp Asp Lys Tyr Thr His
65                  70                  75                  80

Phe Phe Ser Gly Phe Cys Asn Thr Met Cys Thr Glu Thr Lys Arg
                85                  90                  95

Asn Ile Ala Arg His Leu Ala Leu Trp Asp Ser Lys Phe Phe Thr Glu
            100                 105                 110

Leu Glu Asn Lys Lys Val Glu Tyr Val Val Ile Val Glu Asn Asp Asn
        115                 120                 125

Val Ile Glu Asp Ile Thr Phe Leu Arg Pro Val Leu Lys Ala Met His
    130                 135                 140

Asp Lys Lys Ile Asp Ile Leu Gln Met Arg Glu Ile Ile Thr Gly Asn
145                 150                 155                 160

Lys Val Lys Thr Glu Leu Val Met Asp Lys Asp His Ala Ile Phe Thr
                165                 170                 175
```

```
Tyr Thr Gly Gly Tyr Asp Val Ser Leu Ser Ala Tyr Ile Ile Arg Val
            180                 185                 190

Thr Thr Ala Leu Asn Ile Val Asp Glu Ile Ile Lys Ser Gly Gly Leu
            195                 200                 205

Ser Ser Gly Phe Tyr Phe Glu Ile Ala Arg Ile Glu Asn Glu Met Lys
            210                 215                 220

Ile Asn Arg Gln Ile Leu Asp Asn Ala Ala Lys Tyr Val Glu His Asp
225                 230                 235                 240

Pro Arg Leu Val Ala Glu His Arg Phe Glu Asn Met Lys Pro Asn Phe
                245                 250                 255

Trp Ser Arg Ile Gly Thr Ala Ala Lys Arg Tyr Pro Gly Val Met
                260                 265                 270

Tyr Ala Phe Thr Thr Pro Leu Ile Ser Phe Pro Gly Leu Phe Asp Ile
            275                 280                 285

Asn Val Ile Gly Leu Ile Val Ile Leu Phe Ile Met Phe Met Leu Ile
            290                 295                 300

Phe Asn Val Lys Ser Lys Leu Leu Trp Phe Leu Thr Gly Thr Phe Val
305                 310                 315                 320

Thr Ala Phe Ile

<210> SEQ ID NO 7
<211> LENGTH: 325
<212> TYPE: PRT
<213> ORGANISM: Variola major virus (Bangladesh)

<400> SEQUENCE: 7

Met Ala Thr Val Asn Lys Thr Pro Val Ile Val Val Pro Val Ile Asp
1               5                   10                  15

Arg Pro Pro Ser Glu Thr Phe Pro Asn Leu His Glu His Ile Asn Asp
                20                  25                  30

Gln Lys Phe Asp Asp Val Lys Asp Asn Glu Val Met Pro Glu Lys Arg
            35                  40                  45

Asn Val Val Ile Val Lys Asp Asp Pro Asp His Tyr Lys Asp Tyr Ala
50                  55                  60

Phe Ile His Trp Thr Gly Gly Asn Ile Arg Asn Asp Asp Lys Tyr Thr
65                  70                  75                  80

His Phe Phe Ser Gly Phe Cys Asn Thr Met Cys Thr Glu Glu Thr Lys
                85                  90                  95

Arg Asn Ile Ala Arg His Leu Ala Leu Trp Asp Ser Lys Phe Phe Thr
            100                 105                 110

Glu Leu Glu Asn Lys Lys Val Glu Tyr Val Val Ile Val Glu Asn Asp
            115                 120                 125

Asn Val Ile Glu Asp Ile Thr Phe Leu Arg Pro Val Leu Lys Ala Met
130                 135                 140

His Asp Lys Lys Ile Asp Ile Leu Gln Met Arg Glu Ile Ile Thr Gly
145                 150                 155                 160

Asn Lys Val Lys Thr Glu Leu Val Met Asp Lys Asn His Val Ile Phe
                165                 170                 175

Thr Tyr Thr Gly Gly Tyr Asp Val Ser Leu Ser Ala Tyr Ile Ile Arg
            180                 185                 190

Val Thr Thr Ala Leu Asn Ile Val Asp Glu Ile Ile Lys Ser Gly Gly
            195                 200                 205

Leu Ser Ser Gly Phe Tyr Phe Glu Ile Ala Arg Ile Glu Asn Glu Met
            210                 215                 220
```

```
Lys Ile Asn Arg Gln Ile Met Asp Asn Ser Ala Lys Tyr Val Glu His
225                 230                 235                 240

Asp Pro Arg Leu Val Ala Glu His Arg Phe Glu Asn Met Lys Pro Asn
            245                 250                 255

Phe Trp Ser Arg Ile Gly Thr Ala Ala Val Lys Arg Tyr Pro Gly Val
        260                 265                 270

Met Tyr Ala Phe Thr Thr Pro Leu Ile Ser Phe Phe Gly Leu Phe Asp
    275                 280                 285

Ile Asn Val Ile Gly Leu Ile Val Ile Leu Phe Ile Met Phe Met Leu
        290                 295                 300

Ile Phe Asn Val Lys Ser Lys Leu Leu Trp Phe Leu Thr Gly Thr Phe
305                 310                 315                 320

Val Thr Ala Phe Ile
            325

<210> SEQ ID NO 8
<211> LENGTH: 325
<212> TYPE: PRT
<213> ORGANISM: Variola major virus (India)

<400> SEQUENCE: 8

Met Ala Thr Val Asn Lys Thr Pro Val Ile Val Val Pro Val Ile Asp
1               5                   10                  15

Arg Pro Pro Ser Glu Thr Phe Pro Asn Leu His Glu His Ile Asn Asp
            20                  25                  30

Gln Lys Phe Asp Asp Val Lys Asp Asn Glu Val Met Pro Glu Lys Arg
        35                  40                  45

Asn Val Val Ile Val Lys Asp Asp Pro Asp His Tyr Lys Asp Tyr Ala
    50                  55                  60

Phe Ile His Trp Thr Gly Gly Asn Ile Arg Asn Asp Asp Lys Tyr Thr
65                  70                  75                  80

His Phe Phe Ser Gly Phe Cys Asn Thr Met Cys Thr Glu Glu Thr Lys
                85                  90                  95

Arg Asn Ile Ala Arg His Leu Ala Leu Trp Asp Ser Lys Phe Phe Thr
            100                 105                 110

Glu Leu Glu Asn Lys Lys Val Glu Tyr Val Val Ile Val Glu Asn Asp
        115                 120                 125

Asn Val Ile Glu Asp Ile Thr Phe Leu Arg Pro Val Leu Lys Ala Met
    130                 135                 140

His Asp Lys Lys Ile Asp Ile Leu Gln Met Arg Glu Ile Ile Thr Gly
145                 150                 155                 160

Asn Lys Val Lys Thr Glu Leu Val Met Asp Lys Asn His Val Ile Phe
                165                 170                 175

Thr Tyr Thr Gly Gly Tyr Asp Val Ser Leu Ser Ala Tyr Ile Ile Arg
            180                 185                 190

Val Thr Thr Ala Leu Asn Ile Val Asp Glu Ile Ile Lys Ser Gly Gly
        195                 200                 205

Leu Ser Ser Gly Phe Tyr Phe Glu Ile Ala Arg Ile Glu Asn Glu Ile
    210                 215                 220

Lys Ile Asn Arg Gln Ile Met Asp Asn Ser Ala Lys Tyr Val Glu His
225                 230                 235                 240

Asp Pro Arg Leu Val Ala Glu His Arg Phe Glu Asn Met Lys Pro Asn
            245                 250                 255

Phe Trp Ser Arg Ile Gly Thr Ala Ala Val Lys Arg Tyr Pro Gly Val
        260                 265                 270
```

```
Met Tyr Ala Phe Thr Thr Pro Leu Ile Ser Phe Phe Gly Leu Phe Asp
        275                 280                 285

Ile Asn Val Ile Gly Leu Ile Val Ile Leu Phe Ile Met Phe Met Leu
        290                 295                 300

Ile Phe Asn Val Lys Ser Lys Leu Leu Trp Phe Leu Thr Gly Thr Phe
305                 310                 315                 320

Val Thr Ala Phe Ile
            325

<210> SEQ ID NO 9
<211> LENGTH: 325
<212> TYPE: PRT
<213> ORGANISM: Variola minor virus(Garcia)

<400> SEQUENCE: 9

Met Ala Ala Val Asn Lys Thr Pro Val Ile Val Val Pro Val Ile Asp
1               5                   10                  15

Arg Pro Pro Ser Glu Thr Phe Pro Asn Leu His Glu His Ile Asn Asp
            20                  25                  30

Gln Lys Phe Asp Asp Val Lys Asp Asn Glu Val Met Pro Glu Lys Arg
        35                  40                  45

Asn Val Val Ile Val Lys Asp Asp Pro Asp His Tyr Lys Asp Tyr Ala
    50                  55                  60

Phe Ile His Trp Thr Gly Gly Asn Ile Arg Asn Asp Asp Lys Tyr Thr
65                  70                  75                  80

His Phe Phe Ser Gly Phe Cys Asn Thr Met Cys Thr Glu Glu Thr Lys
                85                  90                  95

Arg Asn Ile Ala Arg His Leu Ala Leu Trp Asp Ser Lys Phe Phe Thr
            100                 105                 110

Glu Leu Glu Asn Lys Lys Val Glu Tyr Val Val Ile Val Glu Asn Asp
        115                 120                 125

Asn Val Ile Glu Asp Ile Thr Phe Leu Arg Pro Val Leu Lys Ala Met
    130                 135                 140

His Asp Lys Lys Ile Asp Ile Leu Gln Met Arg Glu Ile Ile Thr Gly
145                 150                 155                 160

Asn Lys Val Lys Thr Glu Leu Val Met Asp Lys Asn His Val Ile Phe
                165                 170                 175

Thr Tyr Thr Gly Gly Tyr Asp Val Ser Leu Ser Ala Tyr Ile Ile Arg
            180                 185                 190

Val Thr Thr Ala Leu Asn Ile Val Asp Glu Ile Ile Lys Ser Gly Gly
        195                 200                 205

Leu Ser Ser Gly Phe Tyr Phe Glu Ile Ala Arg Ile Glu Asn Glu Met
    210                 215                 220

Lys Ile Asn Arg Gln Ile Met Asp Asn Ser Ala Lys Tyr Val Glu His
225                 230                 235                 240

Asp Pro Arg Leu Val Ala Glu His Arg Phe Glu Asn Met Lys Pro Asn
                245                 250                 255

Phe Trp Ser Arg Ile Gly Thr Ala Ala Val Lys Arg Tyr Pro Gly Val
            260                 265                 270

Met Tyr Ala Phe Thr Thr Pro Leu Ile Ser Phe Phe Gly Leu Phe Asp
        275                 280                 285

Ile Asn Val Ile Gly Leu Ile Val Ile Leu Phe Ile Met Phe Met Leu
        290                 295                 300

Ile Phe Asn Val Lys Ser Lys Leu Leu Trp Phe Leu Thr Gly Thr Phe
```

```
                305                 310                 315                 320
Val Thr Ala Phe Ile
                325

<210> SEQ ID NO 10
<211> LENGTH: 325
<212> TYPE: PRT
<213> ORGANISM: Camelpox virus strain

<400> SEQUENCE: 10

Met Ala Ala Val Asn Arg Thr Pro Val Ile Val Pro Val Ile Asp
1               5                   10                  15

Arg His Pro Ser Glu Thr Phe Pro Asn Val His Glu His Ile Asn Asp
                20                  25                  30

Gln Lys Phe Asp Asp Val Lys Asp Asn Glu Val Met Pro Glu Lys Arg
            35                  40                  45

Asp Val Val Ile Val Lys Asp Asp Pro Asp His Tyr Lys Asp Tyr Ala
        50                  55                  60

Phe Ile Gln Trp Thr Gly Gly Asn Ile Arg Asn Asp Asp Lys Tyr Thr
65                  70                  75                  80

His Phe Phe Ser Gly Phe Cys Asn Thr Met Cys Thr Glu Glu Thr Lys
                85                  90                  95

Arg Asn Ile Ala Arg His Leu Ala Leu Trp Asp Ser Lys Phe Phe Thr
            100                 105                 110

Glu Leu Glu Asn Lys Lys Val Glu Tyr Val Val Ile Val Glu Asn Asp
        115                 120                 125

Asn Val Ile Glu Asp Ile Thr Phe Leu Arg Pro Val Leu Lys Ala Met
    130                 135                 140

His Asp Lys Lys Ile Asp Ile Leu Gln Met Arg Glu Ile Ile Thr Gly
145                 150                 155                 160

Asn Lys Val Lys Thr Glu Leu Val Met Asp Lys Asn Tyr Ala Ile Phe
                165                 170                 175

Thr Tyr Thr Gly Gly Tyr Asp Val Ser Leu Ser Ala Tyr Ile Ile Arg
            180                 185                 190

Val Thr Thr Ala Leu Asn Ile Val Asp Glu Ile Ile Lys Ser Gly Gly
        195                 200                 205

Leu Ser Ser Gly Phe Tyr Phe Glu Ile Ala Arg Ile Glu Asn Glu Met
    210                 215                 220

Lys Ile Asn Arg Gln Ile Met Asp Asn Ser Ala Lys Tyr Val Glu His
225                 230                 235                 240

Asp Pro Arg Leu Val Ala Glu His Arg Phe Glu Asn Met Lys Pro Asn
                245                 250                 255

Phe Trp Ser Arg Ile Gly Thr Ala Ala Lys Arg Tyr Pro Gly Val
            260                 265                 270

Met Tyr Ala Phe Thr Thr Pro Leu Ile Ser Phe Gly Leu Phe Asp
        275                 280                 285

Ile Asn Val Ile Gly Leu Ile Val Ile Leu Phe Ile Met Phe Met Leu
    290                 295                 300

Ile Phe Asn Val Lys Ser Lys Leu Leu Trp Phe Leu Thr Gly Thr Phe
305                 310                 315                 320

Val Thr Ala Phe Ile
                325

<210> SEQ ID NO 11
<211> LENGTH: 324
```

```
<212> TYPE: PRT
<213> ORGANISM: Monkeypox virus (Zaire-96-I-16)

<400> SEQUENCE: 11

Met Ala Ala Ala Lys Thr Pro Val Ile Val Pro Val Ile Asp Arg
1               5                   10                  15

Pro Pro Ser Glu Thr Phe Pro Asn Val His Glu His Ile Asn Asp Gln
                20                  25                  30

Lys Phe Asp Asp Val Lys Asp Asn Glu Val Met Gln Glu Lys Arg Asp
            35                  40                  45

Val Val Ile Val Asn Asp Asp Pro Asp His Tyr Lys Asp Tyr Val Phe
        50                  55                  60

Ile Gln Trp Thr Gly Gly Asn Ile Arg Asp Asp Asp Lys Tyr Thr His
65                  70                  75                  80

Phe Phe Ser Gly Phe Cys Asn Thr Met Cys Thr Glu Thr Lys Arg
                85                  90                  95

Asn Ile Ala Arg His Leu Ala Leu Trp Asp Ser Lys Phe Phe Ile Glu
            100                 105                 110

Leu Glu Asn Lys Asn Val Glu Tyr Val Val Ile Glu Asn Asp Asn
        115                 120                 125

Val Ile Glu Asp Ile Thr Phe Leu Arg Pro Val Leu Lys Ala Ile His
    130                 135                 140

Asp Lys Lys Ile Asp Ile Leu Gln Met Arg Glu Ile Ile Thr Gly Asn
145                 150                 155                 160

Lys Val Lys Thr Glu Leu Val Ile Asp Lys Asp His Ala Ile Phe Thr
                165                 170                 175

Tyr Thr Gly Gly Tyr Asp Val Ser Leu Ser Ala Tyr Ile Ile Arg Val
            180                 185                 190

Thr Thr Ala Leu Asn Ile Val Asp Glu Ile Ile Lys Ser Gly Gly Leu
        195                 200                 205

Ser Ser Gly Phe Tyr Phe Glu Ile Ala Arg Ile Glu Asn Glu Met Lys
    210                 215                 220

Ile Asn Arg Gln Ile Met Asp Asn Ser Ala Lys Tyr Val Glu His Asp
225                 230                 235                 240

Pro Arg Leu Val Ala Glu His Arg Phe Glu Thr Met Lys Pro Asn Phe
                245                 250                 255

Trp Ser Arg Ile Gly Thr Val Ala Ala Lys Arg Tyr Pro Gly Val Met
            260                 265                 270

Tyr Thr Phe Thr Thr Pro Leu Ile Ser Phe Phe Gly Leu Phe Asp Ile
        275                 280                 285

Asn Val Ile Gly Leu Ile Val Ile Leu Phe Ile Met Phe Met Leu Ile
    290                 295                 300

Phe Asn Val Lys Ser Lys Leu Leu Trp Phe Leu Thr Gly Thr Phe Val
305                 310                 315                 320

Thr Ala Phe Ile

<210> SEQ ID NO 12
<211> LENGTH: 324
<212> TYPE: PRT
<213> ORGANISM: Cowpox virus strain (GRI-90)

<400> SEQUENCE: 12

Met Ala Ala Ala Lys Thr Pro Val Ile Val Pro Val Ile Asp Arg
1               5                   10                  15

Pro Pro Ser Glu Thr Phe Pro Asn Val His Glu His Ile Asn Asp Gln
```

```
                20                  25                  30
Lys Phe Asp Asp Val Lys Asp Asn Glu Val Met Pro Glu Lys Arg Asp
             35                  40                  45
Val Val Val Val Lys Asp Asp Pro Asp His Tyr Lys Asp Tyr Ala Phe
         50                  55                  60
Ile Gln Trp Thr Gly Gly Asn Ile Arg Asn Asp Asp Lys Tyr Thr His
 65                  70                  75                  80
Phe Phe Ser Gly Phe Cys Asn Thr Met Cys Thr Glu Thr Lys Arg
                 85                  90                  95
Asn Ile Ala Arg His Leu Ala Leu Trp Asp Ser Lys Phe Phe Thr Glu
                100                 105                 110
Leu Glu Asn Lys Lys Val Glu Tyr Val Val Ile Val Glu Asn Asp Asn
                115                 120                 125
Val Ile Glu Asp Ile Thr Phe Leu Arg Pro Val Leu Lys Ala Met His
            130                 135                 140
Asp Lys Lys Ile Asp Ile Leu Gln Met Arg Glu Ile Ile Thr Gly Asn
145                 150                 155                 160
Lys Val Lys Thr Glu Leu Val Met Asp Lys Asp His Ala Ile Phe Thr
                165                 170                 175
Tyr Thr Gly Gly Tyr Asp Val Ser Leu Ser Ala Tyr Ile Ile Arg Val
                180                 185                 190
Thr Thr Ala Leu Asn Ile Val Asp Glu Ile Ile Lys Ser Gly Gly Leu
            195                 200                 205
Ser Ser Gly Phe Tyr Phe Glu Ile Ala Arg Ile Glu Asn Glu Met Lys
        210                 215                 220
Ile Asn Arg Gln Ile Leu Asp Asn Ala Ala Lys Tyr Val Glu His Asp
225                 230                 235                 240
Pro Arg Leu Val Ala Glu His Arg Phe Glu Asn Met Lys Pro Asn Phe
                245                 250                 255
Trp Ser Arg Ile Gly Thr Ala Ala Lys Arg Tyr Pro Gly Val Met
                260                 265                 270
Tyr Ala Phe Thr Thr Pro Leu Ile Ser Phe Phe Gly Leu Phe Asp Ile
            275                 280                 285
Asn Val Ile Gly Leu Ile Val Ile Leu Phe Ile Met Phe Met Leu Ile
        290                 295                 300
Phe Asn Val Lys Ser Lys Leu Leu Trp Phe Leu Thr Gly Thr Phe Val
305                 310                 315                 320
Thr Ala Phe Ile

<210> SEQ ID NO 13
<211> LENGTH: 298
<212> TYPE: PRT
<213> ORGANISM: Molluscum contagiosum gene MC084L

<400> SEQUENCE: 13

Met Ala Glu Ser Glu Ser Thr Ile Pro Leu Tyr Val Leu Pro Val Val
 1               5                  10                  15
Gly Arg Gly Ala Ala Glu Val Val Pro Gly Asn Lys Ser Thr Gly Thr
             20                  25                  30
Val Arg Val Ser Gln Trp Thr Pro Gly Gly Ala Lys Ser Glu Gln Ala
         35                  40                  45
Gly Gln Tyr Tyr Ser Ala Leu Cys Arg Val Leu Cys Ser Ala Glu Ala
     50                  55                  60
Lys Gln Thr Ile Leu Asn His Leu Ser Leu Trp Lys Glu Leu Gly Ser
```

-continued

```
                65                  70                  75                  80
            Glu Ser Ala Pro Lys Ala Ala Gly Ala Glu Ser Glu Tyr Ala Ile Val
                            85                  90                  95

Val Glu Asp Asp Asn Thr Val Gln Pro Leu Leu Leu Gln Ser Ala Ala
                            100                 105                 110

Ala Leu Val Gly Gly Met Arg Ala Gln Gln Val His Val Leu Gln Leu
                            115                 120                 125

Arg Glu Pro Leu His Ala Gly Val Arg Ala Gln Thr Pro Leu Ser Gly
                130                 135                 140

Asn Pro Ser Ala Tyr Val Tyr Pro Ala Arg Leu His Ala Ser Leu Gly
            145                 150                 155                 160

Ala Tyr Ile Ile His Lys Pro Ser Ala Gly Arg Leu His Ala Glu Phe
                            165                 170                 175

Leu Arg Ser Arg Val Thr Ala Gly Leu Pro Leu Glu Leu Pro Arg Val
                            180                 185                 190

Glu Arg Ala Gln Gly Leu Thr Arg Met Val Leu Ala Gly Ser Ser Glu
                            195                 200                 205

Tyr Val Thr His Glu Tyr Arg Leu Arg Asn Glu Leu Arg Gly Arg Glu
                            210                 215                 220

Tyr Gly Ala Ser Leu Arg Ala Arg Ala Gly Ala Trp Leu Ala Arg Asn
            225                 230                 235                 240

Tyr Pro Gln Ala Tyr Ala Ala Ala Thr Thr Pro Val Phe Ser Leu Phe
                            245                 250                 255

Gly Arg Val Asp Val Asn Val Phe Gly Val Leu Ser Val Leu Phe Val
                            260                 265                 270

Leu Val Leu Val Val Phe Asp Val Gln Ser Arg Leu Ala Trp Leu Leu
                            275                 280                 285

Val Gly Ala Leu Ala Ser Gly Leu Leu Gln
                            290                 295
```

H3L ENVELOPE PROTEIN IMMUNIZATION METHODS AND H3L ENVELOPE PASSIVE PROTECTION METHODS

RELATED APPLICATIONS

This application claims the benefit of priority of provisional application Ser. No. 60/626,352, filed Nov. 8, 2004, and provisional application Ser. No. 60/701,738, filed Jul. 21, 2005, which are expressly incorporated herein by reference.

GOVERNMENT FUNDING

Work described herein was supported in part by grants U01AI056464 and AI058365, awarded by the National Institutes of Health. The United States Government may have certain rights in this invention.

TECHNICAL FIELD

The invention relates to methods of treating and protecting against poxvirus infection and pathogenesis including infectious and pathogenic poxviruses (e.g., variola major and variola minor smallpox, monkeypox, cowpox, Molluscum Contagiosum and camelpox) using human, humanized and chimeric antibodies that specifically bind to H3L protein and H3L protein homolog. Furthermore, the invention relates to antibodies that bind to H3L protein and H3L protein homolog, including human, humanized and chimeric antibodies that bind to vaccinia virus H3L protein and H3L protein homolog, and combination compositions and methods for treating and protecting against poxvirus infection and pathogenesis.

INTRODUCTION

Vaccines are one of the most cost-effective medical treatments in modern civilization. A smallpox vaccine was the first human vaccine, and vaccinia virus (VV) is considered the most successful human vaccine, bringing about the worldwide eradication of smallpox disease. Mechanisms of adaptive immune protection elicited by the smallpox vaccine in humans generally remain unclear. There is currently greatly renewed interest in smallpox immunity due to the possible threat of bioterrorism (Henderson et al., *Jama* 281:2127 (1999)). Given this concern, there has been much discussion both about the mechanisms of protection afforded by the smallpox vaccine and the possible development of safer alternatives to Dryvax®, the current US licensed human smallpox vaccine.

Identifying key antigenic targets of VV that are recognized by vaccinated humans and are critical for protection against disease is important for developing a clear understanding of the mechanisms of protection afforded by this prototypic vaccine. In addition, knowledge of key antigenic targets will be instructive for ongoing efforts to design alternative smallpox vaccines, as development and assessment of novel smallpox vaccines will be dependent on a detailed understanding of correlates of immunity.

Vaccines elicit three major types of immune responses that are each considered important in protective long-term immunity: antibodies, memory T cells, and memory B cells (Crotty et al., *Semin Immunol* 16:197 (2004), Plotkin, *J Infect Dis* 187:1349 (2003), Slifka, *Curr Opin Immunol* 16:443 (2004)). Humans with either cellular or humoral immune deficiencies exhibit heightened susceptibility to poxvirus infections (Kempe et al., *Pediatrics* 26:176 (1960), Lane et al., *N Engl J Med* 281:1201 (1969)). Antibodies are the body's first line of defense against infection, and circulating antibodies are the primary indicator of immunity for most human vaccines (Crotty et al., *Semin Immunol* 16:197 (2004), Plotkin, *J Infect Dis* 187:1349 (2003)). Antibodies can be protective against smallpox (variola virus) infection of humans (Fenner et al., *World Health Organization* (1988), Kempe et al., *Bull World Health Organ* 25:41 (1961)), presumably both by neutralizing the initial virus inoculum and by limiting the spread of virus particles within the host after infection is initiated. It is now clear from many studies that memory T cells (CD8, CD4, or in combination) are valuable for protection against a variety of infectious diseases (Welsh et al., *Annu Rev Immunol* 22:711 (2004)), including poxviruses (Belyakov et al., *Proc Natl Acad Sci USA* 100:9458 (2003), Snyder et al., *J Virol* 78:7052 (2004), Tscharke et al., *J Exp Med* 201:95 (2005), Xu et al., *J Immunol* 172:6265 (2004)). The smallpox vaccine is known to elicit T cell responses in humans (Crotty et al., *J Immunol* 171:4969 (2003), Demkowicz et al., *J Virol* 70:2627 (1996), Frey et al., *N Engl J Med* 346:1275 (2002), Hasmmarlund et al., *Nat Med* 9:1131 (2003)) and VV-specific memory T cells are likely to be important components of the vaccine mediated protection against smallpox virus (Kempe, *Pediatrics* 26:176 (1960), Law et al., *Virology* 280:132 (2001), Slifka, *Curr Opin Immunol* 16:443 (2004)). Memory B cells are also likely contributors to human immunity to smallpox, both by their ability to rapidly respond to infection with an anamnestic antibody response, and by their potential ability to replenish long-lived plasma cells to maintain long-term serum antibody levels (Bernasconi et al., *Science* 298:2199 (2002), Crotty et al., *J Immunol* 171:4969 (2003)). Given the renewed interest in smallpox, recent research efforts have focused on identifying the smallpox vaccine targets recognized by the different arms of the adaptive immune system, both in mice and man (Bell et al., *Virology* 325:425 (2004), Fogg et al., *J Virol* 78:10230 (2004), Mathew et al., *J Immunol* 174:2212 (2005), Snyder et al., *J Virol* 78:7052 (2004), Terajima et al., *J Exp Med* 197:927 (2003), Tscharke et al., *J Exp Med* 201:95 (2005)), to obtain information regarding potential correlates of immunity.

SUMMARY

A variety of immunogenic vaccinia virus (VV) antigens eliciting antibody responses have been identified previously in the literature, but the vast majority has been done in animal models. To understand the human humoral immune response to VV, antigen-specificities of the human anti-VV antibody response and which antibody targets are likely to be functionally valuable in protection have been determined using a proteomics approach to first identify the VV antigens recognized by serum from human Dryvax® vaccinees. H3L was a dominant antigen in the human antibody response. Affinity purified human anti-H3L exhibited VV neutralizing activity in vitro. Mice immunized with recombinant H3L protein generated high titers of neutralizing antibodies, and immunized mice were protected against lethal intranasal challenges with pathogenic VV. Neutralizing anti-H3L antibodies were demonstrated to be protective in vivo by serum passive transfer studies.

Polyclonal antibody that binds to H3L protein protected mice from a lethal challenge with pathogenic vaccinia virus strain WR ($VV_{WR}$) when antibody was administered to the animals. The invention therefore provides human, humanized and chimeric H3L protein and H3L protein homologs, compositions including human, humanized and chimeric H3L protein and H3L protein homolog binding antibodies such as pharmaceutical compositions including human, humanized and chimeric anti-H3L and H3L protein homolog polyclonal and monoclonal antibodies, and kits containing antibody. The invention also provides methods for prophylactic and therapeutic treatment of poxvirus infections. In various aspects, the poxvirus is a variola major or variola minor small pox virus. In more particular aspects, the poxvirus is monkeypox, cowpox, Molluscum Contagiosum or camelpox.

Compositions include fully human, humanized and chimeric (e.g., human/mouse chimera) monoclonal antibodies that recognize H3L protein and H3L protein homologs. Methods include passive immunization with human, humanized and chimeric (e.g., human/mouse chimera) polyclonal and monoclonal antibodies that bind to H3L protein or H3L protein homologs, before or after contact with, exposure to or infection with a poxvirus. Methods include treatment methods prior to or before contact with, exposure to or infection with a poxvirus (prophylaxis) as well as treatment methods following contact with, exposure to or infection with a poxvirus (therapeutic) including development of one or more symptoms associated with or caused by poxvirus infection or pathogenesis. Non-limiting examples of symptoms of poxvirus infection or pathogenesis include high fever, fatigue, headache, backache, malaise, rash (maculopapular, vesicular or pustular) or lesions, delirium, vomiting, diarrhea and excess bleeding. Methods of the invention therefore include reducing, decreasing, inhibiting, ameliorating, delaying or preventing onset, progression, severity, duration, frequency or probability of one or more symptoms associated with a poxvirus infection or pathogenesis.

Human, humanized and chimeric antibodies that bind to H3L protein and H3L protein homologs are useful for treating a subject having or at risk of having a poxvirus, before infection (prophylaxis) or following infection (therapeutic). The invention therefore provides methods of using antibodies that bind to H3L protein or H3L protein homologs in treatment (e.g., therapeutic or prophylactic) of poxvirus infection or pathogenesis.

The invention further provides methods for providing a subject with protection against, or protecting a subject from, poxvirus infection or pathogenesis. In one embodiment, a method includes administering a composition comprising a sufficient amount of an antibody that binds to H3L envelope protein or H3L protein homolog to provide the subject with protection against, or protect the subject from, poxvirus infection or pathogenesis.

The invention also provides methods for decreasing susceptibility of a subject to a poxvirus infection or pathogenesis. In one embodiment, a method includes administering a composition comprising a sufficient amount of an antibody that binds to H3L envelope protein or H3L protein homolog to decrease susceptibility of the subject to poxvirus infection or pathogenesis.

The invention further provides methods for decreasing or preventing an adverse side effect caused by vaccination with a Vaccinia virus. In one embodiment, a method includes administering a composition comprising a sufficient amount of an antibody that binds H3L envelope protein or that binds to an H3L protein homolog to decrease or prevent an adverse side effect caused by vaccination with a Vaccinia virus. In another embodiment, a method includes administering a composition comprising a sufficient amount of an antibody that binds H3L envelope protein or an H3L protein homolog to an immune-suppressed or HIV-positive subject to decrease or prevent an adverse side effect caused by vaccination with a Vaccinia virus. In various aspects, side effects decreased or prevented include postvaccinial encephalitis, progressive vaccinia, eczema vaccinatum, generalized vaccinia, accidental infection of close contacts, rashes and periocular infection.

In further aspects, the subject is a candidate for or has been vaccinated with a Vaccinia virus (e.g., modified vaccinia Ankara (MVA), vaccinia virus Lister strain, vaccinia virus LC16m8 strain, vaccinia virus NYCBOH strain, vaccinia virus Wyeth strain or vaccinia virus Dryvax®). In additional various aspects, the subject is administered the antibody that binds H3L envelope protein or H3L protein homolog prior to, concurrently with, following or within 1-2, 2-4, 4-12 or 12-24 hours of vaccination with Vaccinia virus.

Antibodies of the invention can bind to H3L protein or an H3L protein homolog, optionally present on one or more poxvirus (e.g., infectious or pathogenic poxvirus or live or attenuated vaccinia virus) strains or isolates or species. Thus, the antibodies have one or more effects on virus infectivity, replication, proliferation, titer, or onset, progression, severity, frequency, duration or probability of one or more symptoms or complications associated with virus infection or pathogenesis, i.e., an anti-virus (e.g., poxvirus) activity.

Methods of the invention include methods in which partial or complete protection against poxvirus infection or pathogenesis, or a symptom of poxvirus infection or pathogenesis is provided. In one embodiment, a human, humanized or chimeric H3L protein or H3L protein homolog binding antibody inhibits poxvirus infection of a cell in vitro or in vivo, or inhibits poxvirus binding to a cell in vitro or in vivo. In another embodiment, a human, humanized or chimeric antibody reduces or decreases virus titer, infectivity, replication, proliferation, or an amount of a viral protein of one or more poxvirus strains or isolates or species. In yet another embodiment, a human, humanized or chimeric H3L protein or H3L protein homolog binding antibody inhibits, delays, or prevents increases in virus titer, infectivity, replication, proliferation, or an amount of a viral protein of one or more poxvirus strains or isolates or species. In still another embodiment, a human, humanized or chimeric H3L protein or H3L protein homolog binding antibody protects or prevents a subject from infection or pathogenesis, or decreases probability or susceptibility of the subject to infection or pathogenesis by one or more poxvirus strains or isolates or species. In a further embodiment, a human, humanized or chimeric H3L protein or H3L protein homolog binding antibody decreases onset, progression, severity, frequency, duration or probability of one or more symptoms or complications associated with infection or pathogenesis by one or more poxvirus strains or isolates or subtypes. Exemplary symptoms include, for example, high fever, fatigue, headache, backache, malaise, rash (maculopapular, vesicular or pustular) or lesions, delirium, vomiting, diarrhea, and excess bleeding.

H3L or H3L homolog binding antibody can be administered or delivered in accordance with the invention by any suitable in vitro, ex vivo or in vivo method. In various embodiments, a composition is administered prior to, concurrently with, or following poxvirus infection, contact with or exposure to a poxvirus, or vaccination with a Vaccinia virus. In various additional embodiments, a composition is administered prior to, concurrently with, or following a poxvirus infection, contact with or exposure to a poxvirus, or vaccination against a poxvirus. In various aspects, human, humanized or chimeric H3L or H3L homolog binding antibody is administered or in vivo delivered systemically (e.g., intravenous injection, subcutaneous injection, intravenous infusion, intramuscular injection), regionally, or locally to a subject.

Antibodies of the invention include polyclonal and monoclonal antibodies and mixtures thereof, which can be any of IgG, IgA, IgM, IgE, IgD, and any isotype thereof, for example, IgG$_1$, IgG$_2$, IgG$_3$ or IgG$_4$. Antibodies include intact human, humanized and chimeric immunoglobulin molecules with two full-length heavy chains and two full-length light chains (e.g., mature portion of heavy and light chain variable region sequences) as well as subsequences/fragments of heavy or light chain which retain at least a part of a function (H3L protein or H3L homolog binding specificity, H3L protein or H3L homolog binding affinity, or anti-poxvirus function or activity) of parental intact antibody that specifically binds H3L protein or H3L homolog. Subsequences can have the same or substantially the same binding specificity, binding affinity or anti-poxvirus activity as parental intact human, humanized and chimeric anti-H3L or H3L homolog binding antibody.

Exemplary subsequences include Fab, Fab', F(ab')$_2$, Fv, Fd, single-chain Fvs (scFv), disulfide-linked Fvs (sdFv) and V$_L$ or V$_H$, or other H3L/H3L homolog binding fragment of an intact immunoglobulin. Antibodies of the invention, useful in accordance with the invention methods, therefore include heavy-chain variable region sequence and light-chain variable region sequence of antibody that specifically binds H3L protein or H3L protein homolog.

Antibodies include human, humanized and chimeric antibodies having various binding affinities or binding specificities for H3L/H3L homolog, or anti-poxvirus function or activity. Exemplary non-limiting H3L/H3L homolog binding affinities include, K$_d$ of about $10^{-6}$ M to about $10^{-12}$ M, for example. Antibodies of the invention additionally include human, humanized and chimeric antibodies having binding affinity or binding specificity, or anti-poxvirus function or activity, as human polyclonal H3L/H3L homolog binding antibodies isolated from human VIG, as set forth herein. H3L or H3L homolog binding antibodies therefore include human, humanized and chimeric antibodies having the same or different binding affinity for H3L or H3L homolog and having the same or a different binding specificity for H3L or H3L homolog. For example, an H3L or H3L homolog binding antibody of the invention may have an affinity greater or less than 2-5, 5-10, 10-100, 100-1000 or 1000-10,000 fold affinity or any numerical value or range or value within such ranges, as another H3L or H3L homolog binding antibody, such as human polyclonal H3L or H3L homolog binding antibodies isolated from human VIG, as set forth herein.

In further embodiments, an antibody binds to an antigenic region or epitope of H3L or an H3L homolog. Exemplary antigenic regions and epitopes of H3L and H3L homologs include, for example, a region of H3L or of H3L homolog set forth as any of SEQ ID NOS:1-12, or a subsequence or a portion thereof.

```
VV copenhagen strain H3L (SEQ ID NO:1):

MAAVKTPVIV VPVIDRPPSE TFPNVHEHIN DQKFDDVKDN EVMPEKRNVV VVKDDPDHYK

DYAFIQWTGG NIRNDDKYTH FFSGFCNTMC TEETKRNIAR HLALWDSNFF TELENKKVEY

VVIVENDNVI EDITFLRPVL KANHDKKIDI LQMREIITGN KVKTELVMDK NHTIFTYTGG

YDVSLSAYII RVTTALNIVD EIIKSGGLSS GFYFEIARIE NEMKINRQIL DNAAKYVEHD

PRLVAEHRFE NMKPNFWSRI GTAAAKRYPG VMYAFTTPLI SFFGLFDINV IGLIVILFIM

FMLIFNVKSK LLWFLTGTFV TAFI

VV western reserve strain H3L (SEQ ID NO:2):

MAAAKTPVIV VPVIDRLPSE TFPNVHEHIN DQKFDDVKDN EVMPEKRNVV VVKDDPDHYK

DYAFIQWTGG NIRNDDKYTH FFSGFCNTMC TEETKRNIAR HLALWDSNFF TELENKKVEY

VVIVENDNVI EDITFLRPVL KAMHDKKIDI LQMREIITGN KVKTELVMDK NHAIFTYTGG

YDVSLSAYII RVTTALNIVD EIIKSGGLSS GFYFEIARIE NEMKINRQIL DNAAKYVEHD

PRLVAEHRFE NMKPNFWSRI GTAATKRYPG VMYAFTTPLI SFFGLFDINV IGLIVILFIM

FMLIFNVKSK LLWFLTGTFV TAFI

VV MVA strain H3L (SEQ ID NO:3):

MAAVKTPVIV VPVIDRPPSE TFPNVHEHIN DQKFDDVKDN EVMPEKRNVV VVKDDPDHYK

DYAFIQWTGG NIRNDDKYTH FFSGFCNTMC TEETKRNIAR HLALWDSNFF TELENKKVEY

VVIVENDNVI EDITFLRPVL KAMHDKKIDI LQMREIITGN KVKTELVMDK NHAIFTYTGG

YDVSLSAYII RVTTALNIVD EIIKSGGLSS GFYFEIARIE NEMKINRQIL DNAAKYVEHD

PRLVAEYRFE NMKPNFWSRI GTAAAKRYPG VMYAFTTPLI SFFGLFDINV IGLIVILFIM

FMLIFNVKSK LLWFLTGTFV TAFI
```

-continued

VV Acambis MVA strain H3L (SEQ ID NO:4):

MAAVKTPVIV VPVIDRPPSE TFPNVHEHIN DQKFDDVKDN EVMPEKRNVV VVKDDPDHYK

DYAFIQWTGG NIRNDDKYTH FFSGFCNTMC TEETKRNIAR HLALWDSNFF TELENKKVEY

VVIVENDNVI EDITFLRPVL KAMHDKKIDI LQMREIITGN KVKTELVMDK NHAIFTYTGG

YDVSLSAYII RVTTALNIVD EIIKSGGLSS GFYFEIARIE NEMKINRQIL DNAAKYVEHD

PRLVAEYRFE NMKPNFWSRI GTAATKRYPG VMYAFTTPLI SFFGLFDINV IGLIVILFIM

FMLIFNVKSK LLWFLTGTFV TAFI

VV Tian Tian strain H3L (SEQ ID NO:5):

MAAAKTPVIV VPVIDRLPSE TFPNVHEHIN DQKFDDVKDN EVMPEKRNVV VVKDDPDHYK

DYAFIQWTGG NIRNDDKYTH FFSGFCNTMC TEETKRNIAR HLALWDSNFF TELENKKVEY

VVIVENDNVI EDITFLRPVL KAMHDKKIDI LQMREIITGN KVKTELVMDK NHAIFTYTGG

YDVSLSAYII RVTTELNIVD EIIKSGGLSS GFYFEIARIE NEMKINRQIL DNAAKYVEHD

PRLVAEHRFE NMKPNFWSRI GTAATKRYPG VMYAFTTPLI SFFGLFDINV IGLIVILFIM

FMLIFNVKSK LLWFLTGTFV TAFI

Camelpox J3L homolog of VV H3L (SEQ ID NO:6):

MAAAKTPVIV VPVIDRPPSE TFPNVHEHIN DQKFDDVKDN EVMPEKRDVV VVKDDPDHYK

DYAFIQWTGG NIRNDDKYTH FFSGFCNTMC TEETKRNIAR HLALWDSKFF TELENKKVEY

VVIVENDNVI EDITFLRPVL KAMHDKKIDI LQMREIITGN KVKTELVMDK DHAIFTYTGG

YDVSLSAYII RVTTALNIVD EIIKSGGLSS GFYFEIARIE NEMKINRQIL DNAAKYVEHD

PRLVAEHRFE NMKPNFWSRI GTAAAKRYPG VMYAFTTPLI SFFGLFDINV IGLIVILFIM

FMLIFNVKSK LLWFLTGTFV TAFI

Variola major virus (Bangladesh) I3L homolog of
VV H3L (SEQ ID NO:7):

MATVNKTPVI VVPVIDRPPS ETFPNLHEHI NDQKFDDVKD NEVMPEKRNV VIVKDDPDHY

KDYAFIHWTG GNIRNDDKYT HFFSGFCNTM CTEETKRNIA RHLALWDSKF TELENKKVE

YVVIVENDNV IEDITFLRPV LKAMHDKKID ILQMREIITG NKVKTELVMD KNHVIFTYTG

GYDVSLSAYI IRVTTALNIV DEIIKSGGLS SGFYFEIARI ENEMKINRQI MDNSAKYVEH

DPRLVAEHRF ENMKPNFWSR IGTAAVKRYP GVMYAFTTPL ISFFGLFDIN VIGLIVILFI

MFMLIFNVKS KLLWFLTGTF VTAFI

Variola major virus (India) I3L homolog of
VV H3L (SEQ ID NO:8):

MATVNKTPVI VVPVIDRPPS ETFPNLHEHI NDQKFDDVKD NEVMPEKRNV VIVKDDPDHY

KDYAFIHWTG GNIRNDDKYT HFFSGFCNTM CTEETKRNIA RHLALWDSKF TELENKKVE

YVVIVENDNV IEDITFLRPV LKAMHDKKID ILQMREIITG NKVKTELVMD KNHVIFTYTG

GYDVSLSAYI IRVTTALNIV DEIIKSGGLS SGFYFEIARI ENEIKINRQI MDNSAKYVEH

DPRLVAEHRF ENMKPNFWSR IGTAAVKRYP GVMYAFTTPL ISFFGLFDIN VIGLIVILFI

MFMLIFNVKS KLLWFLTGTF VTAFI

Variola minor virus (Garcia) J3L homolog of
VV H3L (SEQ ID NO:9):

MAAVNKTPVI VVPVIDRPPS ETFPNLHEHI NDQKFDDVKD NEVMPEKRNV VIVKDDPDHY

KDYAFIHWTG GNIRNDDKYT HFFSGFCNTM CTEETKRNIA RHLALWDSKF TELENKKVE

```
                        -continued
YVVIVENDNV IEDITFLRPV LKAMHDKKID ILQMREIITG NKVKTELVMD KNHVIFTYTG

GYDVSLSAYI IRVTTALNIV DEIIKSGGLS SGFYFEIARI ENEMKINRQI MDNSAKYVEH

DPRLVAEHRF ENMKPNFWSR IGTAAVKRYP GVMYAFTTPL ISFFGLFDIN VIGLIVILFI

MFMLIFNVKS KLLWFLTGTF VTAFI

Camelpox virus strain M96 homolog of
VV H3L (SEQ ID NO:10):

MAAVNRTPVI VVPVIDRHPS ETFPNVHEHI NDQKFDDVKD NEVMPEKRDV VIVKDDPDHY

KDYAFIQWTG GNIRNDDKYT HFFSGFCNTM CTEETKRNIA RHLALWDSKF FTELENKKVE

YVVIVENDNV IEDITFLRPV LKAMHDKKID ILQMREIITG NKVKTELVMD KNYAIFTYTG

GYDVSLSAYI IRVTTALNIV DEIIKSGGLS SGFYFEIARI ENEMKINRQI MDNSAKYVEH

DPRLVAEHRF ENMKPNFWSR IGTAAAKRYP GVMYAFTTPL ISFFGLFDIN VIGLIVILFI

MFMLIFNVKS KLLWFLTGTF VTAFI

Monkeypox virus (Zaire-96-I-16) H3L homolog of
VV H3L (SEQ ID NO:11):

MAAAKTPVIV VPVIDRPPSE TFPNVHEHIN DQKFDDVKDN EVMQEKRDVV IVNDDPDHYK

DYVFIQWTGG NIRDDDKYTH FFSGFCNTMC TEETKRNIAR HLALWDSKFF IELENKKVEY

VVIIENDNVI EDITFLRPVL KAIHDKKIDI LQMREIITGN KVKTELVIDK DHAIFTYTGG

YDVSLSAYII RVTTALNIVD EIIKSGGLSS GFYFEIARIE NEMKINRQIM DNSAKYVEHD

PRLVAEHRFE TMKPNFWSRI GTVAAKRYPG VMYTFTTPLI SFFGLFDINV IGLIVILFIM

FMLIFNVKSK LLWFLTGTFV TAFI

Cowpox virus (GRI-90) J3L protein homolog of
VV H3L (SEQ ID NQ:12):

MAAAKTPVIV VPVIDRPPSE TFPNVHEHIN DQKFDDVKDN EVMPEKRDVV VVKDDPDHYK

DYAFIQWTGG NIRNDDKYTH FFSGFCNTMC TEETKRNIAR HLALWDSKFF TELENKKVEY

VVIVENDNVI EDITFLRPVL KANHDKKIDI LQMREIITGN KVKTELVMDK DHAIFTYTGG

YDVSLSAYII RVTTALNIVD EIIKSGGLSS GFYFEIARIE NEMKINRQIL DNAAKYVEHD

PRLVAEHRFE NMKPNFWSRI GTAAAKRYPG VMYAFTTPLI SFFGLFDINV IGLIVILFIM

FMLIFNVKSK LLWFLTGTFV TAFI molluscum contagiosum gene MC084L, a VV H3L
homolog (SEQ ID NO:13):

MAESESTIPL YVLPVVGRGA AEVVPGNKST GTVRVSQWTP GGAKSEQAGQ YYSALCRVLC

SAEAKQTILN HLSLWKELGS ESAPKAAGAE SEYAIVVEDD NTVQPLLLQS AAALVGGMRA

QQVHVLQLRE PLHAGVRAQT PLSGNPSAYV YPARLHASLG AYIIHKPSAG RLHAEFLRSR

VTAGLPLELP RVERAQGLTR MVLAGSSEYV THEYRLRNEL RGREYGASLR ARAGAWLARN

YPQAYAAATT PVFSLFGRVD VNVFGVLSVL FVLVLVVFDV QSRLAWLLVG ALASGLLQ
```

Antibodies of the invention include those that have been modified to form oligomers, e.g., through the covalent attachment of an oligomerization domain (e.g., leucine zipper motif) or via a cross-linking agent (e.g., chemical cross linker). Thus, antibodies of the invention include multimeric forms, for example, dimers, trimers, tetramers or higher order human, humanized and chimeric antibody oligomers.

Antibodies of the invention further include one or more heterologous domains that impart a distinct function or activity on an antibody that binds H3L or H3L homolog. Antibodies include an amino acid heterologous domain when one or more amino acids are distinct from the antibody (i.e., they are not a part of the native antibody). In one embodiment, a heterologous domain comprises a binding protein (e.g., receptor or ligand binding), an enzyme activity, a drug, an antiviral, a toxin, an immune-modulator, a detectable moiety or a tag. In one aspect, the binding protein comprises an antibody having a different binding specificity or affinity than a human, humanized or chimeric antibody that specifically binds to H3L protein or an H3L protein homolog.

The invention additionally provides compositions and methods, wherein the composition administered or delivered further includes or excludes other components, or wherein the method further includes or excludes administration or delivery of other components. In one embodiment, a composition delivered by way of a method includes an additional poxvirus protein (e.g., present on one or more IMV, CEV or EEV forms of smallpox), such as B5R, L1R, D8L, A33R, A27L, A17L, L5, A21, H2, A28, A14, A56, A34, A36, A2, or a B5R, L1R, D8L, A33R, A27L, A17L, L5, A21, H2, A28, A14, A56, A34, A36, or A2 homolog. In another embodiment, a composition delivered by way of a method includes an additional antibody that binds to a poxvirus protein (e.g., present on one or more IMV, CEV or EEV forms of smallpox), such as an additional antibody that does not bind to H3L or an H3L homolog, but binds to a poxvirus protein (e.g., B5R, L1R, D8L, A33R, A27L, A17L, L5, A21, H2, A28, A14, A56, A34, A36, A2, or a B5R, L1R, D8L, A33R, A27L, A17L, L5, A21, H2, A28, A14, A56, A34, A36, or A2 homolog). In yet another embodiment, a composition delivered by way of a method excludes an additional poxvirus protein, such as a live (e.g., infectious poxvirus) or attenuated vaccinia virus (e.g., modified vaccinia Ankara (MVA), vaccinia virus Lister strain, vaccinia virus LC16m8 strain, vaccinia virus NYCBOH strain, vaccinia virus Wyeth strain or vaccinia virus Dryvax®). In still another embodiment, a composition delivered by way of a method excludes an additional antibody that binds to a poxvirus protein (e.g., present on one or more IMV, CEV or EEV forms of smallpox, or vaccinia immune globulin (VIG), such as excluding an additional antibody that binds to a non-H3L/H3L homolog poxvirus protein (e.g., B5R, L1R, D8L, A33R, A27L, A17L, L5, A21, H2, A28, A14, A56, A34, A36, A2, or a B5R, L1R, D8L, A33R, A27L, A17L, L5, A21, H2, A28, A14, A56, A34, A36, or A2 homolog).

Combination compositions including H3L and H3L homolog binding antibodies include methods of using such combinations, and methods in which other compositions are administered prior to, concurrently with or following administration of an H3L/H3L homolog antibody. In various embodiments, a composition includes human, humanized or chimeric antibody that binds H3L protein or an H3L protein homolog and an agent that decreases, reduces, inhibits, delays or prevents poxvirus infection or pathogenesis, replication, proliferation, or decreases, reduces, inhibits, delays or prevent the onset, progression, severity, frequency, duration or probability of one or more symptoms or complications associated with poxvirus (e.g., infectious or pathogenic poxvirus or vaccinia virus) infection or pathogenesis. Examples of agents include a plurality (e.g., a pool) of monoclonal or polyclonal antibodies that each bind H3L protein or H3L protein homolog, having the same or a different binding specificity or binding affinity, for H3L or H3L protein homolog. A plurality of H3L or H3L protein homolog antibodies can be individually administered or administered as a combination composition. An additional antibody that binds to a poxvirus protein, different from an H3L or H3L homolog binding antibody, can be administered separately from H3L/H3L homolog binding antibody, or as a combination composition. In specific aspects, the additional antibody that binds to a poxvirus protein binds to IMV, cell-associated enveloped virion (CEV) or extracellular enveloped virion (EEV) forms of smallpox. In more specific aspects, the additional antibody binds to poxvirus protein B5R, L1R, D8L, A33R, A27L, A17L, L5, A21, H2, A28, A14, A56, A34, A36, A2, or a B5R, L1R, D8L, A33R, A27L, A17L, L5, A21, H2, A28, A14, A56, A34, A36, or A2 homolog.

Examples of a combination composition and combination method include administering separately or as a combination composition a protein with H3L/H3L homolog antibody. In one specific aspect, a composition of H3L/H3L homolog binding antibody includes an additional protein (e.g., an infectious or pathogenic poxvirus or vaccinia virus protein). In another specific aspect, a method includes administering an additional poxvirus or vaccinia virus protein prior to, concurrently with or following H3L/H3L homolog binding antibody. An additional poxvirus protein may be present on IMV, CEV or EEV forms of smallpox. In more specific aspects, the additional poxvirus protein is one or more of B5R, L1R, D8L, A33R, A27L, A17L, L5, A21, H2, A28, A14, A56, A34, A36, A2, or a B5R, L1R, D8L, A33R, A27L, A17L, L5, A21, H2, A28, A14, A56, A34, A36, or A2 homolog.

Compositions as well as methods that exclude certain components can exclude, for example, one or more poxvirus proteins or one or more antibodies that bind to poxvirus proteins that are different from H3L/H3L protein homolog. In particular aspects, a composition or method excludes live or attenuated vaccinia virus (e.g., modified vaccinia Ankara (MVA), vaccinia virus Lister strain, vaccinia virus LC16m8 strain, vaccinia virus NYCBOH strain, vaccinia virus Wyeth strain or vaccinia virus Dryvax®), human or non-human vaccinia immune globulin (VIG), or one or more poxvirus proteins or one or more antibodies that bind to poxvirus proteins different from H3L protein or H3L protein homolog (e.g., poxvirus protein B5R, L1R, D8L, A33R, A27L, A17L, L5, A21, H2, A28, A14, A56, A34, A36, A2, or a B5R, L1R, D8L, A33R, A27L, A17L, L5, A21, H2, A28, A14, A56, A34, A36, or A2 homolog).

Pharmaceutical compositions including antibodies of the invention and a pharmaceutically acceptable carrier or excipient are provided. Antibodies can be included in a pharmaceutically acceptable carrier or excipient prior to administration to a subject. Pharmaceutical compositions can be administered to a subject by systemic, regional or local delivery. In one embodiment, a method or carrier is suitable for administration systemically, regionally, or locally to a subject.

Kits that include one or more antibodies of the invention are also provided. In one embodiment, a kit includes instructions for treating (prophylaxis or therapeutic) one or more symptoms or complications associated with poxvirus infection of a subject by one or more poxvirus strains or isolates or species (e.g., virus infectivity, replication, proliferation, titer, onset, progression, severity, frequency, duration or probability of one or more symptoms as set forth herein or known in the art, etc.)

DETAILED DESCRIPTION

Figure 1:
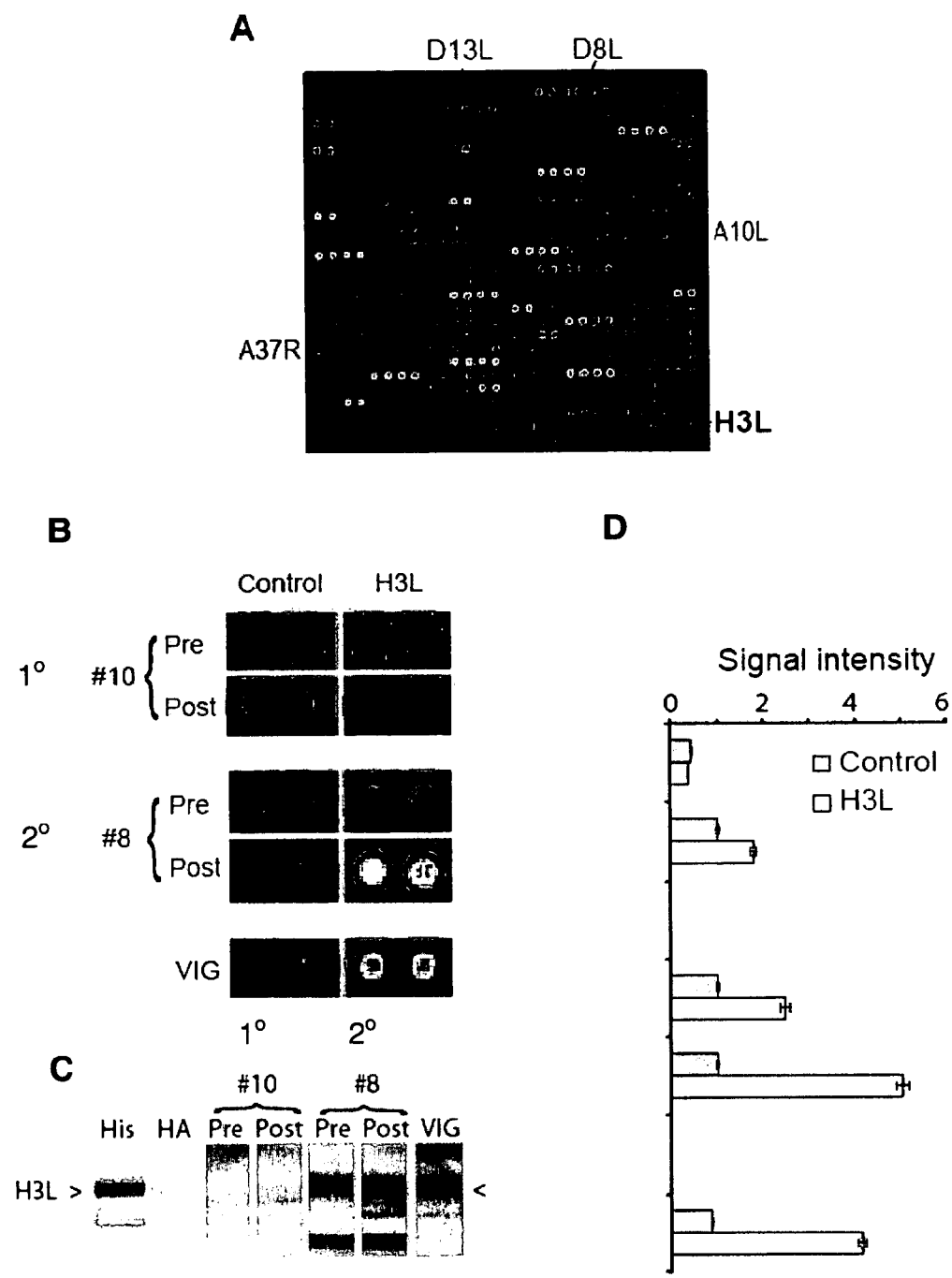
FIGS. 1A-1D illustrate a protein microarray analysis of antibodies generated during vaccinia infection. (A) Scan of a vaccinia virus proteome microarray probed with human serum representative of a secondary response to vaccinia. Specific proteins recognized are annotated; non-annotated proteins are those that are also recognized by vaccinia-naïve human sera and are therefore considered non-specific background. (B) Proteome microarrays showing spots for H3L and control protein (non-expressing plasmid) probed with sera from human donors before ('Pre') and after ('Post') Dryvax® immunization. Data shown are representative of a vaccinia-naive individual (donor #10) and a vaccinated individual (donor #8). (C) Immunoblot of H3L expressed in vitro, probed with the same sera as used in (B). (D) Quantification of anti-H3L and control signal intensities from the arrays shown in (B).

The invention is based at least in part on human, humanized and chimeric antibodies that specifically bind to vaccinia poxvirus H3L protein or H3L protein homologs of other poxviruses. The invention antibodies provide passive protection against an infectious vaccinia virus, and protected animals from a lethal dose challenge of vaccinia virus in a prophylactic mouse model. Antibodies of the invention are therefore useful for prophylactic (prior to poxvirus infection) and therapeutic (following poxvirus infection) treatment. In addition, as invention polyclonal and monoclonal antibodies include human antibodies, which are less likely to induce hypersensitivity from repeated administration and are more likely to remain in a human subjects' body for a longer period of time, human H3L and H3L homolog binding antibodies can be administered to a human subject well in advance of contact with or exposure to infectious or a pathogenic poxvirus such as smallpox, or a live or attenuated vaccinia virus.

In accordance with the invention, there are provided methods for providing a subject with protection against poxvirus infection or pathogenesis, as well as methods for protecting a subject from poxvirus infection or pathogenesis. In one embodiment, a method includes administering a composition comprising a sufficient amount of an antibody that binds to H3L envelope protein or H3L envelope protein homolog to provide the subject with protection against poxvirus infection or pathogenesis. In another embodiment, a method includes administering a composition comprising a sufficient amount of antibody that binds to H3L envelope protein or H3L envelope protein homolog to protect the subject from poxvirus infection or pathogenesis.

Also provided are methods for decreasing susceptibility of a subject to a poxvirus infection or pathogenesis. In one embodiment, a method includes administering a composition comprising a sufficient amount of an antibody that binds to H3L envelope protein or H3L envelope protein homolog to decrease susceptibility of the subject to poxvirus infection or pathogenesis Additionally provided are methods for decreasing or preventing an adverse side effect caused by vaccination with a Vaccinia virus. In one embodiment, a method includes administering a composition comprising a sufficient amount of an antibody that binds H3L envelope protein or H3L envelope protein homolog to a subject to decrease or prevent an adverse side effect caused by vaccination with a Vaccinia virus (live or attenuated) or a vaccinia virus protein. In various aspects, side effects decreased or prevented include postvaccinial encephalitis, progressive vaccinia, eczema vaccinatum, generalized vaccinia, accidental infection of close contacts, rashes and periocular infection. In additional aspects, the subject is a candidate for or has been vaccinated with Vaccinia virus, live or attenuated, or a vaccinia virus protein. In other aspects, the subject is administered the antibody that binds H3L envelope protein or H3L envelope protein homolog prior to, concurrently with, following or within 1-2, 2-4, 4-12 or 12-24 hours of vaccination with Vaccinia virus.

Further provided are methods for decreasing or preventing an adverse side effect in an immune-suppressed subject (e.g., a subject with or at risk of immunodeficiency, such as an HIV-positive subject) caused by vaccination with a Vaccinia virus, live or attenuated, or a vaccinia virus protein. In one embodiment, a method includes administering a composition comprising a sufficient amount of an antibody that binds H3L envelope protein or H3L envelope protein homolog to the subject to decrease or prevent an adverse side effect caused by vaccination with a Vaccinia virus.

Methods of the invention may be practiced prior to, concurrently with, or following poxvirus infection, contact with or exposure to a poxvirus, or vaccination against a Vaccinia virus or vaccinia virus protein. Methods of the invention may be practiced prior to, concurrently with, or following a poxvirus infection, contact with or exposure to a poxvirus, or vaccination against a poxvirus or poxvirus protein.

Methods of the invention include methods that provide partial or complete protection against poxvirus infection or pathogenesis, or a reduction, inhibition, delay, decrease or prevention of a symptom of poxvirus infection or pathogenesis. Methods of the invention include methods that provide partial or complete protection against poxvirus infection or pathogenesis, or reduction, inhibition, delay, decrease or prevention of a symptom of poxvirus infection or pathogenesis. Exemplary symptoms include, for example, high fever, fatigue, headache, backache, malaise, rash (maculopapular, vesicular or pustular) or lesions, viremia, delirium, vomiting, diarrhea, and excess bleeding. Methods include any reduction, inhibition, delay, decrease or prevention in the onset, progression, severity, duration, frequency or probability of one or more symptoms associated with or caused by a poxvirus infection or pathogenesis, as set forth herein or known in the art, or a subjective or objective detectable or measurable improvement of or benefit to the subject.

Methods of the invention are applicable to poxviruses generally, more specifically, members of the viral family Poxviridae. Poxviruses can be infectious or pathogenic, or non-pathogenic. Specific non-limiting examples of pathogenic poxviruses include variola major and variola minor smallpox viruses. Additional specific non-limiting examples of pathogenic poxviruses include monkeypox, cowpox, Molluscum Contagiosum and camelpox. Vaccinia viruses are poxviruses that may be infectious or pathogenic, live or attenuated. Vaccinia viruses may be non-pathogenic, but may be infectious. Non-limiting examples of vaccinia virus express an H3L envelope protein. Typically, non-infectious live or attenuated vaccinia viruses are used to immunize human subjects against variola major and variola minor smallpox virus and related species of poxviruses. Examples of such vaccinia viruses include modified vaccinia Ankara (MVA), vaccinia virus Lister strain, vaccinia virus LC16m8 strain, vaccinia virus NYCBOH strain, vaccinia virus Wyeth strain or vaccinia virus Dryvax®. For example, $VV_{WR}$ is pathogenic in mice (see, Examples 4 and 5). Other non-limiting examples of Poxviridae express homologs to H3L protein, which are proteins having significant sequence identity or similarity to H3L protein set forth as SEQ ID NO:1. H3L homologs can or are very likely to bind to an antibody that binds to H3L protein due to significant sequence identity or similarity.

The term "antibody" refers to a protein that binds to other molecules (antigens) via heavy and light chain variable domains, $V_H$ and $V_L$, respectively. "Antibody" refers to any polyclonal or monoclonal immunoglobulin molecule, or mixtures thereof, such as IgM, IgG, IgA, IgE, IgD, and any subclass thereof, such as $IgG_1$, $IgG_2$, $IgG_3$, $IgG_4$, etc. The term "antibody" also means a functional fragment or subsequence of immunoglobulin molecules, such as, for example, Fab, Fab', $F(ab')_2$, Fv, Fd, scFv and sdFv, unless otherwise expressly stated.

The terms "H3L antibody" or "anti-H3L antibody," and grammatical variations thereof, mean a polyclonal or monoclonal antibody that binds to vaccinia virus intracellular mature virion (IMV) H3L protein, or an H3L protein homolog. Antibodies include specific or selective binding to H3L protein or an H3L protein homolog, which is selective for an epitope present in H3L protein or H3L protein homolog. That is, binding to proteins other than H3L or H3L protein homolog is such that the binding does not significantly interfere with detection of H3L or H3L protein homolog, unless such other proteins have a similar or same epitope as epitope in H3L protein or H3L protein homolog that is recognized by an H3L/H3L homolog antibody. Selective binding can be distinguished from non-selective binding using specificity, affinity and other binding assays, both competitive and non-competitive, known in the art.

The term "isolated," when used as a modifier of an invention composition (e.g., antibodies, modified forms, subsequences, nucleic acids encoding same, etc.), means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude alternative physical forms of the composition, such as multimers/oligomers, modifications (e.g., phosphorylation, glycosylation, lipidation) or derivatized forms, or forms expressed in host cells produced by the hand of man.

An "isolated" composition (e.g., an antibody) can also be "substantially pure" when free of most or all of the materials with which it typically associates with in nature. Thus, an isolated antibody that also is substantially pure does not include polypeptides or polynucleotides present among millions of other sequences, such as antibodies of an antibody library or nucleic acids in a genomic or cDNA library, for example. A "substantially pure" composition can be combined with one or more other molecules. Thus, "substantially pure" does not exclude combinations of compositions As used herein, the term "monoclonal," when used in reference to an antibody, refers to an antibody that is based upon, obtained from or derived from a single clone, including any eukaryotic, prokaryotic, or phage clone. A "monoclonal" antibody is therefore defined herein structurally, and not the method by which it is produced.

The term "human," when used in reference to an antibody, means that the amino acid sequence of the antibody is fully human. A "human H3L antibody" or "human anti-H3L antibody" therefore refers to an antibody having human immunoglobulin amino acid sequences, i.e., human heavy and light chain variable and constant regions that specifically bind to H3L protein or H3L protein homolog. That is, all of the antibody amino acids are human or can or do exist in a human antibody. Thus, for example, an antibody that is non-human may be made fully human by substituting the non-human amino acid residues with amino acid residues that can or do exist in a human antibody. Amino acid residues present in human antibodies, CDR region maps and human antibody consensus residues are known in the art (see, e.g., Kabat, *Sequences of Proteins of Immunological Interest*, 4$^{th}$ Ed. US Department of Health and Human Services. Public Health Service (1987); and Chothia and Lesk *J. Mol. Biol.* 186:651 (1987)). A consensus sequence of human $V_H$ subgroup III, based on a survey of 22 known human $V_H$ III sequences, and a consensus sequence of human $V_L$ kappa-chain subgroup I, based on a survey of 30 known human kappa I sequences is described in Padlan *Mol. Immunol.* 31:169 (1994); and Padlan *Mol. Immunol.* 28:489 (1991)). Human antibodies therefore include antibodies in which one or more amino acid residues have been substituted with one or more amino acids present in any other human antibody.

The term "humanized" when used in reference to an antibody, means that the amino acid sequence of the antibody has non-human amino acid residues (e.g., mouse, rat, goat, rabbit, etc.) of one or more determining regions (CDRs) that specifically bind to the desired antigen (e.g., H3L) in an acceptor human immunoglobulin molecule, and one or more human amino acid residues in the Fv framework region (FR), which are amino acid residues that flank the CDRs. Human framework region residues of the immunoglobulin can be replaced with corresponding non-human residues. Residues in the human framework regions can therefore be substituted with a corresponding residue from the non-human CDR donor antibody to alter, generally to improve, antigen affinity or specificity, for example. In addition, a humanized antibody may include residues, which are found neither in the human antibody nor in the donor CDR or framework sequences. For example, a framework substitution at a particular position that is not found in a human antibody or the donor non-human antibody may be predicted to improve binding affinity or specificity human antibody at that position. Antibody framework and CDR substitutions based upon molecular modeling are well known in the art, e.g., by modeling of the interactions of the CDR and framework residues to identify framework residues important for antigen binding and sequence comparison to identify unusual framework residues at particular positions (see, e.g., U.S. Pat. No. 5,585,089; and Riechmann et al., Nature 332:323 (1988)). Antibodies referred to as "primatized" in the art are within the meaning of "humanized" as used herein, except that the acceptor human immunoglobulin molecule and framework region amino acid residues may be any primate amino acid residue (e.g., ape, gibbon, gorilla, chimpanzees orangutan, macaque), in addition to any human residue.

As used herein, the term "chimeric" and grammatical variations thereof, when used in reference to an antibody, means that the amino acid sequence of the antibody contains one or more portions that are derived from, obtained or isolated from, or based upon two or more different species. That is, for example, a portion of the antibody may be human (e.g., a constant region) and another portion of the antibody may be non-human (e.g., a murine heavy or light chain variable region). Thus, a chimeric antibody is a molecule in which different portions of the antibody are of different species origins. Unlike a humanized antibody, a chimeric antibody can have the different species sequences in any region of the antibody.

As used herein, the terms "H3L," "H3L protein," "H3L envelope protein," "H3L sequence" and "H3L domain" refer to all or a portion of an H3L envelope protein sequence (e.g., a subsequence such as an antigenic region or epitope) isolated from, based upon or present in any naturally occurring or artificially produced (e.g., genetically engineered) poxvirus strain or isolate or subtype or a species of poxvirus. Thus, the term H3L and the like include H3L sequence of vaccinia virus, or H3L homolog I3L of variola major and variola minor small pox virus, as well as naturally occurring variants produced by mutation during the virus life-cycle, produced in response to a selective pressure (e.g., drug therapy, expansion of host cell tropism or infectivity, etc.), as well as recombinantly or synthetically produced H3L sequences. An H3L homolog is a sequence having a significant sequence similarity or identity to exemplary vaccinia virus H3L protein sequence set forth as SEQ ID NO:1. Typical sequence identities of H3L homologs in other poxviruses are 90% or more. Sequence identities of H3L homologs may be less, however. For example, molluscum contagiosum gene MC084L is a VV H3L homolog (SEQ ID NO:13) that has 29% identity, and is 53% similar to H3L set forth as SEQ ID NO:1. H3L homologs also typically have a similar length to exemplary H3L protein sequence set forth as SEQ ID NO:1, usually a length of about 320-330 amino acids. H3L homologs may be referred to by a different name, due to the position of the coding sequence in the virus genome, which determines the name. Exemplary names for H3L homologs are H3L, I3L, J3L and MC084L. Other sequences and the names of H3L homologs are as set forth in SEQ ID NOs:2-12, and are also known in the art.

Methods of the invention can be practiced with any H3L antibody that binds to H3L or H3L homolog, non-limiting sequences to which such antibodies bind are exemplified as set forth in SEQ ID NOs:1-12. Antibodies that bind to H3L or H3L homolog, as set forth in SEQ ID NOs:1-12, may also bind other H3L homologs. Thus, other H3L homologs and antibodies that bind to other such H3L homologs are applicable in the methods of the invention. An exemplary H3L antibody is a polyclonal antibody obtained from human VIG.

H3L/H3L homolog antibodies of the invention include antibodies having kappa or lambda light chain sequences, either full length as in naturally occurring antibodies, mixtures thereof (i.e., fusions of kappa and lambda chain sequences), and subsequences/fragments thereof. Naturally occurring antibody molecules contain two kappa and two lambda light chains. The primary difference between kappa and lambda light chains is in the sequences of the constant region.

H3L/H3L homolog antibodies belong to any antibody class or subclass. Exemplary subclasses for IgG are $IgG_1$, $IgG_2$, $IgG_3$ and $IgG_4$. Invention antibodies include antibodies having either or both of antibody-dependent cell-mediated cytotoxicity (ADCC) and complement-mediated cytotoxicity (CDC) activities.

The term "bind," or "binding," when used in reference to an H3L/H3L homolog binding antibody, means that the antibody specifically binds to all or a part of H3L/H3L homolog envelope protein or an H3L/H3L homolog antigenic fragment or H3/H3L homolog epitope. Thus, an H3L/H3L homolog antibody specifically binds to all or a part of sequence or an antigenic epitope present on H3L or an H3L homolog, but may also bind to other proteins should those proteins have the same or a similar epitope as H3L/H3L homolog antigenic epitope. Antibodies that bind to the same sequence or epitope or a part of the epitope as an antibody that binds to H3L protein or H3L protein homolog, can have more or less relative binding specificity for H3L or homolog, and are expressly included.

A part of an antigenic epitope means a subsequence or a portion of the epitope. For example, if an epitope includes 8 contiguous amino acids, a subsequence and, therefore, a part of an epitope may be 7 or fewer amino acids within this 8 amino acid sequence epitope. In addition, if an epitope includes non-contiguous amino acid sequences, such as a 5 amino acid sequence and an 8 amino acid sequence which are not contiguous with each other, but form an epitope due to protein folding, a subsequence and, therefore, a part of an epitope may be either the 5 amino acid sequence or the 8 amino acid sequence alone.

Epitopes typically are short amino acid sequences, e.g. about five to 15 amino acids in length. Systematic techniques for identifying epitopes are also known in the art and are described, for example, in U.S. Pat. No. 4,708,871. Briefly, a set of overlapping oligopeptides derived from an H3L antigen may be synthesized and bound to a solid phase array of pins, with a unique oligopeptide on each pin. The array of pins may comprise a 96-well microtiter plate, permitting one to assay all 96 oligopeptides simultaneously, e.g., for binding to an anti-H3L monoclonal antibody. Alternatively, phage display peptide library kits (New England BioLabs) are commercially available for epitope mapping. Using these methods, binding affinity for every possible subset of consecutive amino acids may be determined in order to identify the epitope that a particular antibody binds. Epitopes may also be identified by inference when epitope length peptide sequences are used to immunize animals from which antibodies that bind to the peptide sequence are obtained. Continuous epitopes can also be predicted using computer programs, such as BEPITOPE, known in the art (Odorico et al., J. Mol. Recognit. 16:20 (2003)).

Epitopes of H3L and H3L homologs to which antibodies bind include sequences within amino acid sequences set forth as SEQ ID NOs:1-12:

VV copenhagen strain H3L (SEQ ID NO:1):

MAAVKTPVIV VPVIDRPPSE TFPNVHEHIN DQKFDDVKDN EVMPEKRNVV VVKDDPDHYK

DYAFIQWTGG NIRNDDKYTH FFSGFCNTMC TEETKRNIAR HLALWDSNFF TELENKKVEY

VVIVENDNVI EDITFLRPVL KAMHDKKIDI LQMREIITGN KVKTELVMDK NHTIFTYTGG

YDVSLSAYII RVTTALNIVD EIIKSGGLSS GFYFEIARIE NEMKINRQIL DNAAKYVEHD

PRLVAEHRFE NMKPNFWSRI GTAAAKRYPG VMYAFTTPLI SFFGLFDINV IGLIVILFIM

FMLIFNVKSK LLWFLTGTFV TAFI

VV western reserve strain H3L (SEQ ID NO:2):

MAAAKTPVIV VPVIDRLPSE TFPNVHEHIN DQKFDDVKDN EVMPEKRNVV VVKDDPDHYK

DYAFTQWTGG NIRNDDKYTH FFSGFCNTMC TEETKPNIAR HLALWDSNFF TELENKKVEY

VVIVENDNVI EDITFLRPVL KAMHDKKIDI LQMREIITGN KVKTELVMDK NHAIFTYTGG

YDVSLSAYII RVTTALNIVD EIIKSGGLSS GFYFEIARIE NEMKINRQIL DNAAKYVEHD

PRLVAEHRFE NMKPNFWSRI GTAATKRYPG VMYAFTTPLI SFFGLFDINV IGLIVILFIM

FMLIFNVKSK LLWFLTGTFV TAFI

VV MVA strain H3L (SEQ ID NO:3):

MAAVKTPVIV VPVIDRPPSE TFPNVHEHIN DQKFDDVKDN EVMPEKRNVV VVKDDPDHYK

DYAFIQWTGG NIRNDDKYTH FFSGFCNTMC TEETKRNIAR HLALWDSNFF TELENKKVEY

VVIVENDNVI EDITFLRPVL KAMHDKKIDI LQMREIITGN KVKTELVMDK NHAIFTYTGG

YDVSLSAYII RVTTALNIVD EIIKSGGLSS GFYFEIARIE NEMKINRQIL DNAAKYVEHD

PRLVAEYRFE NNKPNFWSRI GTAAAKRYPG VMYAFTTPLI SFFGLFDINV IGLIVILFIM

FMLIFNVKSK LLWFLTGTFV TAFI

VV Acambis MVA strain H3L (SEQ ID NO:4):

MAAVKTPVIV VPVIDRPPSE TFPNVHEHIN DQKFDDVKDN EVMPEKRNVV VVKDDPDHYK

DYAFIQWTGG NIRNDDKYTH FFSGFCNTMC TEETKRNIAR HLALWDSNFF TELENKKVEY

VVIVENDNVI EDITFLRPVL KAMHDKKIDI LQMREIITGN KVKTELVMDK NHAIFTYTGG

YDVSLSAYII RVTTALNIVD EIIKSGGLSS GFYFETARIE NEMKINRQIL DNAAKYVEHD

PRLVAEYRFE NNKPNFWSRI GTAAAKRYPG VMYAFTTPLI SFFGLFDINV IGLIVILFIM

FMLIFNVKSK LLWFLTGTFV TAFI

VV Tian Tian strain H3L (SEQ ID NO:5):

MAAAKTPVIV VPVIDRLPSE TFPNVHEHIN DQKFDDVKDN EVMPEKRNVV VVKDDPDHYK

DYAFIQWTGG NIRNDDKYTH FFSGFCNTMC TEETKRNIAR HLALWDSNFF TELENKKVEY

VVIVENDNVI EDITFLRPVL KAMHDKKIDI LQMREIITGN KVKTELVMDK NHAIFTYTGG

YDVSLSAYII RVTTELNIVD EIIKSGGLSS GFYFEIARIE NEMKINRQIL DNAAKYVEHD

PRLVAEHRFE NNKPNFWSRI GTAATKRYPG VMYAFTTPLI SFFGLFDINV IGLIVILFIM

FMLIFNVKSK LLWFLTGTFV TAFI

Camelpox J3L homolog of VV H3L (SEQ ID NO:6):

MAAAKTPVIV VPVIDRPPSE TFPNVHEHIN DQKFDDVKDN EVMPEKRDVV VVKDDPDHYK

DYAFIQWTGG NIRNDDKYTH FFSGFCNTMC TEETKRNIAR HLALWDSKFF TELENKKVEY

VVIVENDNVI EDITFLRPVL KANHDKKIDI LQMREIITGN KVKTELVMDK DHAIFTYTGG

YDVSLSAYII RVTTALNIVD EIIKSGGLSS GFYFEIARIE NEMKINRQIL DNAAKYVEHD

```
PRLVAEHRFE NMKPNFWSRI GTAAAKRYPG VMYAFTTPLI SFFGLFDINV IGLIVILFIM

FMLIFNVKSK LLWFLTGTFV TAFI
```

Variola major virus (Bangladesh) 13L homolog of
VV H3L (SEQ ID NO:7):

```
MATVNKTPVI VVPVIDRPPS ETFPNLHEHI NDQKFDDVKD NEVMPEKRNV VIVKDDPDHY

KDYAFIHWTG GNIRNDDKYT HFFSGFCNTM CTEETKRNIA RHLALWDSKF FTELENKKVE

YVVIVENDNV IEDITFLRPV LKAMHDKKID ILQMREIITG NKVKTELVMD KNHVIFTYTG

GYDVSLSAYI IRVTTALNIV DEIIKSGGLS SGFYFEIARI ENEMKINRQI MDNSAKYVEH

DPRLVAEHRF ENNKPNFWSR IGTAAVKRYP GVMYAFTTPL ISFFGLFDIN VIGLIVILFI

MFMLIFNVKS KLLWFLTGTF VTAFI
```

Variola major virus (India) 13L homolog of
VV H3L (SEQ ID NO:8):

```
MATVNKTPVT VVPVIDRPPS ETFPNLHEHI NDQKFDDVKD NEVMPEKRNV VIVKDDPDHY

KDYAFIHWTG GNIRNDDKYT HFFSGFCNTM CTEETKRNIA RHLALWDSKF FTELENKKVE

YVVIVENDNV IEDITFLRPV LKAMHDKKID ILQMREIITG NKVKTELVMD KNHVIFTYTG

GYDVSLSAYI IRVTTALNIV DEIIKSGGLS SGFYFEIARI ENEIKINRQI MDNSAKYVEH

DPRLVAEHRF ENMKPNFWSR IGTAAVKRYP GVMYAFTTPL ISFFGLFDIN VIGLIVILFI

MFMLIFNVKS KLLWFLTGTF VTAFI
```

Variola minor virus (Garcia) J3L homolog of
VV H3L (SEQ ID NO:9):

```
MAAVNKTPVI VVPVIDRPPS ETFPNLHEHI NDQKFDDVKD NEVMPEKRNV VIVKDDPDHY

KDYAFIHWTG GNIRNDDKYT HFFSGFCNTM CTEETKRNIA RHLALWDSKF FTELENKKVE

YVVIVENDNV IEDITFLRPV LKAMHDKKID ILQMREIITG NKVKTELVMD KNHVIFTYTG

GYDVSLSAYI IRVTTALNIV DEIIKSGGLS SGFYFEIARI ENEMKINRQI MDNSAKYVEH

DPRLVAEHRF ENMKPNFWSR IGTAAVKRYP GVMYAFTTPL ISFFGLFDIN VIGLIVILFI

MFMLIFNVKS KLLWFLTGTF VTAFI
```

Camelpox virus strain M96 homolog of
VV H3L (SEQ ID NO:10):

```
MAAVNRTPVI VVPVIDRHPS ETFPNVHEHI NDQKFDDVKD NEVMPEKRDV VIVKDDPDHY

KDYAFIQWTG GNIRNDDKYT HFFSGFCNTM CTEETKRNIA RHLALWDSKF FTELENKKVE

YVVIVENDNV IEDITFLRPV LKAMHDKKID ILQMREIITG NKVKTELVMD KNYAIFTYTG

GYDVSLSAYI IRVTTALNIV DEIIKSGGLS SGFYFEIARI ENEMKINRQI MDNSAKYVEH

DPRLVAEHRF ENMKPNFWSR IGTAAAKRYP GVMYAFTTPL ISFFGLFDIN VIGLIVILFI

MFMLIFNVKS KLLWFLTGTF VTAFI
```

Monkeypox virus (Zaire-96-I-16) H3L homolog of
VV H3L (SEQ ID NO:11):

```
MAAAKTPVIV VPVIDRPPSE TFPNVHEHIN DQKFDDVKDN EVMQEKRDVV IVNDDPDHYK

DYVFIQWTGG NIRDDDKYTH FFSGFCNTMC TEETKRNIAR HLALWDSKFF IELENKNVEY

VVIIENDNVI EDITFLRPVL KAIHDKKIDI LQMREIITGN KVKTELVIDK DHAIFTYTGG

YDVSLSAYII RVTTALNIVD EITKSGGLSS GFYFEIARIE NEMKINRQIM DNSAKYVEHD

PRLVAEHRFE TMKPNFWSRI GTVAAKRYPG VMYTFTTPLI SFFGLFDINV IGLIVILFIM

FMLIFNVKSK LLWFLTGTFV TAFI
```

Cowpox virus (GRI-90) J3L protein homolog of

-continued

VV H3L (SEQ ID NO:12):

MAAAKTPVIV VPVTDRPPSE TFPNVHEHIN DQKFDDVKDN EVMPEKRDVV VVKDDPDHYK

DYAFIQWTGG NIRNDDKYTH FFSGFCNTMC TEETKRNIAR HLALWDSKFF TELENKKVEY

VVIVENDNVI EDITFLRPVL KAMHDKKIDI LQMREIITGN KVKTELVMDK DHATFTYTGG

YDVSLSAYII RVTTALNIVD EIIKSGGLSS GFYFEIARIE NEMKINRQIL DNAAKYVEHD

PRLVAEHRFE NMKPNFWSRI GTAAAKRYPG VMYAFTTPLI SFFGLFDINV IGLIVILFIM

FMLIFNVKSK LLWFLTGTFV TAFI molluscuin contagiosum gene MC084L, a VV H3L
homolog (SEQ ID NO:13):

MAESESTIPL YVLPVVGRGA AEVVPGNKST GTVRVSQWTP GGAKSEQAGQ YYSALCRVLC

SAEAKQTILN HLSLWKELGS ESAPKAAGAE SEYAIVVEDD NTVQPLLLQS AAALVGGMRA

QQVHVLQLRE PLHAGVRAQT PLSGNPSAYV YPARLHASLG AYIIHKPSAG RLHAEFLRSR

VTAGLPLELP RVERAQGLTR MVLAGSSEYV THEYRLRNEL RGREYGASLR ARAGAWLARN

YPQAYAAATT PVFSLFGRVD VNVFGVLSVL FVLVLVVFDV QSRLAWLLVG ALASGLLQ

Predicted epitopes for H3L comprise three sequences, denoted PE1, PE2 and PE3, are underlined and in bold text, within an amino acid sequence (SEQ ID NO:1):

MAAVKTPVIV VPVIDRPPSE TFPNVHEHIN DQKFDDVKDN EVMPEKRNVV VVKDDPDHYK

DYAFIQWTGG NIRNDDKYTH FFSGFCNTMC TEETKRNIAR HLALWDSNFF TELENKKVEY

VVIVENDNVI EDITFLRPVL KAMHDKKIDI LQMREIITGN KVKTELVMDK NHTIFTYTGG

YDVSLSAYII RVTTALNIVD EIIKSGGLSS GFYFEIARIE NEMKINRQIL DNAAKYVEHD

PRLVAEHRFE NNKPNFWSRI GTAAAKRYPG VMYAFTTPLI SFFGLFDINV IGLIVILFIM

FMLIFNVKSK LLWFLTGTFV TAFI

Antibodies of the invention having binding specificity for H3L protein or H3L protein homolog can be characterized by any method known in the art, and affinity or specificity, determined by competitive binding, for example, binding assays. Because the binding affinity of H3L/H3L homolog antibodies for H3L or H3L homolog may differ, the antibodies will vary in their ability to compete for binding to H3L/H3L homolog and may provide greater or less effectiveness for treatment of poxvirus infection or pathogenesis than H3L/H3L homolog polyclonal antibodies isolated from VIG. H3L antibodies with more or less affinity for H3L/H3L homolog may have the same or substantially the same binding specificity as the exemplified polyclonal antibodies. A given H3L or H3L protein homolog binding antibody may competitively inhibit binding of another antibody to H3L or H3L homolog by at least 95%, at least 90%, at least 85%, at least 80%, at least 75%, at least 70%, at least 65%, at least 60%, at least 55%, at least 50%, at least 45%, at least 40%, at least 35%, or at least 30%, or less. A given H3L/H3L homolog antibody may not competitively inhibit binding of another antibody to H3L/H3L homolog where the antibodies bind to regions of H3L/H3L homolog that do not interfere with each other.

To obtain H3L or H3L protein homolog binding antibodies that have the same or similar binding specificity as another anti-H3L or H3L protein homolog binding antibody, antibodies that compete for the binding of the antibody to H3L or H3L homolog are screened using a conventional competition binding assay. Screened antibodies selected are those that compete for binding to one or more H3L proteins/homologs.

H3L and H3L protein homolog binding antibodies therefore include human, humanized and chimeric antibodies having the same or different binding affinity for H3L/H3L homolog and having the same or a different binding specificity for H3/H3L homolog. For example, an H3L/H3L homolog antibody of the invention may have an affinity greater or less than 2-5, 5-10, 10-100, 100-1000 or 1000-10,000 fold affinity or any numerical value or range or value within such ranges, as another H3L antibody. Antibodies of the invention therefore include human, humanized and chimeric antibodies having the same or different binding affinity or the same or different binding specificity, or anti-poxvirus function or activity, as human polyclonal H3L or H3L protein homolog binding antibodies isolated from human VIG, as set forth herein.

Exemplary antibody binding affinities for H3L or H3L homologs have a dissociation constant ($K^d$) less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, and $10^{-15}$ M. Typically, binding affinities for H3L/H3L homolog $K_d$ will be less than $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, or $10^{-12}$ M.

At least a part of binding affinity for H3L/H3L homolog can be when the antibody has less affinity for H3L/H3L homolog than a reference antibody, e.g., 1-3-fold, 1-5-fold, 2-5 fold, 5-10-fold, 5-15-fold, 10-15-fold, 15-20-fold, 20-25-fold, 25-30-fold, 30-50-fold, 50-100 fold, 100-500-fold 500-1000-fold, 1000-5000-fold, or less (e.g., $K_d$) affinity, or any numerical value or range of values within such ranges. At least a part of binding affinity for H3L/H3L homolog can be when the antibody has more affinity for H3L/H3L homolog than a reference antibody, e.g., 1-3-fold, 1-5-fold, 2-5 fold, 5-10-fold, 5-15-fold, 10-15-fold, 15-20-fold, 20-25-fold, 25-30-fold, 30-50-fold, 50-100 fold, 100-500-fold 500-1000-fold, 1000-5000-fold, or more (e.g., $K_d$) affinity, or any numerical value or range of values within such ranges.

Binding affinity can be determined by association ($K_a$) and dissociation ($K_d$) rate. Equilibrium affinity constant, K, is the ratio of $K_a/K_d$. An antibody having the same binding affinity as another antibody, means that the dissociation constant ($K_d$) of each antibody is within about 1 to 10 fold (1-10 fold greater affinity or 1-10 fold less affinity, or any numerical value or range or value within such ranges, than the reference antibody). An antibody having "substantially the same" binding affinity as another antibody, means that the dissociation constant ($K_d$) of each antibody is within about 10 to 1000 fold (10-1000 fold greater affinity or 1-1000 fold less affinity).

Association ($K_a$) and dissociation ($K_d$) rates can be measured using surface plasmon resonance (SPR) (Rich and Myszka, *Curr. Opin. Biotechnol.* 11:54 (2000); Englebienne, *Analyst.* 123:1599 (1998)). Instrumentation and methods for real time detection and monitoring of binding rates are known and are commercially available (BiaCore 2000, Biacore AB, Upsala, Sweden; and Malmqvist, *Biochem. Soc. Trans.* 27:335 (1999)).

The term "activity," when used in comparing an antibody to a reference antibody, means that the antibody has at least a part of an activity as the reference antibody, for example, binding affinity (e.g., $K_d$), binding specificity or anti-poxvirus activity. Thus, an antibody having an activity of the polyclonal H3L or H3L homolog binding antibody has at least a part of one or more activities of the H3L or H3L homolog binding antibodies. The term "at least a part" means that the antibody may have less activity but the antibody retains at least a measurable or detectable amount of the activity of the reference antibody, e.g., at least partial binding affinity for H3L or H3L homolog, at least partial anti-poxvirus activity, etc. H3L/H3L homolog binding antibodies having at least a part of one or more anti-poxvirus activities of the polyclonal H3L/H3L homolog binding antibodies exemplified herein may also have a greater activity than a reference antibody, such as polyclonal H3L/H3L homolog binding antibodies exemplified herein.

Antibodies having an activity of polyclonal H3L antibodies can be identified through various methods disclosed herein or known in the art. For example, binding assays against H3L on plates or (ELISA), on cells (cell based ELISA), and specific inhibition of antibody binding to H3L/H3L homolog can be used as a measure of binding specificity as well as affinity. Additional assays include in vitro cell neutralization assays with poxvirus (e.g., vaccinia virus) as well as in vivo animal protection assays as set forth in Examples 1, 4 and 5 in order to ascertain and compare antibodies for the ability to protect animals from vaccinia virus infection or pathogenesis.

Methods of producing polyclonal and monoclonal H3L and H3L homolog binding antibodies are disclosed herein or are known in the art. H3L and H3L homolog binding polyclonal antibodies can be obtained by affinity purification of H3L or H3L homolog antibodies from vaccinia immune globulin (VIG) from vaccinia virus or H3L or H3L homolog immunized animals. Human VIG can be used as a source for human H3L antibodies (see, for example, Example 1).

H3L and H3L homolog binding monoclonal antibodies can be generated using techniques including conventional hybridoma technology, recombinant, and phage display technologies, or a combination thereof (see U.S. Pat. Nos. 4,902,614, 4,543,439, and 4,411,993; see, also *Monoclonal Antibodies, Hybridomas: A New Dimension in Biological Analyses*, Plenum Press, Kennett, McKearn, and Bechtol (eds.), 1980, and Harlow et al., *Antibodies: A Laboratory Manual*, Cold Spring Harbor Laboratory Press, 2nd ed. 1988). H3L and H3L homolog binding monoclonal antibodies can also be obtained by direct cloning of immunoglobulin sequences from animals, including primate or human subjects that have been exposed to a poxvirus, or vaccinated with live or attenuated vaccinia virus or poxvirus protein.

Animals may be immunized with H3L or H3L homolog, including mice, rabbits, rats, sheep, cows or steer, goats, primates including humans, or guinea pigs, in order to obtain antibodies that bind to H3L or H3L homolog. Such animals include genetically modified non-human animals having human IgG gene loci, which are capable of expressing human antibodies. Conventional hybridoma technology using splenocytes isolated from immunized animals that respond to H3L/H3L homolog antigen and fused with myeloma cells can be used to obtain human monoclonal antibodies. A specific non-limiting example is the human transchromosomic KM mice™, which can produce human immunoglobulin genes (WO 02/43478) or HAC mice (WO 02/092812). Transgenic animals with one or more human immunoglobulin genes (kappa or lambda) that do not express endogenous immunoglobulins are described, for example in, U.S. Pat. No. 5,939,598. Such animals can therefore be used to produce human antibodies in accordance with the invention compositions and methods. Additional methods for producing human polyclonal antibodies and human monoclonal antibodies are described (see, e.g., Kuroiwa et al., *Nat. Biotechnol.* 20:889 (2002); WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598). An overview of the technology for producing human antibodies is described in Lonberg and Huszar (*Int. Rev. Immunol.* 13:65 (1995)).

H3L/H3L homolog protein suitable for generating antibodies can be produced by any of a variety of standard protein purification or recombinant expression techniques known in the art. For example, H3L/H3L protein homolog and subsequences thereof can be produced by standard peptide synthesis techniques, such as solid-phase synthesis. A portion of the protein may contain an amino acid sequence such as a T7 tag or polyhistidine sequence to facilitate purification of expressed or synthesized H3L or H3L homolog sequence. H3L or H3L homolog encoding nucleic acid may be expressed in a cell and protein produced by the cells purified or isolated. H3L or H3L homolog protein may be expressed as a part of a larger protein by recombinant methods.

Forms of H3L/H3L homolog suitable for generating an immune response include peptide subsequences of full length H3L/H3L homolog, which typically comprise four to five or more amino acids. Additional forms of H3L/H3L homolog include preparations or extracts (such as live or attenuated vaccinia virus, e.g., modified vaccinia Ankara (MVA), vaccinia virus Lister strain, vaccinia virus LC16m8 strain, vaccinia virus NYCBOH strain, vaccinia virus Wyeth strain or vaccinia virus Dryvax®), partially purified H3L/H3L homolog as well as host cells or viruses that express H3L/ H3L homolog or preparations or mixtures of such expressing cells or viruses.

To increase the immune response, H3L or H3L homolog can be coupled to another protein such as ovalbumin or keyhole limpet hemocyanin (KLH), thyroglobulin and tetanus toxoid, or mixed with an adjuvant such as Freund's complete or incomplete adjuvant. Initial and any optional subsequent immunization may be through intraperitoneal, intramuscular, intraocular, or subcutaneous routes. Subsequent immunizations may be at the same or at different concentrations of H3L or H3L homolog antigen preparation, and may be at regular or irregular intervals.

Antibodies can be humanized using a variety of techniques known in the art including, for example, CDR-grafting (EP 239,400; WO91/09967; U.S. Pat. Nos. 5,225,539; 5,530,101; and 5,585,089), veneering or resurfacing (EP 592,106; EP 519,596; Padlan, *Molecular Immunol.* 28:489 (1991); Studnicka et al., *Protein Engineering* 7:805 (1994); Roguska. et al., *Proc. Nat'l. Acad. Sci. USA* 91:969 (1994)), and chain shuffling (U.S. Pat. No. 5,565,332). Human consensus sequences (Padlan, *Mol. Immunol.* 31:169 (1994); and Padlan, *Mol. Immunol.* 28:489 (1991)) have previously used to humanize antibodies (Carter et al., *Proc. Natl. Acad. Sci. USA* 89:4285 (1992); and Presta et al., *J. Immunol.* 151:2623 (1993)).

Methods for producing chimeric antibodies are known in the art (e.g., Morrison, *Science* 229:1202 (1985); Oi et al., *BioTechniques* 4:214 (1986); Gillies et al., *J. Immunol. Methods* 125:191 (1989); and U.S. Pat. Nos. 5,807,715; 4,816,567; and 4,816,397). Chimeric antibodies in which a variable domain from an antibody of one species is substituted for the variable domain of another species are described, for example, in Munro, *Nature* 312:597 (1984); Neuberger et al., *Nature* 312:604 (1984); Sharon et al., *Nature* 309:364 (1984); Morrison et al., *Proc. Nat'l. Acad. Sci. USA* 81:6851 (1984); Boulianne et al., *Nature* 312:643 (1984); Capon et al., *Nature* 337:525 (1989); and Traunecker et al., *Nature* 339:68 (1989).

Nucleic acid can be used to produce H3L/H3L homolog or binding antibodies. Nucleic acids may be inserted into a nucleic acid construct in which expression of the nucleic acid is influenced or regulated by an "expression control element." An "expression control element" refers to a nucleic acid sequence element that regulates or influences expression of a nucleic acid sequence to which it is operatively linked. Expression control elements include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. Expression control elements include elements that activate transcription constitutively, that are inducible (i.e., require an external signal for activation), or derepressible (i.e., require a signal to turn transcription off; when the signal is no longer present, transcription is activated or "derepressed"), or specific for celltypes or tissues (i.e., tissue-specific control elements).

Nucleic acid may be inserted into a plasmid for propagation into a host cell and for subsequent genetic manipulation. A plasmid is a nucleic acid that can be propagated in a host cell, plasmids may optionally contain expression control elements in order to drive expression of the nucleic acid encoding H3L/H3L homolog or binding antibody in the host cell. A vector is used herein synonymously with a plasmid and may also include an expression control element for expression in a host cell. Plasmids and vectors generally contain at least an origin of replication for propagation in a cell and a promoter. Plasmids and vectors are therefore useful for genetic manipulation and expression of H3L envelope protein or H3L envelope protein homolog as well as binding antibodies.

Nucleic acids encoding variable regions of H3L/H3L homolog antibody heavy and light chains, or encoding full length antibody heavy and light chains can be isolated from a cell such as a hybridoma. Isolated nucleic acids may be inserted into a suitable expression vector, and introduced into suitable host cells which can be cultured for the production of recombinant H3L antibodies.

Antibodies can be modified. Examples of modifications include one or more amino acid substitutions, additions or deletions of the antibody, provided that the modified antibody has all or at least part of an activity of unmodified H3L/H3L homolog antibody, e.g., binding affinity, specificity, or an anti-poxvirus activity, etc.

A particular example of a modification is where an antibody is altered to have a different isotype or subclass by, for example, substitution of the heavy chain constant region. An alteration of Ig subclass can result in an improvement in an anti-poxvirus activity. Thus, modifications include deleting small and large regions of amino acid sequences from an antibody and substituting the deleted region with another amino acid sequence, whether the sequence is greater or shorter in length than the deleted region.

Additional modifications of H3L/H3L homolog antibodies included are antibody derivatives i.e., the covalent attachment of any type of molecule to the antibody. Specific examples of antibody derivatives include antibodies that have been glycosylated, acetylated, phosphorylated, amidated, formylated, ubiquitinated, and derivatization by protecting/blocking groups and any of numerous chemical modifications.

Amino acid substitutions may be with the same amino acid, except that a naturally occurring L-amino acid is substituted with a D-form amino acid. Modifications therefore include one or more D-amino acids substituted for L-amino acids, or mixtures of D-amino acids substituted for L-amino acids. Modifications further include structural and functional analogues, for example, peptidomimetics having synthetic or non-natural amino acids or amino acid analogues and derivatized forms.

Modifications include cyclic structures such as an end-toend amide bond between the amino and carboxy-terminus of the molecule or intra- or inter-molecular disulfide bond. Polypeptides may be modified in vitro or in vivo, e.g., posttranslationally modified to include, for example, sugar residues, phosphate groups, ubiquitin, fatty acids, lipids, etc.

Modifications include an activity or function of a reference composition (e.g., specific binding to H3L or H3L homolog). Modified antibodies having altered characteristics, such as increased binding affinity, can be produced using methods known in the art. For example, affinity maturation techniques can be used to improve antibody binding affinity (US 2004/0162413 A1; U.S. Pat. Nos. 6,656,467, 6,531,580, 6,590,079 and 5,955,358; Fiedler et al., *Protein Eng.* 15:931 (2002); Pancook et al., *Hybrid. Hybridomics* 20:383 (2001); Daugherty et al., *Protein Eng.* 11:825 (1998); Wu et al., *Proc. Nat'l Acad. Sci. USA* 95:6037 (1998); and Osbourn et al., *Immunotechnology* 2:181 (1996)).

A modified protein can have an amino acid substitution, addition or deletion (e.g., 1-3, 3-5, 5-10 or more residues). In a particular non-limiting example, the substitution is a conservative amino acid substitution.

Amino acid substitutions can be conservative or non-conservative and may be in the constant or variable region of the antibody. One or a few conservative amino acid substitutions in constant or variable regions are likely to be tolerated.

Non-conservative substitution of multiple amino acids in hypervariable regions is likely to affect binding activity, specificity or antibody function or activity.

Regional mutability analysis can be used to predict the effect of particular substitutions in CDR and FR domains (Shapiro et al., *J. Immunol.* 163:259 (1999)). In brief, sequence comparison indicates a hierarchy of mutability among di- and trinucleotide sequences located within Ig intronic DNA, which predicts regions that are more or less mutable. Quantitative structure-activity relationship (QSAR) can be used to identify the nature of the antibody recognition domain and, therefore, amino acids that participate in ligand binding. Predictive models based upon OSAR can in turn be used to predict the effect of mutations. For example, the effect of mutations on the association and dissociation rate of an antibody interacting with its antigen has been used to construct quantitative predictive models for both kinetic ($K_a$ and $K_d$) constants, which can in turn be used to predict the effect of other mutations on the antibody (De Genst et al., *J Biol. Chem.* 277:29897 (2002)).

The effect of a substitution can be assayed in order to identify H3L/H3L homolog antibodies retaining at least a part of the binding activity, specificity or antibody function or activity of unsubstituted antibody. For example, an amino acid substitution in a hypervariable region may be assayed for H3L/H3L homolog binding activity or specificity, or an anti-poxvirus activity. Such antibodies having amino acid substitutions are included so long as at least a part of binding affinity, binding specificity, or an anti-poxvirus activity is retained by the substituted antibody.

A "conservative substitution" means the replacement of one amino acid by a biologically, chemically or structurally similar residue. Biologically similar means that the substitution is compatible with biological activity, e.g., specifically binds to H3L/H3L homolog. Structurally similar means that the amino acids have side chains with similar length, such as alanine, glycine and serine, or similar size. Chemical similarity means that the residues have the same charge or are both hydrophilic or hydrophobic. Particular non-limiting examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

The term "identity" and grammatical variations thereof, mean that two or more referenced entities are the same. Thus, where two antibody sequences are identical, they have the same amino acid sequence. The identity can be over a defined area (region or domain) of the protein. "Areas, regions or domains of identity" mean that a portion of two or more referenced entities are the same. Thus, where two antibody sequences are identical over one or more sequence regions they share identity in these regions. The term "substantial identity" means that the identity is structurally or functionally significant. That is, the identity is such that the molecules are structurally identical or have at least one of the same functions (e.g., specific binding to H3L/H3L homolog) even though the molecules are different.

Due to variation in the amount of sequence conservation between structurally and functionally related proteins, the amount of sequence identity for substantial identity will depend upon the protein, the region and any function of that region. Although there can be as little as 30% sequence identity for proteins to have substantial identity, typically there is more, e.g., 50%, 60%, 75%, 85%, 90%, 95%, 96%, 97%, 98%, identity to a reference sequence.

The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol. Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

H3L/H3L homolog binding antibodies include subsequences (e.g., fragments) and modified forms (e.g., sequence variants) as set forth herein. In particular embodiments, H3L/H3L homolog antibody subsequences include an Fab, Fab' and F(ab')2, Fd, single-chain Fvs (scFv), single-chain antibodies, disulfide-linked Fvs (sdFv) and $V_L$ or $V_H$ domain fragments. In particular aspects, an Fab, Fab' and F(ab')2, Fd, single-chain Fvs (scFv), single-chain antibodies, disulfide-linked Fvs (sdFv) and $V_L$ or $V_H$ domain subsequence has at least a part of, has substantially the same or has the same H3L/H3L homolog binding affinity or H3L/H3L homolog binding specificity, or one or more anti-poxvirus activities, e.g., efficacy in inhibiting poxvirus infection of a cell in vitro, or poxvirus infection or pathogenesis in vivo. H3L/H3L homolog binding antibody subsequences, including single-chain antibodies, include variable region(s) alone or in combination with all or a portion of one or more of the following: hinge region, CH1, CH2, and CH3 domains. Also included are antigen-binding subsequences of any combination of variable region(s) with a hinge region, CH1, CH2, and CH3 domains.

H3L/H3L homolog antibody subsequences (e.g., Fab, Fab', F(ab')2, Fd, scFv, sdFv and $V_L$ or $V_H$) can be prepared by proteolytic hydrolysis of the antibody, for example, by pepsin or papain digestion of whole antibodies. The terms "functional subsequence" and "functional fragment" when referring to an antibody of the invention refers to a portion of an antibody that retains at least a part of one or more functions or activities as intact reference antibody.

Antibody fragments produced by enzymatic cleavage with pepsin provide a 5S fragment denoted $F(ab')_2$. This fragment can be further cleaved using a thiol reducing agent to produce 3.5S Fab' monovalent fragments. Alternatively, an enzymatic cleavage using pepsin produces two monovalent Fab' fragments and the Fc fragment directly (see, e.g., U.S. Pat. Nos. 4,036,945 and 4,331,647; and Edelman et al., *Methods Enymol.* 1:422 (1967)). Other methods of cleaving antibodies, such as separation of heavy chains to form monovalent light-heavy chain fragments, further cleavage of fragments, or other enzymatic or chemical may also be used. Genetic techniques include expression of all or a part of the H3L/H3L homolog antibody gene into a host cell such as Cos cells or *E. coli*. The recombinant host cells synthesize intact or single antibody chain, such as scFv (see, e.g., Whitlow et al., In: *Methods: A Companion to Methods in Enzymology* 2:97

(1991), Bird et al., *Science* 242:423 (1988); and U.S. Pat. No. 4,946,778). Single-chain Fvs and antibodies can be produced as described in U.S. Pat. Nos. 4,946,778 and 5,258,498; Huston et al., *Methods Enzymol.* 203:46 (1991); Shu et al., *Proc. Natl. Acad. Sci. USA* 90:7995 (1993); and Skerra et al., *Science* 240:1038 (1988).

Additional modifications of H3L/H3L homolog antibodies included in the invention are antibody additions/insertions. For example, an addition can be the covalent or non-covalent attachment of any type of molecule to the antibody. Specific examples of antibody additions include glycosylation, acetylation, phosphorylation, amidation, formylation, ubiquitination, and derivatization by protecting/blocking groups and any of numerous chemical modifications.

Additions further include fusion (chimeric) polypeptide sequences, which is an amino acid sequence having one or more molecules not normally present in a reference native (wild type) sequence covalently attached to the sequence. A particular example is an amino acid sequence of another antibody to produce a multispecific antibody.

Another particular example of a modified H3L/H3L homolog antibody having an amino acid addition is one in which a second heterologous sequence, i.e., heterologous functional domain is attached that confers a distinct or complementary function upon the antibody. For example, an amino acid tag such as T7 or polyhistidine can be attached to H3L/H3L homolog antibody in order to facilitate purification or detection of H3L/H3L homolog or poxvirus(es). Yet another example is an antiviral attached to an H3L/H3L homolog antibody in order to target cells infected with poxvirus for killing, proliferation inhibition, replication inhibition, etc. Thus, in other embodiments the invention provides H3L/H3L homolog antibodies and a heterologous domain, wherein the domain confers a distinct function, i.e. a heterologous functional domain, on the antibody.

Heterologous functional domains are not restricted to amino acid residues. Thus, a heterologous functional domain can consist of any of a variety of different types of small or large functional moieties. Such moieties include nucleic acid, peptide, carbohydrate, lipid or small organic compounds, such as a drug (e.g., an antiviral), metals (gold, silver).

Linker sequences may be inserted between the antibody sequence and the heterologous functional domain so that the two entities maintain, at least in part, a distinct function or activity. Linker sequences may have one or more properties that include a flexible conformation, an inability to form an ordered secondary structure or a hydrophobic or charged character which could promote or interact with either domain. Amino acids typically found in flexible protein regions include Gly, Asn and Ser. Other near neutral amino acids, such as Thr and Ala, may also be used in the linker sequence. The length of the linker sequence may vary without significantly affecting a function or activity of the fusion protein (see, e.g., U.S. Pat. No. 6,087,329). Linkers further include chemical moieties and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST).

Additional examples of heterologous functional domains are detectable labels. Thus, in another embodiment, the invention provides H3L/H3L homolog antibodies that are detectably labeled.

Specific examples of detectable labels include fluorophores, chromophores, radioactive isotopes (e.g., $S^{35}$, $P^{32}$, $I^{125}$), electron-dense reagents, enzymes, ligands and receptors. Enzymes are typically detected by their activity. For example, horseradish peroxidase is usually detected by its ability to convert a substrate such as 3,3-',5,5-'-tetramethylbenzidine (TMB) to a blue pigment, which can be quantified. Ligands may bind other molecules such as biotin, which may bind avidin or streptavidin, and IgG, which can bind protein A.

It is understood that a H3L/H3L homolog antibody may have two or more variations, modifications or labels. For example, a monoclonal antibody may be coupled to biotin to detect its presence with avidin as well as labeled with $I^{125}$ so that it provides a detectable signal. Other permutations and possibilities will be readily apparent to those of ordinary skill in the art, and are considered to be within the scope of the invention.

Methods for treating poxvirus infection or pathogenesis, of a subject, include administering to the subject an amount of a human, humanized or chimeric H3L/H3L homolog antibody that specifically binds H3L/H3L homolog protein effective to treat poxvirus infection or pathogenesis. The antibody can be administered prior to, concurrently with, or following, exposure to or contact with poxvirus, or poxvirus infection or pathogenesis. Thus, prophylactic as well as therapeutic poxvirus treatment methods are provided.

Methods of the invention include methods in which treatment results in any beneficial effect, which is also considered therapeutic. Particular non-limiting examples of beneficial effects which are also considered therapeutic include reducing, decreasing, inhibiting, delaying or preventing poxvirus infection or pathogenesis, or poxvirus titer, proliferation or replication. Additional non-limiting particular examples of beneficial effects include reducing, decreasing, inhibiting, delaying, ameliorating or preventing onset, progression, severity, duration, frequency, probability or susceptibility of a subject to poxvirus infection or pathogenesis, one or more symptoms or complications associated with poxvirus infection or pathogenesis, or accelerating or facilitating or hastening recovery of a subject from poxvirus infection or pathogenesis or one or more symptoms thereof, etc.

Methods of the invention therefore include providing a beneficial or therapeutic effect to a subject, for example, reducing, decreasing, inhibiting, delaying, ameliorating or preventing onset, progression, severity, duration, frequency or probability of one or more symptoms or complications associated with poxvirus infection or pathogenesis; reducing, decreasing, inhibiting, delaying or preventing increases in poxvirus titer, replication, proliferation, or an amount of a viral protein of one or more poxvirus strains or isolates or subtypes. Stabilizing the condition or symptom, or preventing or inhibiting or delaying a worsening or progression of the condition or a symptom or complication associated with poxvirus infection or pathogenesis, or progression of the underlying poxvirus infection, are also included in various embodiments of the methods of the invention.

Symptoms or complications associated with poxvirus infection and pathogenesis whose onset, progression, severity, frequency, duration or probability can be reduced, decreased inhibited, delayed ameliorated or prevented include, for example, high fever, fatigue, headache, backache, malaise, rash (maculopapular, vesicular or pustular) or lesions, delirium, vomiting, diarrhea, or excess bleeding. Other symptoms of poxvirus infection or pathogenesis, including variola major and variola minor smallpox virus, monkeypox, cowpox, Molluscum Contagiosum and camelpox, are known in the art and treatment thereof in accordance with the invention is provided.

In one embodiment, a method includes administering to the subject an amount of a human, humanized or chimeric antibody that specifically binds H3L envelope protein or H3L protein homolog effective to inhibit virus infection or pathogenesis. In additional embodiments, methods of the invention reduce, decrease, inhibit or prevent susceptibility of the subject to virus infection or pathogenesis or one or more symptoms thereof, by one or more poxvirus strains or isolates or subtypes or a species of poxvirus. In particular aspects, antibody is administered prior to (prophylaxis), concurrently with or following infection of the subject (therapeutic). Methods of the invention, in particular aspects, provide a beneficial or therapeutic effect which includes, for example, reducing or decreasing or delaying onset, progression, severity, frequency, duration or probability of one or more symptoms or complications of poxvirus infection, virus titer, proliferation, replication or an amount of a viral protein of one or more poxvirus strains or isolates or subtypes or species, or susceptibility of a subject to infection by one or more poxvirus strains or isolates or subtypes or species.

The methods of the invention, including treating poxvirus infection or pathogenesis. or a symptom or complication associated with or caused by poxvirus infection or pathogenesis, can therefore result in an improvement in the subjects' condition. An improvement can be any objective or subjective reduction, decrease, inhibition, delay, ameliorating or prevention of onset, progression, severity, duration, frequency or probability of one or more symptoms or complications associated with poxvirus infection or pathogenesis, or virus titer, replication, proliferation, or an amount of a viral protein. An improvement can also be reducing or inhibiting or preventing increases in virus titer, replication, proliferation, or an amount of a viral protein of one or more poxvirus strains or isolates or subtypes or species. An improvement can also mean stabilizing the symptom or complication associated with poxvirus infection or pathogenesis, or inhibiting, decreasing, delaying or preventing a worsening or progression of the symptom or complication associated with poxvirus infection or pathogenesis, or progression of the underlying poxvirus infection. An improvement can therefore be, for example, in any of high fever, fatigue, headache, backache, malaise, rash (maculopapular, vesicular or pustular) or lesions, delirium, vomiting, diarrhea, or excess bleeding, to any degree or for any duration of time.

An improvement also includes reducing or eliminating the need, dosage frequency or amount of an antiviral drug or other agent used for treating a subject having or at risk of having a poxvirus infection, or a symptom or complication associated with poxvirus infection. For example, reducing an amount of a vaccinia virus, attenuated or live, such as modified vaccinia Ankara (MVA), vaccinia virus Lister strain, vaccinia virus LC16m8 strain, vaccinia virus NYCBOH strain, vaccinia virus Wyeth strain or vaccinia virus Dryvax®, or vaccinia virus protein needed for immunization of a subject against poxvirus infection, is also considered an improvement.

An improvement need not be complete ablation of any or all symptoms or complications or side effects associated with poxvirus infection or pathogenesis or vaccinia virus immunization. Rather, treatment may be any objective or subjective measurable or detectable anti-virus effect or improvement. For example, an improvement may reduce, delay or stabilize high fever, but may not be effective at reducing or stabilizing fatigue, headache, backache, malaise, rash (maculopapular, vesicular or pustular) or lesions, delirium, vomiting, diarrhea, or excess bleeding. Thus, a satisfactory clinical endpoint is achieved when there is an incremental improvement or a partial reduction in the subject's condition or associated symptoms or complications, or an inhibition or prevention of worsening or progression of the condition (stabilizing one or more symptoms or complications), over a short or long duration (hours, days, weeks, months, etc.).

Methods for protecting a subject from poxvirus infection, decreasing susceptibility of a subject to poxvirus infection and accelerating or hastening a subject's recovery from poxvirus infection by one or more poxvirus strains or isolates or subtypes or species are further provided. In one embodiment, a method includes administering to the subject an amount of a human, humanized or chimeric antibody that specifically binds H3L envelope protein or H3L envelope protein homolog effective to protect the subject from poxvirus infection, effective to decrease susceptibility of the subject to virus infection. In another embodiment, a method includes administering to the subject an amount of a human, humanized or chimeric antibody that specifically binds H3L envelope protein or H3L envelope protein homolog effective to accelerate or hasten a subject's recovery from poxvirus infection.

In the methods of the invention in which improvement is a desired outcome, such as a prophylactic or therapeutic treatment method that provides an objective or subjective benefit as for poxvirus infection or pathogenesis, an antibody can be administered in a sufficient or effective amount. As used herein, a "sufficient amount" or "effective amount" or an "amount sufficient" or an "amount effective" refers to an amount that provides, in single or multiple doses, alone or in combination with one or more other treatments, therapeutic regimens or agents (e.g., a drug), a long term or a short term detectable or measurable improvement or beneficial effect in a given subject of any degree or for any time period or duration (e.g., for minutes, hours, days, months, years, or cured).

An amount sufficient or an amount effective can but need not be provided in a single administration and can but need not be achieved by an H3L antibody alone or in combination with another compound, agent, treatment or therapeutic regimen. In addition, an amount sufficient or an amount effective need not be sufficient or effective if given in single or multiple doses without a second or additional compound, agent, treatment or therapeutic regimen, since additional doses, amounts or duration above and beyond such doses, or additional drugs, agents, treatment or therapeutic regimens may be included in order to provide a given subject with a detectable or measurable improvement or beneficial effect.

An amount sufficient or an amount effective need not be prophylactically or therapeutically effective in each and every subject treated, nor a majority of subjects treated in a given group or population. An amount sufficient or an amount effective means sufficiency or effectiveness in one particular subject, not a group or the general population. As is typical for such methods, some subjects will exhibit a greater or less response to a treatment method.

Methods of the invention, including, for example, prophylactic and therapeutic treatment methods, are applicable to any poxvirus strain or isolate or subtype or a species of poxvirus, or combination of strains or isolates or subtypes or species of poxviruses. Particular examples are infectious or pathogenic viruses that express an H3L envelope protein or H3L envelope protein homolog, such as a poxviruses expressing a sequence having sufficient sequence homology to H3L protein so as to bind to an antibody that binds to H3L protein. Specific non-limiting examples of poxviruses include variola major or variola minor smallpox virus. Additional specific non-limiting examples include monkeypox, cowpox, Molluscum Contagiosum and camelpox.

Human, humanized and chimeric H3L/H3L homolog antibodies of the invention may be combined with other therapeutic agents, or administered alone prior to, concurrently with, or following administration with other therapeutic agents or treatment protocol or regimen, such agents having anti-virus activity. Agents include those having any activity to decrease, reduce, inhibit or prevent poxvirus infection or pathogenesis, replication, proliferation, or decrease, reduce, inhibit or prevent the onset, progression, severity, frequency, duration or probability of one or more symptoms or complications associated with poxvirus infection or pathogenesis. Accordingly, combination compositions including H3L/H3L homolog antibodies, methods of using such combinations, as well as methods in which other compositions are administered prior to, concurrently with or following administration of an H3L/H3L homolog antibody, in accordance with the methods of the invention, are provided.

Examples of such combination compositions and combination methods include pooled monoclonal or pooled polyclonal antibodies containing two or more different antibodies that each binds H3L/H3L homolog protein, having the same or a different binding specificity, binding affinity, or efficacy in inhibiting poxvirus infection of a cell in vitro or in vivo. In particular embodiments, a plurality of H3L/H3L homolog antibodies are administered separately or as a combination composition in accordance with the invention. In further particular embodiments, an additional antibody that binds to a poxvirus protein, different from an H3L/H3L homolog binding antibody, is administered separately or as a combination composition with H3L/H3L homolog binding antibody in accordance with the invention. In particular aspects, the additional antibody that binds to a poxvirus protein binds to various forms, for example, intracellular mature virion (IMV), cell-associated enveloped virion (CEV) or extracellular enveloped virion (EEV) forms of smallpox. In additional particular aspects, the additional antibody that binds to a poxvirus protein binds to vaccinia protein B B5R, L1R, D8L, A33R, A27L, A17L, L5, A21, H2, A28, A14, A56, A34, A36, A2, or a B5R, L1R, D8L, A33R, A27L, A17L, L5, A21, H2, A28, A14, A56, A34, A36, or A2 homolog.

Additional examples of such combination compositions and combination methods include administering separately or as a combination composition in accordance with the invention an additional poxvirus protein. In one particular embodiment, a composition of H3L/H3L homolog binding antibody includes an additional poxvirus protein. In another particular embodiment, a method includes administering an additional poxvirus protein. In particular aspects, the additional poxvirus protein is present on one or more of IMV, CEV or EEV forms of smallpox. In additional particular aspects, the additional poxvirus protein is one or more of vaccinia B5R, L1R, D8L, A33R, A27L, A17L, L5, A21, H2, A28, A14, A56, A34, A36, A2, or a B5R, L1R, D8L, A33R, A27L, A17L, L5, A21, H2, A28, A14, A56, A34, A36, or A2 homolog.

Compositions used in accordance with the invention, as well as methods, can exclude certain components. In one embodiment, a method in which the composition excludes one or more poxvirus proteins or one or more antibodies that bind to poxvirus proteins that are different from H3L/H3L homolog protein is administered. In particular aspects, a composition excludes or does not consist of live or attenuated vaccinia virus (e.g., modified vaccinia Ankara (MVA), vaccinia virus Lister strain, vaccinia virus LC16m8 strain, vaccinia virus NYCBOH strain, vaccinia virus Wyeth strain or vaccinia virus Dryvax®). In another embodiment, a method excludes administering one or more poxvirus proteins or one or more antibodies that bind to poxvirus proteins different from H3L/H3L homolog protein. In particular aspects, a method excludes administering live or attenuated virus (e.g., poxvirus or modified vaccinia Ankara (MVA), vaccinia virus Lister strain, vaccinia virus LC16m8 strain, vaccinia virus NYCBOH strain, vaccinia virus Wyeth strain or vaccinia virus Dryvax®) with an antibody that binds to H3L/H3L homolog. In additional aspects, a method excludes administering poxvirus protein B5R, L1R, D8L, A33R, A27L, A17L, L5, A21, H2, A28, A14, A56, A34, A36, A2, or a B5R, L1R, D8L, A33R, A27L, A17L, L5, A21, H2, A28, A14, A56, A34, A36, or A2 homolog with an antibody that binds to H3L/H3L homolog. In further aspects, a method excludes administering an antibody that binds to poxvirus protein with antibody that binds to H3L/H3L homolog. For example, human or non-human vaccinia immune globulin (VIG) or antibody that binds to B5R, L1R, D8L, A33R, A27L, A17L, L5, A21, H2, A28, A14, A56, A34, A36, A2, or a B5R, L1R, D8L, A33R, A27L, A17L, L5, A21, H2, A28, A14, A56, A34, A36, or A2 homolog can be excluded in a method or composition that includes an antibody that binds to H3L/H3L homolog.

Subjects appropriate for treatment include those having or at risk of having poxvirus infection or pathogenesis or at risk of having any poxvirus infection. Target subjects therefore include subjects that have been exposed to or contacted with poxvirus, or that have developed one or more adverse symptoms of poxvirus infection or pathogenesis, regardless of the type, timing or degree of onset, progression, severity, frequency, duration of the symptoms.

Target subjects also include those at risk of poxvirus infection or pathogenesis or at risk of having or developing any poxvirus infection. The invention methods are therefore applicable to treating a subject who is at risk of poxvirus infection or pathogenesis, but has not yet been exposed to or contacted with poxvirus. Prophylactic methods are therefore included. Target subjects for prophylaxis can be at increased risk (probability or susceptibility) of poxvirus infection or pathogenesis, as set forth herein and known in the art.

"Prophylaxis" and grammatical variations thereof mean a method in which contact, administration or in vivo delivery to a subject is prior to contact with or exposure to poxvirus. In situations where it is not known that a subject has been contacted with or exposed to poxvirus, administration or in vivo delivery to a subject is prior to manifestation or onset of poxvirus infection or pathogenesis (or an associated symptom). In either case, a method can eliminate, prevent, inhibit, decrease or reduce the probability of or susceptibility towards developing a symptom of poxvirus infection or pathogenesis.

At risk subjects appropriate for treatment include subjects exposed to other subjects having any poxvirus, or where the risk of poxvirus infection is increased due to changes in virus infectivity or cell tropism, immunological susceptibility (e.g., an immunocompromised subject), or environmental factors. At risk subjects appropriate for treatment therefore include human subjects exposed to or at risk of exposure to other humans that may have a poxvirus infection, or are at risk of a poxvirus infection.

H3L/H3L homolog antibodies can be administered in accordance with the methods as a single or multiple dose e.g., one or more times daily, weekly, monthly or annually or between about 1 to 10 weeks, or for as long as appropriate, for example, to achieve a reduction in the onset, progression, severity, frequency, duration of one or more symptoms or complications associated with poxvirus infection or pathogenesis.

Doses can vary depending upon whether the treatment is prophylactic or therapeutic, the onset, progression, severity, frequency, duration probability of or susceptibility of the symptom, the type of virus infection or pathogenesis to which treatment is directed, the clinical endpoint desired, previous or simultaneous treatments, the general health, age, gender or race of the subject and other factors that will be appreciated by the skilled artisan. The skilled artisan will appreciate the factors that may influence the dosage and timing required to provide an amount sufficient for providing a prophylactic or therapeutic benefit.

Typically, for therapeutic treatment, H3L/H3L homolog antibodies will be administered as soon as practical, typically within 24-72 hours after a subject is exposed to or contacted with any poxvirus, or within 24-48 hours after development of one or more symptoms associated with poxvirus infection or pathogenesis (e.g., onset of fever or rash) or symptoms associated with pathogenic poxviruses such as smallpox and monkeypox. For prophylactic treatment, H3L/H3L homolog antibodies can be administered 0-4 weeks, e.g., 2-3 weeks, prior to exposure to or contact with poxvirus since antibodies are predicted to be effective for at least a month following administration. For prophylactic treatment in connection with immunization of a subject with vaccinia virus (live or attenuated) or a poxvirus protein, H3L/H3L homolog antibodies can be administered prior to, concurrently with or following immunization of the subject. Typically, H3L/H3L homolog antibodies are administered concurrently with immunization of a subject with vaccinia virus (live or attenuated) or a poxvirus protein in such prophylactic treatment.

Doses can be based upon current existing passive immunization protocols (e.g., VIG), empirically determined, determined using animal disease models or optionally in human clinical trials. Initial study doses can be based upon the animal studies set forth herein, for a mouse, which weighs about 30 grams, and the amount of polyclonal H3L/H3L homolog antibody administered. The dose can be adjusted according to the mass of a subject, and will generally be in a range from about 1-10 ug/kg, 10-25 ug/kg, 25-50 ug/kg, 50-100 ug/kg, 100-500 ug/kg, 500-1,000 ug/kg, 1-5 mg/kg, 5-10 mg/kg, 10-20 mg/kg, 20-50 mg/kg, 50-100 mg/kg, 100-250 mg/kg, 250-500 mg/kg, or more, two, three, four, or more times per hour, day, week, month or annually. A typical range will be from about 0.3 mg/kg to about 50 mg/kg.

The dose amount, frequency or duration may be proportionally increased or reduced, as indicated by the status of the poxvirus infection or pathogenesis, or any adverse side effects of the treatment or therapy. Dose amounts, frequencies or duration also considered sufficient and effective and are therefore beneficial are those that result in a reduction of the use of another treatment or therapeutic regimen or protocol.

The term "subject" refers to an animal, typically mammalian, such as a non human primate (apes, gibbons, gorillas, chimpanzees, orangutans, macaques), a domestic animal (dogs and cats), a farm animal (poultry such as chickens and ducks, horses, cows, goats, sheep, pigs), experimental animal (mouse, rat, rabbit, guinea pig) and humans. Subjects include animal disease models, for example, the mouse model of poxvirus infection (vaccinia virus) exemplified herein.

H3L/H3L homolog polyclonal and monoclonal antibodies of the invention, including modified forms, variants and subsequences/fragments thereof, and nucleic acids encoding H3L/H3L homolog antibodies, can be incorporated into pharmaceutical compositions. Such pharmaceutical compositions are useful for administration to a subject in vivo or ex vivo.

Antibodies can be included in a pharmaceutically acceptable carrier or excipient prior to administration to a subject. As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration. Thus, pharmaceutical compositions include carriers, diluents, or excipients suitable for administration by various routes. Exemplary routes of administration for contact or in vivo delivery which a composition can optionally be formulated include inhalation, respiration, intubation, intrapulmonary instillation, oral, buccal, intrapulmonary, rectal, intrauterine, intradermal, topical, dermal, parenteral, sublingual, subcutaneous, intranasal, intravascular, intrathecal, intraarticular, intracavity, transdermal, iontophoretic, intraocular, ophthalmic, optical, intravenous, intramuscular, intraglandular, intraorgan, intralymphatic.

Formulations suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays; ointments, salves, gels, or creams as generally known in the art. For contact with skin, pharmaceutical compositions typically include ointments, creams, lotions, pastes, gels, sprays, aerosols, or oils. Carriers which may be used include Vaseline, lanolin, polyethylene glycols, alcohols, transdermal enhancers, and combinations thereof.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Supplementary active compounds (e.g., preservatives, antioxidants, antimicrobial agents including biocides and biostats such as antibacterial, antiviral and antifungal agents) can also be incorporated into the compositions. Pharmaceutical compositions may therefore include preservatives, antioxidants and antimicrobial agents.

Preservatives can be used to inhibit microbial growth or increase stability of the active ingredient thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

An antimicrobial agent or compound directly or indirectly inhibits, reduces, delays, halts, eliminates, arrests, suppresses or prevents contamination by or growth, infectivity, replication, proliferation, reproduction, of a pathogenic or non-pathogenic microbial organism. Classes of antimicrobials include, antibacterial, antiviral, antifungal and antiparasitics. Antimicrobials include agents and compounds that kill or destroy (-cidal) or inhibit (-static) contamination by or growth, infectivity, replication, proliferation, reproduction of the microbial organism.

Exemplary antibacterials (antibiotics) include penicillins (e.g., penicillin G, ampicillin, methicillin, oxacillin, and amoxicillin), cephalosporins (e.g., cefadroxil, ceforanid, cefotaxime, and ceftriaxone), tetracyclines (e.g., doxycycline, chlortetracycline, minocycline, and tetracycline), aminoglycosides (e.g., amikacin, gentamycin, kanamycin, neomycin, streptomycin, netilmicin, paromomycin and tobramycin), macrolides (e.g., azithromycin, clarithromycin, and erythromycin), fluoroquinolones (e.g., ciprofloxacin, lomefloxacin, and norfloxacin), and other antibiotics including chloramphenicol, clindamycin, cycloserine, isoniazid, rifampin, vancomycin, aztreonam, clavulanic acid, imipenem, polymyxin, bacitracin, amphotericin and nystatin.

Particular non-limiting classes of anti-virals include reverse transcriptase inhibitors; protease inhibitors; thymidine kinase inhibitors; sugar or glycoprotein synthesis inhibitors; structural protein synthesis inhibitors; nucleoside analogues; and viral maturation inhibitors. Specific non-limiting examples of anti-virals include nevirapine, delavirdine, efavirenz, saquinavir, ritonavir, indinavir, nelfinavir, amprenavir, zidovudine (AZT), stavudine (d4T), larnivudine (3TC), didanosine (DDI), zalcitabine (ddC), abacavir, acyclovir, penciclovir, valacyclovir, ganciclovir, 1,-D-ribofuranosyl-1,2,4-triazole-3 carboxamide, 9->2-hydroxy-ethoxy methylguanine, adamantanamine, 5-iodo-2'-deoxyuridine, trifluorothymidine, interferon and adenine arabinoside.

Pharmaceutical formulations and delivery systems appropriate for the compositions and methods of the invention are known in the art (see, e.g., *Remington: The Science and Practice of Pharmacy* (2003) 20th ed., Mack Publishing Co., Easton, Pa.; *Remington's Pharmaceutical Sciences* (1990) 18th ed., Mack Publishing Co., Easton, Pa.; *The Merck Index* (1996) $12^{th}$ ed., Merck Publishing Group, Whitehouse, N.J.; *Pharmaceutical Principles of Solid Dosage Forms* (1993), Technonic Publishing Co., Inc., Lancaster, Pa.; Ansel and Stoklosa, *Pharmaceutical Calculations* (2001) $11^{th}$ ed., Lippincott Williams & Wilkins, Baltimore, Md.; and Poznansky et al., *Drug Delivery Systems* (1980), R. L. Juliano, ed., Oxford, N.Y., pp. 253-315).

Antibodies and compositions thereof can be packaged in unit dosage form (capsules, troches, cachets, lozenges, or tablets) for ease of administration and uniformity of dosage. "Unit dosage form" as used herein refers to physically discrete units suited as unitary dosages for the subject to be treated; each unit containing a predetermined quantity of active ingredient optionally in association with a pharmaceutical carrier (excipient, diluent, vehicle or filling agent) which, when administered in one or more doses, is calculated to produce a desired effect (e.g., prophylactic or therapeutic effect). Unit dosage forms also include, for example, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Unit dosage forms further include compositions for transdermal administration, such as "patches" adapted to remain in contact with the epidermis of the intended recipient for an extended or brief period of time. The individual unit dosage forms can be included in multi-dose kits or containers. Pharmaceutical formulations can be packaged in single or multiple unit dosage form for ease of administration and uniformity of dosage.

The invention provides kits comprising H3L/H3L homolog antibodies, combination compositions and pharmaceutical formulations thereof, packaged into suitable packaging material. A kit typically includes a label or packaging insert including a description of the components or instructions for use in vitro, in vivo, or ex vivo, of the components therein. A kit can contain a collection of such components, e.g., two or more human H3L/H3L homolog antibodies alone or in combination with an anti-poxvirus agent (e.g., a poxvirus protein or an antibody that binds to a poxvirus protein different than H3L or H3L homolog) or drug.

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a condition, disorder or disease for which a kit component may be used. Labels or inserts can include instructions for the clinician or subject for using one or more of the kit components in a method, or treatment protocol or therapeutic regimen. Instructions can include dosage amounts, frequency or duration, and instructions for practicing any of the methods, treatment protocols or prophylactic or therapeutic regimes described herein. Exemplary instructions include, instructions for treating poxvirus infection or pathogenesis. Kits of the invention therefore can additionally include labels or instructions for practicing any of the methods of the invention described herein including treatment, detection, monitoring or diagnostic methods. Thus, for example, a kit can include an H3L/H3L homolog antibody that has one or more anti-poxvirus activities as set forth herein, together with instructions for administering the antibody in a prophylactic or therapeutic treatment method of the invention.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Invention kits can additionally include a growth medium (e.g., for an H3L/H3L homolog binding antibody producing cell line), buffering agent, or a preservative or a stabilizing agent in a pharmaceutical formulation containing a human, humanized or chimeric H3L/H3L homolog binding antibody. Each component of the kit can be enclosed within an individual container and all of the various containers can be within a single package. Invention kits can be designed for cold storage. Invention kits can further be designed to contain human, humanized or chimeric H3L/H3L homolog binding antibody producing hybridoma or other host cells (e.g., CHO cells). The cells in the kit can be maintained under appropriate storage conditions until the cells are ready to be used. For example, a kit including one or more hybridoma or other cells can contain appropriate cell storage medium so that the cells can be thawed and grown.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "an H3L or H3L homolog antibody" includes a plurality of such antibodies and reference to "an anti-poxvirus activity or function" can include reference to one or more activities or functions, and so forth.

As used herein, all numerical values or numerical ranges include integers within such ranges and fractions of the values or the integers within ranges unless the context clearly indicates otherwise. Thus, to illustrate, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. For example, in certain embodiments or aspects of the invention, antibodies that specifically bind to poxvirus proteins different from H3L/H3L homolog protein are excluded. In certain embodiments or aspects of the invention, poxvirus proteins different from H3L/H3L homolog are excluded. Thus, even though the invention is generally not expressed herein in terms of what the invention does not include aspects that are expressly not included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes various materials and methods.

Sera: Human antibodies of vaccinia immune globulin (VIG; Cangene Corp., Winnipeg, Canada) were used. VIG is a high titer immunoglobulin fraction purified from sera pooled from multiple vaccinia-hyperimmune human vaccines. Sera from a panel of 15 individual human volunteers donated blood before and 28 days, or 30 days, after vaccination with Dryvax®. Sera were stored as aliquots at −70° C. Individual donors were either vaccinia naïve at the time of vaccination (n=4), or had been vaccinated against smallpox in childhood and were receiving a booster vaccination (n=11). Mouse anti vaccinia virus serum was obtained by retro-orbital bleed from five BALB/c mice on day 19, and at various time points, post-infection with $5\times10^5$ pfu vaccinia virus WR strain ($VV_{WR}$) or $1\times10^5$ pfu vaccinia virus NYBOH strain ($VV_{NYBOH}$) administered intraperitoneally. Mouse anti-H3L sera were generated by emulsifying purified H3L (2 mg/ml in phosphate buffered saline (PBS)) with an equal volume of Freund's complete adjuvant and boosting 3 weeks later with antigen in incomplete Freund's adjuvant (200 µg H3L/dose). Rabbit anti-H3L sera for passive transfer studies were obtained by immunizing two rabbits with recombinant H3L protein emulsified in Freund's complete adjuvant and boosting seven times over 12 weeks with antigen in incomplete Freund's adjuvant (200 µg H3L/dose).

Viruses: $VV_{WR}$ stocks were grown on HeLa cells in T175 flasks, infecting at a multiplicity of infection of 0.5 (MOI=0.5). Cells were harvested at 60 hours, and virus was isolated by rapid freeze-thawing the cell pellet 3 times in a volume of 2.3 ml RPMI+1% FCS. Cell debris was removed by centrifugation. Clarified supernatant was frozen at −80° C. as virus stock. $VV_{WR}$ stocks were titered on Vero cells (~2× $10^8$ PFU/ml). $VV_{NYBOH}$ stocks were generated as low passage stocks from commercial Dryvax®, using same conditions as for $VV_{WR}$ above.

Production and staining of vaccinia proteome microarray: High throughput cloning and expression platform is described (Davies et al., *Proc Natl Acad Sci USA* 102:547 (2005) submitted). PCR primers comprising 20 bp gene-specific sequence with 33 bp 'adapter' sequences were used in PCR reactions with $VV_{WR}$ genomic DNA as template. The adapter sequences, which become incorporated into the termini flanking the amplified gene, were homologous to the cloning site of T7 expression vector pNH is CHA (Gene Therapy Systems, San Diego, Calif.) and allow the PCR products to be cloned by homologous recombination in competent DH5α cells. The adaptors incorporated 5' poly-histidine epitope, ATG translation start codon, and 3' hemagglutinin epitope and T7 terminator. Sequence confirmed plasmids were expressed in 5 hours in vitro transcription/translation reactions (RTS 100 kits from Roche). Protein expression was monitored either by dot blot or microarray using both monoclonal anti-polyhistidine (clone His-1 from Sigma) and monoclonal anti-hemagglutinin (clone 3F10 from Roche) antibodies followed by appropriate secondary antibodies. Microarrays were printed onto nitrocellulose coated glass slides (FAS™ from Schleicher & Schuell Bioscience) using an Omni Grid 100 microarray printer (Gene Machines). Prior to array staining, sera were diluted to 1/50 in Protein Array Blocking Buffer (Schleicher & Schuell Bioscience) containing *E. coli* lysate at a final concentration of 10%, and incubated at 18° C. for 1 hour with constant mixing. Arrays were rehydrated in blocking buffer for 30 minutes and probed with the pre-treated sera for 1-2 hours at 18° C. with constant agitation. Slides were then washed 5 times in Tris buffer containing 0.05% Tween-20 and bound antibodies detected by incubation in Cy 3-conjugated goat anti-human IgA+IgG+IgM (H+L) secondary antibody (Jackson ImmunoResearch) diluted 1/2500 in blocking buffer. After washing 5 times, slides were air dried under brief centrifugation and stored at 18° C. in a desiccator. Arrays were examined in a GSI Lumonics ScanArray 4000 confocal glass slide scanner and intensities quantified using QuantArray software. All signal intensities were corrected for background, and vaccinia-specific signals either plotted as signal intensities.

Whole vaccinia virus ELISA, murine: Vaccine virus (VV) antigen preparation for antibody ELISA use was done by ultraviolet (UV) inactivating stock $VV_{NYBOH}$ with trioxsalen/psoralen (4'aminomethyl-trioxsalen HCl. Calbiochem) (Crotty et al., *J. Immunological Methods* 286:111-122 (2004), Crotty et al., *J Immunol* 171:4969 (2003)). $1 \times 10^8$ PFU/ml $VV_{NYBOH}$ in 0.1% bovine serum albumin (BSA) and 10 ug/ml trioxsalen was incubated for 10 minutes and room temperature and then UV inactivated with 2.25 J/cm$^2$ (Stratalinker 1800, Stratagene, Calif.). This resulted in a greater than $10^8$-fold reduction in PFU. UV inactivated virus was then used at a 1:25 dilution in PBS with BSA supplemented to a final concentration of 0.1%. Direct ELISA was done using Nunc Polysorp flat-bottomed 96-well plates coated overnight with 100 ul/well VV antigen. Plates were washed and serum samples were added to the plate and serially diluted (2-fold dilutions) in PBS+0.05% Tween-20+10% FCS. Caltag HRP conjugated goat anti-mouse IgGγ diluted 1:1000 in PBS+0.05% Tween-20+10% FCS was used for detection. Plates were developed using o-phenylenediamine and the OD490 nm was read on a SpectraMax 250 (Molecular Devices). Anti-VV serum IgG antibody titer was determined as endpoint titer 0.1 OD greater than background (no serum well).

Purification of H3L: Cultures of *E. coli* (strain BL21) transformed with pNH is CHA/H3L ($VV_{WR}$ strain H3L) were grown in the presence of kanamycin to an $OD_{600\ nm}$=0.4-0.6 and induced with 0.4 mM IPTG overnight. Cell pellets were resuspended in 5 ml/g wet pellet in lysis buffer (Bugbuster™ reagent from Novagen). Lysates were clarified at 30,500×g and frozen at −80° C. Cell-free extracts were loaded onto 1 ml or 5 ml nickel-coated columns (Amersham), washed in buffer A (500 mM NaCl, 20 mM $NaH_2PO_4$, 20 mM imidazole, 10% glycerol), and eluted in a stepwise gradient (200-500 mM) of imidazole. H3L elutes at 325 mM imidazole. Eluted protein was then dialyzed into PBS and adjusted to 1-1.5 mg/ml.

Affinity Purification of H3L antibodies from VIG: Human anti-H3L antibody was obtained by affinity purification from VIG. Recombinant H3L obtained from liter cultures of IPTG-induced *E. coli* was subjected to SDS PAGE and immunoblotted onto nitrocellulose membrane. H3L band was cut from the nitrocellulose and cut into fragments, blocked for 4 hours in 5% fat-free milk powder in PBS, washed, and then incubated overnight with constant agitation at 4° C. in 1 ml VIG diluted 1/10 in blocking buffer. After washing (10 times in TBS+0.05% Tween-20) the bound antibody was eluted for 1 minute in 0.1M glycine/0.15M NaCl, pH 2.4, and collected into 1M Tris-HCl pH 8.2. The eluate was then concentrated and exchanged into serum-free IMDM using Centricon™ columns. Prior to neutralization assay, the quantity of purified antibody was quantified by Bradford assay, and the purity of the antibody confirmed using Western blots of whole vaccinia virus particles transferred to nitrocellulose. Pure antibody gave a single band on Western blot corresponding to H3L.

Plague reduction neutralization titers (PRNT): CV-1 cells or VeroE6 cells were seeded into 12-well Costar plates (Corning Inc, Corning, N.Y.) and used within 2 days of reaching confluency. Test sera were heat-inactivated (56° C., 30 minutes) and two-fold serial dilutions performed in serum-free DMEM or IMDM. Diluted sera were then incubated in an equal volume of sonicated vaccinia virus WR (103 pfu/ml) overnight at 37° C. (Newman et al., *J Clin Microbiol* 41:3154 (2003)). CV-1 cells were rinsed in serum-free medium, the medium aspirated and 100 ul of virus/serum mixture added to each well in duplicate and left to adsorb for 60 minutes at 37° C. with periodic swirling. One ml of complete medium was then added and the plates incubated for 2 days for the plaques to develop. The medium was then aspirated and cells fixed and stained in one step with 0.1% crystal violet in 20% ethanol, and plaques quantified over white light transillumination. Data were plotted and a curve of best fit applied by eye. The neutralization titer (NT50) was defined as the dilution of the serum that reduced the average number of plaques by 50% compared to the mean number of plaques of controls with no serum, according to the formula (Burleson et al., *Academic Press* (1992)): NT50=DL+[(P50−PL)(DH−DL)/(PH−PL)], where DL is the reciprocal of the lower dilution bracketing the 50% endpoint, DH is the reciprocal of the higher dilution bracketing the 50% endpoint, P50 is the number of plaques at the 50% endpoint, PL is the number of plaques at the lower dilution bracketing the 50% endpoint, PH is the number of plaques at the higher dilution bracketing the 50% endpoint.

Depletion of H3L from human sera and VIG: Nickel-coated resin columns (Hi-Trap, Pharmacia) were loaded with clarified lysates from pNH is CHA/H3L or pNH is CHA (control) transformed BL-21 cells as described above and washed extensively in buffer A. One ml of VIG or human serum (diluted to 1/250 or 1/10, respectively, in buffer A was then passed through each column, and the eluate recirculated through the same column six times. An additional 1 ml of buffer A was used to wash the column and the eluate pooled with the first 1 ml eluate. The depleted VIG or sera was then desalted into 1 ml of MEM medium using Centricon™ columns (Amicon, Millipore). All depleted VIG and sera were monitored for loss of H3L reactivity by testing against protein microarrays or immunoblot strips into which whole WR virus had been transferred.

Mouse immunization and protection studies: Female BALB/c mice (6-10 weeks old) were immunized with 50 ug purified H3L protein emulsified in complete Freund's adjuvant (Difco Laboratories, Detroit Mich.) and boosted 3 weeks later with antigen in incomplete Freund's adjuvant (Difco). Three weeks after boosting, mice were challenged intranasally with 1 50% lethal dose (1 $LD_{50}$) or 5 $LD_{50}$ of WR and body weight measurements taken daily. Mice were sacrificed when weight loss was greater than 25%.

Vaccinia intranasal infections and protection studies: Age-matched female BALB/c mice were used in all studies. To infect the mice, $VV_{WR}$ was placed on the nares of the mouse using a Pipetman, in a volume of 10 ul, which was then inhaled by the mouse. Mice were weighed daily from days 0-21 to assess disease progression and protective efficacy of vaccinations. After intranasal infection with $VV_{WR}$, mice develop a systemic infection and exhibit severe weight loss.

Figure 4:
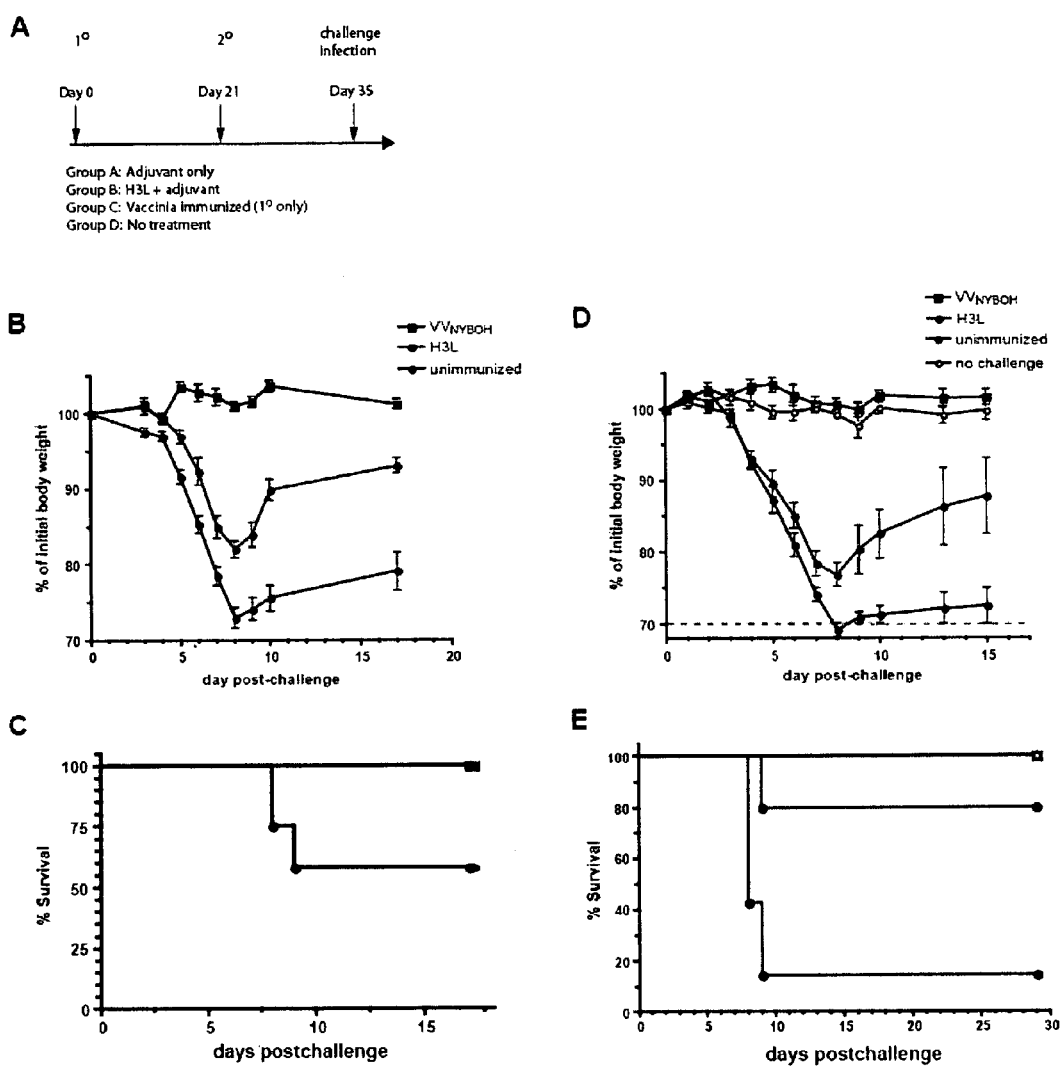
FIGS. 4A-4E show data indicating that mice immunized with H3L (SEQ ID NO:1) develop protective neutralizing antibodies. (A) Immunization and challenge protocol. (B) Body weight was tracked after intranasal challenge with 1 $LD_{50}$ of $VV_{WR}$. (C) Survival curve after intranasal challenge with 1 $LD_{50}$ of $VV_{WR}$. (D) Body weight was tracked after intranasal challenge of older mice with $1\times10^5$ $VV_{WR}$. (E) Survival curve after intranasal challenge of older mice with $1\times10^5$ $VV_{WR}$.

Unprotected mice begin to exhibit some weight loss by day 4, and have greater than 30% weight loss by day 8, with nadir or death between days 8-12. $1>10^5$ PFU $VV_{WR}$ was a standard lethal dose given to 10 week old BALB/c females. In a series of studies, virus doses were titrated to establish $LD_{50}$'s at different ages of BALB/c females, such that an appropriate $LD_{50}$ dose was chosen for each vaccination study based on the age of the mice used. Mice used were all 6-13 weeks old at the time of challenge, depending on the study. Consistent results were obtained with the $VV_{WR}$ intranasal challenge system (FIG. 4). It has been reported that there are slight variations of this protection model and it is a well accepted murine model of protection against vaccinia virus (Alcomi et al., *Cell* 71:153 (1992), Belyakov et al., *Proc Natl Acad Sci USA* 100:9458 (2003), Ramirez et al., *J Gen Virol* 83:1059 (2002), Reading et al., *J Gen Virol* 84:1973 (2003), Zhang et al., *J Virol* 74:11654 (2000)). For H3L protection studies, female BALB/c mice (6 weeks old) were immunized with 50 ug purified H3L protein emulsified in Ribi (first series of studies) or complete Freund's adjuvant (Difco Laboratories, Detroit Mich.) (second series of studies) and then boosted three weeks later with H3L protein in Ribi (first series of studies) or incomplete Freund's adjuvant (second series of studies). Control mice received adjuvant alone. In passive transfer protection studies, rabbit polyclonal anti-H3L antiserum or control pre-immune rabbit serum were injected intraperitoneally (200 ul) into groups of 10 BALB/c mice one day prior to intranasal challenge with of $VV_{WR}$ as described above.

Statistical analysis: Tests were performed using Prism 4.0 (GraphPad, San Diego, Calif.). Statistics were done using two-tailed, unpaired T test with 95% confidence bounds unless otherwise indicated. Data to be concurrently analyzed from multiple studies was first normalized prior to statistical testing. Data involving three or more groups was analyzed by one way ANOVA with Bonferroni Multiple Comparisons post test. Error bars are ± one SEM unless otherwise indicated. Kaplan Meier Suvival analysis was used for survival curves. Weight loss data was analyzed as "area under curve" comparisons, with each mouse treated as an individual data point and significance of differences between experimental conditions determined by one way ANOVA.

Example 2

This example describes proteome microarray screening identifying antibody profiles in response to vaccinia immunization.

Vaccinia protein microarrays representing 194 of the 202 proteins (97%) of the vaccinia proteome were screened with sera from a panel of human volunteers before and after immunization with vaccinia. H3L was a dominant component of the anti-vaccinia virus human antibody response (FIG. 1A). H3L is a vaccinia virus surface protein expressed on intracellular mature virions (IMV) and participates in attachment of vaccinia virus to target cells (da Fonseca et al., *J Virol* 74:7508 (2000), da Fonseca et al., *J Virol* 74:7518 (2000), Lin et al., *J Virol* 74:3353 (2000)).

FIG. 1A shows a representative array of a serum of individual (donor #12) undergoing a secondary response after boosting. Donor #12 was first immunized in 1976 at the age of 5 years, and then boosted with Dryvax® 26 years later. Serum was taken 30 days after a Dryvax® boost (FIG. 1A). Annotated spots are vaccine specific antibody reactives whereas non-annotated signals are irrelevant non-vaccinia virus 'background' antibody reactives that are also seen in Dryvax®-naïve human sera (Davis et al., *Proc Natl Acad Sci USA* 102:547 (2005)). The array comprises 376 different clones representing 194 proteins (96%) of the vaccinia proteome (FIG. 1A). Proteins were expressed in vitro and printed without further purification on nitrocellulose-coated slides (FIG. 1A). While each human donor generated a slightly different profile of antibodies, a core of 3-5 antigens was seen by the majority of people on this near complete proteome array. These antigens comprised H3L, A10L and D13L.

After vaccination, naïve donors typically recognized a wider profile of antigens (mean=6.6 antigens per donor, range=5-9) than previously immunized donors (mean=2.8 antigens per donor, range=1-4), although the responses in both case were focused on the immunodominant antigens. H3L is of interest as it is the only envelope protein of the three dominant antigens.

FIG. 1B shows antibodies to H3L in representative individuals, a vaccine naïve individual and a different previously vaccinate donor, undergoing primary and secondary responses to Dryvax® vaccinia. In both cases, sera were taken 30 days after a Dryvax® immunization. A primary response is characterized by modest titers of anti-H3L antibodies. In individuals vaccinated during the eradication campaign of the 1970's, detectable levels of anti-H3L antibodies remain for many years after the primary response (FIG. 1B). An anamnestic response is observed after boosting (FIGS. 1A-D). Anti-H3L antibodies are heavily represented in VIG (FIG. 1B). Neutralization titers ($PRNT_{50}$): #10 pre=<10; #10 post=2000; #8 pre=40; #8 post=3000; VIG>15,000 (FIG. 1B). In both immunoblots and arrays, sera were used at 1/50 dilution whereas VIG used at 1/500 (FIG. 1B).

The data indicate that the arrays are in agreement with immunoblot analysis in which an antibody response to H3L is seen in the majority of human vaccines, and which undergoes a strong anamnestic response after boosting (FIG. 1C). The location of vaccinia H3L among the *E. coli* bands is determined by anti-histidine tag antibody ('His') (FIG. 1C).

Example 3

This example shows that human antibodies against H3L neutralize vaccinia virus.

H3L was a known target of human antibody responses from Western blot studies (Crotty et al., *J Immunol* 171:4969 (2003), Demkowicz et al., *J Virol* 66:386 (1992)). The proteomic studies herein show that H3L is an immunodominant target of human anti vaccinia virus antibody responses. To determine whether the human anti-H3L is valuable for protection against poxvirus infections, affinity purified human anti-H3L Ig was studied in vitro for neutralization activity.

TABLE 1

Immunoreactive proteins identified by serological screening of arrays.

| Antigen | PI | Mol. Wt. | Description | TM Domain/ Sig. Peptide |
|---|---|---|---|---|
| *Reactive in Immunized Mice, Humans & Macaques* | | | | |
| 1 A10L | 6.33 | 102,283 | major core protein | No/No |
| 2 A11R | 4.81 | 36,134 | hypothetical protein | Yes/No |
| 3 A13L | 9.96 | 7.696 | IMV membrane protein | Yes/Yes |
| 4 A33R | 5.3 | 20,506 | EEV glycoprotein | Yes/Yes |
| 5 A56R | 4.05 | 34,778 | IEV, CEV/EEV hemagglutinin | Yes/Yes |
| 6 D8L | 9.55 | 35,326 | IMV chondroitin sulfate-binding protein | Yes/No |
| 7 D13L | 5.10 | 61,890 | Virion assembly protein | No/No |
| 8 F13L | 6.98 | 41,823 | IEV, CEV/EEV major envelope protein | No/No |
| 9 H3L | 6.43 | 37,458 | IMV heparan sulfate receptor | Yes/No |
| 10 H5R | 7.55 | 22,270 | late transcription factor | No/No |
| *Reactive in Immunized Humans & Macaques* | | | | |
| 1 A26L | 9.40 | 37,319 | A-type inclusion protein | No/No |
| *Reactive in Immunized Humans & Mice* | | | | |
| 1 A27L | 5.14 | 12,616 | IMV cell fusion protein | No/No |
| 2 MR | 6.13 | 28,460 | DNA-binding core protein | No/No |
| *Reactive in Immunized Mice & Macaques* | | | | |
| 1 B5R | 4.54 | 35,108 | IEV, CEV/EEV plaque-size/host range protein | Yes/Yes |
| 2 H7R | 7.27 | 16,912 | hypothetical protein | No/No |
| *Reactive in Immunized Macaques Only* | | | | |
| 1 A17L | 4.28 | 22,999 | IMV membrane protein | Yes/Yes |
| *Reactive in Immunized Mice Only* | | | | |
| 1 A3L | 6.75 | 72,624 | major core protein | No/No |
| 2 A4L | 4.68 | 30,846 | Memb. associated core protein | No/No |
| 3 D11L | 9.13 | 72,366 | DNA helicase | No/No |
| 4 E3L | 5.04 | 21,504 | Adenosine deaminase | No/No |
| 5 H6R | 10.30 | 36,665 | topoisomerase | No/No |
| 6 K2L | 9.73 | 42,299 | serine protease inhibitor | No/Yes |
| 7 N1L | 4.41 | 13,961 | hypothetical proteins | No/No |

On the basis of its dominance among the responses by humans and other species (Table 1), and its surface location on the virus where it would be accessible to neutralizing antibodies, the role of anti-H3L antibodies in protective immunity was evaluated.

VIG recognizes at least 13 specific antigens on the VV proteome microarray (Davies et al., *Proc Natl Acad Sci USA* 102:547 (2005)), including H3L (FIG. 1B, D), and VIG is available in high concentration. VIG was a source of human anti-H3L antibodies. Anti-H3L was affinity purified from VIG by panning over nitrocellulose bound H3L protein, and then eluting the anti-H3L Ig by low pH wash (as previously described). Each batch of affinity purified anti-H3L was of high purity, as verified by immunoblotting against whole vaccinia particles (FIG. 2A). The purified immunoglobulin concentration was determined by Bradford prior to use.

Affinity purified human anti-H3L was studied for activity by VV plaque reduction neutralization test ($PRNT_{50}$) (FIG. 2E). Human anti-H3L exhibited substantial neutralization activity against VV in vitro, with a top $PRNT_{50}$ of 44 μg/ml (FIG. 2E). Statistical analysis of three independent virus neutralization studies revealed a high level of statistical significance ($P<0.0001$).

In reciprocal studies, anti-H3L antibodies were depleted from human VIG or VV-immunized human serum (FIG. 2A). When depleted of anti-H3L antibodies using recombinant protein (FIG. 2A, B) VIG exhibits a 65% reduction of neutralization titer (50-80% reductions are normally seen in $PRNT_{50}$) (FIG. 2B). Therefore, H3L is the target of neutralizing antibodies in humans vaccinated against smallpox. Neutralization was not completely abolished after depletion of anti-H3L antibodies, presumably due to the spectrum of other antigens recognized by VIG that contribute to its overall neutralizing activity.

Figure 2:
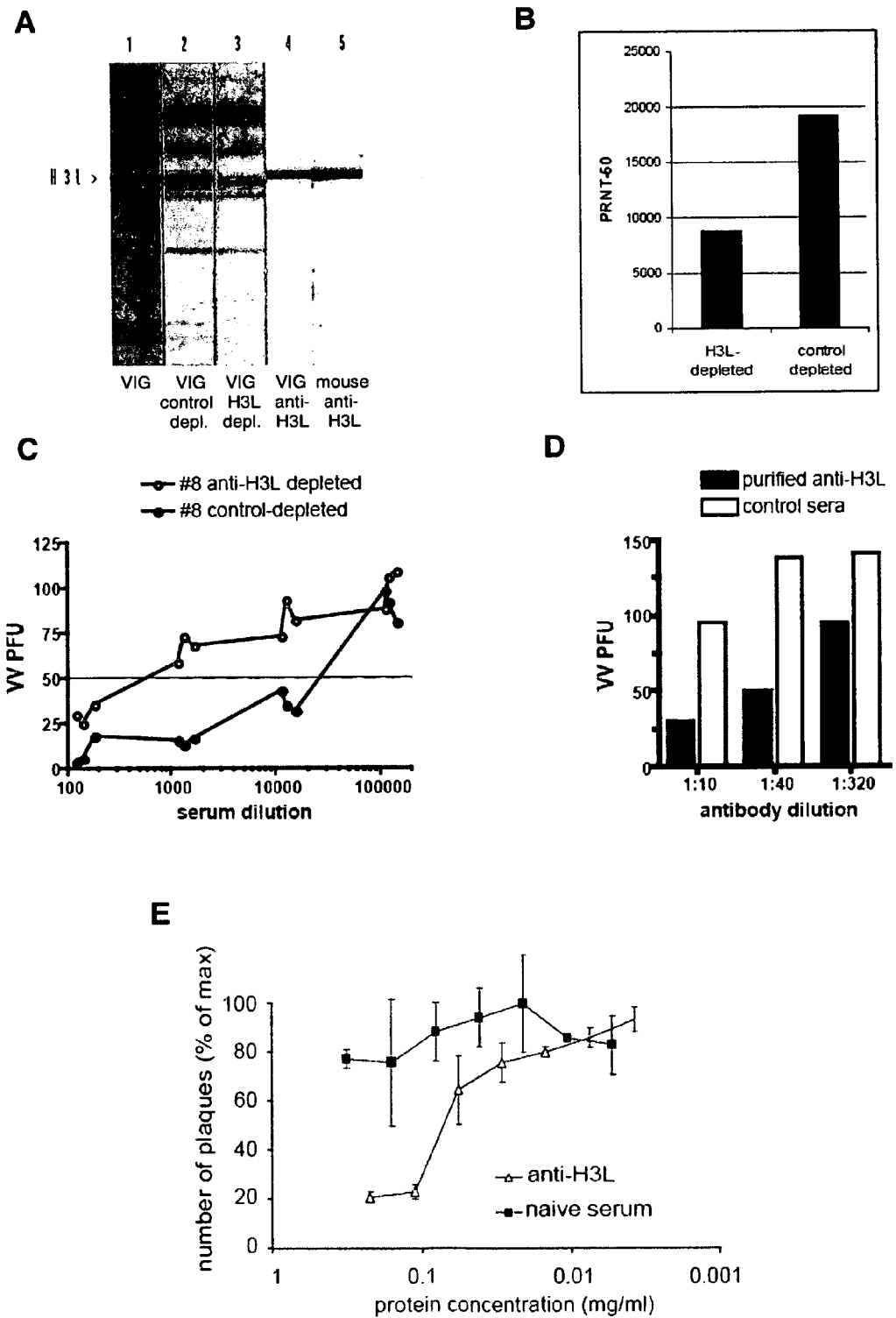
FIGS. 2A-2E show data indicating that Human antibodies against H3L are neutralizing. (A) Immunoblots of whole vaccinia virus particles probed with: lane 1. VIG; lane 2: VIG control-depleted against immobilized proteins from *E. coli* transformed with empty expression plasmid; lane 3: VIG depleted against H3L protein immobilized on Ni-NTA columns; lane 4: anti-H3L antibodies affinity purified from VIG; lane 5: anti-H3L antibody generated in mouse against recombinant protein. (B) Plaque reduction neutralization titers in anti-H3L depleted and control-depleted VIG. (C) Plaque reduction neutralization titers in anti-H3L depleted and control-depleted serum from volunteer #8. (D) Human anti-H3L antibodies neutralize vaccinia virus in vitro. (E) Plaque neutralization assays of mono-specific human anti-H3L antibodies affinity purified from VIG.

FIG. 2 also shows data from vaccinated donor #8 who has a focused profile of antibodies typical of a secondary response. Here, depletion of anti-H3L antibodies caused a 33-fold change in $PRNT_{50}$ (FIG. 2C).

The results of these data indicate that anti-H3L antibodies are an important component of the overall neutralization response to vaccinia, and H3L responses are dominant in the immunological memory to vaccinia. In addition, human anti-H3L IgG neutralizes vaccinia (FIG. 2D). Anti-H3L antibodies in VIG were affinity purified with nitrocellulose immobilized H3L protein (FIG. 2A). Purified anti-H3L IgG recognized virally produced H3L antigen by immunoblot (FIG. 2A) and neutralized vaccinia in vitro (FIG. 2D). The control antibody was provided by naïve human serum, containing higher total IgG concentrations.

These data indicate anti-H3L antibodies are a major component of the human neutralizing antibody response to vaccinia virus.

Example 4

This example shows that mice immunized against H3L develop protective neutralizing antibodies.

Pre-immune serum from mice has no nonspecific reactivities as is seen with naïve human serum. Anti-H3L antibodies neutralize vaccinia virus by generating H3L-specific serum against recombinant H3L protein in mice.

Figure 3:
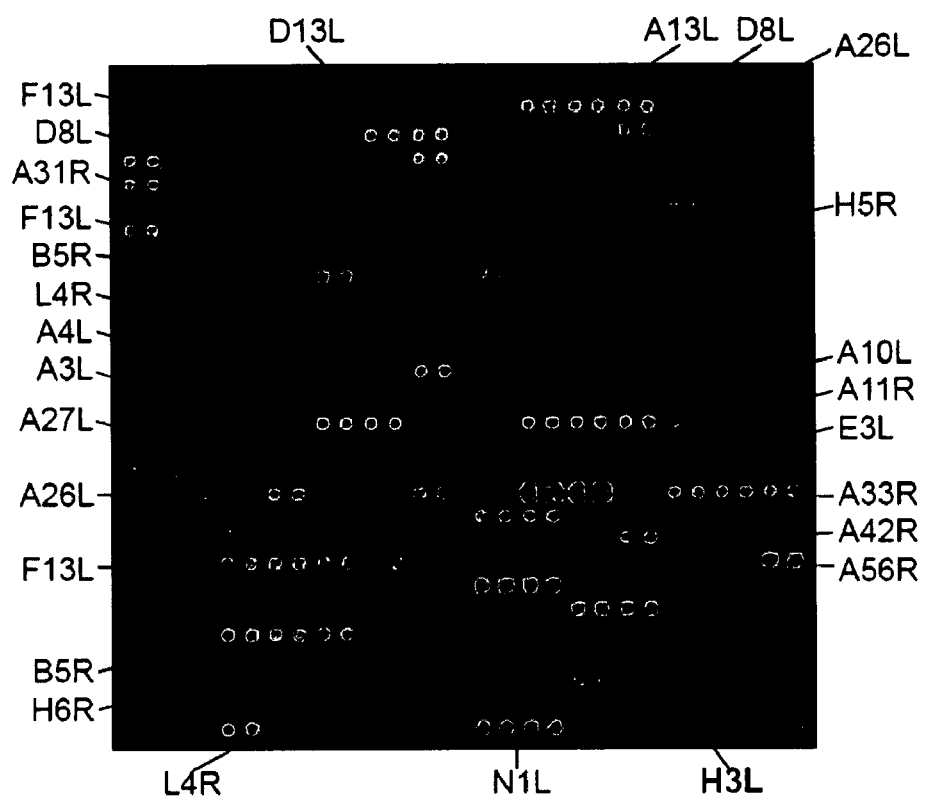
FIGS. 3A-3G show data indicating that Mice immunized with vaccinia develop an immunodominant anti-H3L response. (A) Array scan of a vaccinia virus proteome microarray probed with sera from representative BALB/c. (B). Array scan of serum from mouse immunized with recombinant H3L adjuvanted in Ribi. (C) Quantification of arrays stained with sera from 6 individual mice immunized 21 days previously with $VV_{WR}$. (D) Immunization schematic. (E) Representative immunoblot of serum from a single mouse immunized against recombinant H3L protein (left lane) probed against whole vaccinia virus particles (see FIG. 2A). Right lane shows affinity purified human anti-H3L to localize H3L band. (F) Anti-VV IgG in H3L immunized mice was quantified by ELISA. (G) Anti-VV neutralizing antibody titers ($PRNT_{50}$) were measured in H3L immunized mice and mice immunized with $VV_{NYBOH}$. Mean neutralizing antibody titers in H3L immunized mice were $PRNT_{50}$=3760. Mean neutralizing antibody titers in $1\times10^5$ PFU $VV_{NYBOH}$ immunized mice were $PRNT_{50}$=172.

Mouse antibodies generated against recombinant protein recognize H3L in chip ELISAs (FIG. 3B), as well as authentic H3L from vaccinia virions in both immunoblots (FIG. 3E) and ELISAs (FIG. 3F). Murine anti-H3L antibodies have strong VV neutralizing activity in vitro (FIG. 3G). H3L is also an immunodominant target of antibody responses after infection of mice with vaccinia virus (strain WR) (FIG. 3A). Mouse were immunized intraperitoneally 21 days before with vaccinia virus strain WR. The identity of the antigens has been reported (Davis et al., Proc Natl Acad Sci USA 102:547 (2005). No variation between the profiles of recognized antigens was seen between individual mice. See Table 1 for description of these antigens.

Mice were immunized with VV and serum was analyzed by VV proteome array staining (FIG. 3A). Some 21 different antigens were recognized by murine serum after VV immunization, including a strong antibody response to H3L (FIG. 3A). Quantification of signal intensities of the immunoreactive antigens for six different BALB/c mice (FIG. 3C). Underlined proteins are known envelope proteins. The horizontal line is a stringent cut-off, defined as the mean control signals plus 3×SD. The anti-H3L response was the strongest VV surface antigen detected (FIG. 1, and Davis et al., Proc Natl Acad Sci USA 102:547 (2005)). The immunodominance of the anti-H3L antibody response in humans and mice indicate that H3L is a highly immunogenic protein.

Mice were immunized twice with H3L protein in adjuvant, with the immunizations spaced three weeks apart. (FIG. 3D). Control groups of mice received injections of adjuvant alone, or no injections, or a single intraperitoneally immunization with $1 \times 10^5$ PFU $VV_{NYBOH}$. Mice were monitored for anti-H3L responses at multiple time points post-immunization. Serum from the immunized mice specifically recognized H3L in the VV proteome arrays (FIG. 3B). In addition, the antiserum recognized authentic H3L from vaccinia virions in both immunoblots (FIG. 3E) and ELISAs (FIG. 3F), and was demonstrated to be IgG by ELISA. Serum from H3L immunized mice was studied by standard $PRNT_{50}$ assay. Anti-VV IgG levels were significantly above baseline after primary ($P<0.01$, endpoint titer=1366) and secondary immunization ($P<0.001$, endpoint titer=$1.27 \times 10^6$) with H3L. Strong VV neutralizing activity was detected in the murine anti-H3L serum (FIG. 3G). H3L protein immunized mice possessed substantially higher neutralizing antibody levels than $VV_{NYBOH}$ immunized mice, demonstrating the potency of H3L as an antigenic target (FIG. 3G). In summary, there were strong similarities between the immunodominance and neutralizing activity of anti-H3L Ig both in VV-immunized humans and mice.

H3L was evaluated for its capacity to protect mice in the well-characterized $VV_{WR}$ intranasal challenge model system, in which unimmunized mice develop pneumonia and exhibit rapid weight loss and death within 7-9 days (Alcami et al., Cell 71:153 (1992), Belyakov et al., Proc Natl Acad Sci USA 100:9458 (2003), Fogg et al., J Virol 78:10230 (2004), Ramirez et al., J Gen Virol 83:1059 (2002), Reading et al., J Gen Virol 84:1973 (2003), Zhang et al., J Virol 74:11654 (2000)). Immunization of mice intraperitoneally with $VV_{NYBOH}$ or $VV_{WR}$ engenders full protective immunity against a subsequent intranasal challenge of virus (FIG. 4, and refs (Belyakov et al., Proc Natl Acad Sci USA 100:9458 (2003), Fogg et al., J Virol 78:10230 (2004), Xu et al., J Immunol 172:6265 (2004)).

Mice were immunized twice with purified H3L protein in adjuvant (FIG. 4A). Anti-H3L IgG responses were tracked by $PRNT_{50}$, chip ELISA, and traditional ELISA. Mice were then challenged with 1 $LD_{50}$ of $VV_{WR}$(FIG. 4A). Control groups of mice received injections of adjuvant alone, were immunized with the human smallpox vaccine ($VV_{NY}$), or nothing (unimmunized).

Approximately 50% of the unimmunized mice died from the intranasal $VV_{WR}$ infection. In contrast, all of H3L immunized mice survived infection ($P<0.02$) (FIG. 4C). H3L immunized mice also exhibited significantly less weight loss ($P<0.01$) than unimmunized (Groups A and D) control mice (FIG. 4B). No difference was observed between Group A and D. Group A and D combined as "unimmunized", N=12. $VV_{NYBOH}$, N=4. H3L, N=4.

A second group of mice were challenged with 50 $LD_{50}$ of $VV_{WR}$, and the H3L-immunized mice were not protected against that high challenge dose ($VV_{NYBOH}$ immunized mice were still protected against 50 $LD_{50}$). In a separate study, an older group of H3L immunized mice were challenged with $1 \times 10^5$ PFU $VV_{WR}$, and those mice exhibited substantial protection from death compared to unimmunized mice (4/5H3L, 1/7 unimmunized. $P<0.02$). In addition, morbidity and weight loss was much less severe in the H3L immunized cohort ($P<0.01$) (FIG. 4D).

The results indicate anti-H3L neutralizing antibodies can provide in vivo protection against pathogenic infection with $VV_{WR}$.

Example 5

This example shows that passive transfer of H3L neutralizing antibodies protects against intranasal VV challenge.

Figure 5:
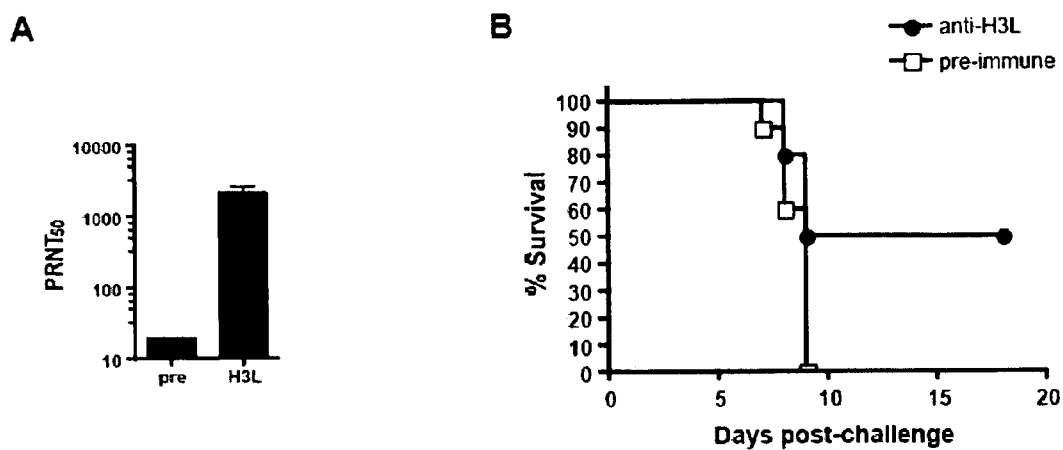
FIGS. 5A-5B show data indicating that Passive immunization with anti-H3L neutralizing antibodies provides partial protection from a lethal $VV_{WR}$ challenge. (A) VV neutralization activity of rabbit anti-H3L serum. (B) Survival curve after 3 $LD_{50}$ $VV_{WR}$ intranasal challenge. Black circles=anti-H3L passive transfer; Open squares=pre-immune passive transfer. 10 mice per group.

A sufficient quantity of anti-H3L immunoglobulin for passive transfer was produced by immunizing rabbits with H3L protein and subsequently collecting the anti-H3L rabbit serum. The rabbit anti-H3L serum was H3L specific by proteome array, and was shown to be neutralizing by $PRNT_{50}$ (FIG. 5A).

Polyclonal anti-H3L antiserum was injected intraperitoneally (2001) into BALB/c mice one day prior to intranasal challenge with 3 $LD_{50}$ of $VV_{WR}$. All of the mice receiving irrelevant serum (pre-immune) died. In contrast, mice receiving passive immunotherapy with anti-H3L antibodies protected 50% of mice (0/10 vs. 5/10 survival. $P<0.02$) (FIG. 5B).

In a repeat passive transfer study, anti-H3L antiserum provided significant protection against morbidity and mortality was observed against a 1 $LD_{50}$ challenge ($P<0.03$), but not a 3 $LD_{50}$ challenge. The partial protective efficacy in these studies likely relates to the limited neutralization capacity of the volume of passively transferred anti-H3L serum once it was diluted throughout the mouse, as it would be a lower titer than in a mouse directly immunized with H3L protein (FIGS. 3B and 3D-G). Consequently, better protection is likely to be achieved with more anti-H3L antibody. In summary, anti-H3L neutralizing antibodies provide protection against a lethal infection with a pathogenic poxvirus.

What is claimed is:

1. A method for providing a subject with protection against poxvirus infection or pathogenesis, comprising administering a composition comprising a sufficient amount of an antibody that binds to H3L envelope protein or an H3L envelope protein homolog to provide the subject with protection against poxvirus infection or pathogenesis, wherein the composition administered excludes an antibody that binds to vaccinia protein A33R or A33R homolog and excludes an antibody that binds to vaccinia protein L1R or L1R homolog.

2. A method for protecting a subject from poxvirus infection or pathogenesis, comprising administering a composition comprising a sufficient amount of antibody that binds to H3L envelope protein or an H3L envelope protein homolog to the subject, wherein the composition administered excludes an antibody that binds to vaccinia protein A33R or A33R homolog and excludes an antibody that binds to vaccinia protein L1R or L1R homolog, and wherein the composition is administered concurrently with or following a poxvirus infection, contact with or exposure to a poxvirus, or vaccination with a poxvirus.

3. A method for decreasing susceptibility of a subject to a poxvirus infection or pathogenesis, comprising administering a composition comprising a sufficient amount of an antibody that binds to H3L envelope protein or an H3L envelope protein homolog to decrease susceptibility of the subject to poxvirus infection or pathogenesis, wherein the composition administered excludes an antibody that binds to vaccinia protein A33R or A33R homolog and excludes an antibody that binds to vaccinia protein L1R or L1R homolog.

4. The method of claim 3, wherein the poxvirus comprises a pathogenic poxvirus.

5. The method of claim 4, wherein the pathogenic poxvirus is selected from variola major and variola minor smallpox virus.

6. The method of claim 4, wherein the pathogenic poxvirus is selected from monkeypox, cowpox, Molluscum Contagiosum, vaccinia virus and camelpox virus.

7. The method of any of claims 1 to 3, wherein the composition further comprises vaccinia B5R or A27L poxvirus protein or a B5R or A27L poxvirus protein homolog.

8. The method of claim 7, wherein the poxvirus protein is present on one or more IMV, CEV or EEV forms of smallpox.

9. The method of claim 7, wherein the poxvirus protein does not consist of a live or attenuated vaccinia virus.

10. The method of claim 7, wherein the poxvirus protein does not consist of live or attenuated poxvirus.

11. The method of claim 7, wherein the poxvirus protein does not consist of modified vaccinia Ankara (MVA), vaccinia virus Lister strain, vaccinia virus LC16m8 strain, vaccinia virus NYCBOH strain, or vaccinia virus Wyeth strain.

12. The method of any of claims 1 to 3, further comprising administering vaccinia B5R or A27L poxvirus protein or a B5R or A27L poxvirus protein homolog.

13. The method of claim 12, wherein the poxvirus protein is present on one or more IMV, CEV or EEV forms of smallpox.

14. The method of claim 12, wherein the poxvirus protein does not consist of live or attenuated vaccinia virus.

15. The method of claim 12, wherein the poxvirus protein does not consist of live or attenuated poxvirus.

16. The method of claim 12, wherein the poxvirus protein does not consist of modified vaccinia Ankara (MVA), vaccinia virus Lister strain, vaccinia virus LC16m8 strain, vaccinia virus NYCBOH strain, or vaccinia virus Wyeth strain.

17. The method of any of claims 1 to 3, further comprising administering an additional antibody that binds to a vaccinia B5R or A27L poxvirus protein or a B5R or A27L poxvirus protein homolog.

18. The method of claim 17, wherein the additional antibody that binds to a vaccinia B5R or A27L poxvirus protein or a B5R or A27L poxvirus protein homolog present on one or more IMV, CEV or EEV forms of smallpox.

19. The method of claim 17, wherein the additional antibody is not an antibody that binds to vaccinia protein D8L, A17L, L5, A21, H2, A28, A14, A56, A34, A36, A2, or a D8L, A17L, L5, A21, H2, A28, A14, A56, A34, A36, or A2 homolog.

20. The method of claim 17, wherein the additional antibody is not vaccinia immune globulin (VIG).

21. The method of any of claims 1 to 3, wherein the composition further comprises an additional antibody that binds to a vaccinia B5R or A27L poxvirus protein or a B5R or A27L poxvirus protein homolog.

22. The method of claim 21, wherein the additional antibody that binds to a vaccinia B5R or A27L poxvirus protein or a B5R or A27L poxvirus protein homolog is present on one or more IMV, CEV or EEV forms of smallpox.

23. The method of any of claims 1 to 3, wherein the composition excludes an antibody that binds to vaccinia protein B5R, D8L, A27L, A17L, L5, A21, H2, A28, A14, A56, A34, A36, A2, or a B5R, D8L, A27L, A17L, L5, A21, H2, A28, A14, A56, A34, A36, or A2 homolog.

24. The method of any of claims 1 to 3, wherein said antibody that binds to H3L envelope protein does not consist of human whole vaccinia immunoglobulin (VIG).

25. The method of claims 1 or 3, wherein the composition is administered prior to, or concurrently with a poxvirus infection, contact with or exposure to a poxvirus, or vaccination with a poxvirus.

26. The method of claim 25, wherein the poxvirus is selected from variola major or variola minor smallpox virus.

27. The method of claim 25, wherein the poxvirus is selected from monkeypox, cowpox, Molluscum Contagiosum and camelpox.

28. The method of any of claims 1 to 3, wherein the method provides partial or complete protection against poxvirus infection or pathogenesis, or a symptom of poxvirus infection or pathogenesis.

29. The method of claim 28, wherein the poxvirus is selected from variola major or variola minor smallpox virus.

30. The method of claim 28, wherein the poxvirus is selected from monkeypox, cowpox, Molluscum Contagiosum and camelpox.

31. The method of any of claims 1 to 3, wherein the method reduces, decreases, inhibits, or ameliorates onset, progression, severity, duration, frequency or probability of one or more symptoms associated with a poxvirus infection or pathogenesis.

32. The method of claim 31, wherein the poxvirus is selected from variola major and variola minor smallpox virus.

33. The method of claim 31, wherein the poxvirus is selected from monkeypox, cowpox, Molluscum Contagiosum and camelpox.

34. The method of claim 31, wherein the symptom is selected from: high fever, fatigue, headache, backache, malaise, rash or lesions, delirium, vomiting, diarrhea, or excess bleeding.

35. The method of any of claims 1 to 3, wherein the antibody is human, humanized or chimeric.

36. The method of any of claims 1 to 3, wherein the antibody is monoclonal or polyclonal.

37. The method of any of claims 1 to 3, wherein the antibody is an antibody subsequence that binds to H3L envelope protein.

38. A method for providing a subject with protection against poxvirus infection or pathogenesis, comprising administering a composition comprising a sufficient amount of an antibody to provide the subject with protection against poxvirus infection or pathogenesis, wherein the antibody binds to H3L envelope protein or an H3L envelope protein homolog and is not an antibody that binds to vaccinia protein B5R, L1R, D8L, A33R, A27L, A17L, L5, A21, H2, A28, A14, A56, A34, A36, A2, or a B5R, L1R, D8L, A33R, A27L, A17L, L5, A21, H2, A28, A14, A56, A34, A36, or A2 homolog.

39. A method for protecting a subject from poxvirus infection or pathogenesis, comprising administering a composition comprising a sufficient amount of an antibody to protect the subject from poxvirus infection or pathogenesis, wherein the antibody binds to H3L envelope protein or an H3L envelope protein homolog and is not an antibody that binds to vaccinia protein B5R, L1R, D8L, A33R, A27L, A17L, L5, A21, H2, A28, A14, A56, A34, A36, A2, or a B5R, L1R, D8L, A33R, A27L, A17L, L5, A21, H2, A28, A14, A56, A34, A36, or A2 homolog, and wherein the composition is administered concurrently with or following a poxvirus infection, contact with or exposure to a poxvirus, or vaccination with a poxvirus.

40. A method for decreasing susceptibility of a subject to a poxvirus infection or pathogenesis, comprising administering a composition comprising a sufficient amount of an antibody to decrease susceptibility of the subject to poxvirus infection or pathogenesis, wherein the antibody binds to H3L envelope protein or an H3L envelope protein homolog and is not an antibody that binds to vaccinia protein B5R, L1R, D8L, A33R, A27L, A17L, L5, A21, H2, A28, A14, A56, A34, A36, A2, or a B5R, L1R, D8L, A33R, A27L, A17L, L5, A21, H2, A28, A14, A56, A34, A36, or A2 homolog.

41. The method of any of claims 38 to 40, wherein the poxvirus comprises a pathogenic poxvirus.

42. The method of claim 41, wherein the pathogenic poxvirus is selected from variola major and variola minor smallpox virus.

43. The method of claim 41, wherein the pathogenic poxvirus is selected from monkeypox, cowpox, Molluscum Contagiosum, vaccinia virus and camelpox virus.

44. The method of any of claims 38 to 40, further comprising administering vaccinia B5R or A27L poxvirus protein or a B5R or A27L poxvirus protein homolog.

45. The method of claim 44, wherein the additional poxvirus protein is present on one or more IMV, CEV or EEV forms of smallpox.

46. The method of claims 38 or 40, wherein the composition is administered prior to, or concurrently with, poxvirus infection, contact with or exposure to a poxvirus, or vaccination with a poxvirus.

47. The method of claim 46, wherein the poxvirus is selected from variola major or variola minor smallpox virus.

48. The method of claim 46, wherein the poxvirus is selected from monkeypox, cowpox, Molluscum Contagiosum and camelpox.

49. The method of any of claims 38 to 40, wherein the method reduces, decreases, inhibits, or ameliorates onset, progression, severity, duration, frequency or probability of one or more symptoms associated with a poxvirus infection or pathogenesis.

50. The method of claim 49, wherein the symptom is selected from: high fever, fatigue, headache, backache, malaise, rash or lesions, delirium, vomiting, diarrhea, or excess bleeding.

51. The method of any of claims 38 to 40, wherein the antibody that binds to H3L envelope protein or an H3L envelope protein homolog is human, humanized or chimeric.

52. The method of any of claims 38 to 40, wherein the antibody that binds to H3L envelope protein or an H3L envelope protein homolog is monoclonal or polyclonal.

53. The method of any of claims 38 to 40, wherein the antibody that binds to H3L envelope protein or an H3L envelope protein homolog is an antibody subsequence.

54. A method for providing a subject with protection against poxvirus infection or pathogenesis, comprising administering a composition comprising a sufficient amount of an antibody to provide the subject with protection against poxvirus infection or pathogenesis, wherein the antibody is a first antibody that binds to H3L envelope protein or an H3L envelope protein homolog and a second antibody that binds to B5R protein or B5R protein homolog, and wherein the antibody is not an antibody that binds to vaccinia protein L1R, D8L, A33R, A27L, A17L, L5, A21, H2, A28, A14, A56, A34, A36, A2, or a L1R, D8L, A33R, A27L, A17L, L5, A21, H2, A28, A14, A56, A34, A36, or A2 homolog.

55. A method for protecting a subject from poxvirus infection or pathogenesis, comprising administering a composition comprising a sufficient amount of antibody to protect the subject from poxvirus infection or pathogenesis, wherein the antibody is a first antibody that binds to H3L envelope protein or an H3L envelope protein homolog and a second antibody that binds to B5R protein or B5R protein homolog, and wherein the antibody is not an antibody that binds to vaccinia protein L1R, D8L, A33R, A27L, A17L, L5, A21, H2, A28, A14, A56, A34, A36, A2, or a L1R, D8L, A33R, A27L, A17L, L5, A21, H2, A28, A14, A56, A34, A36, or A2 homolog.

56. A method for decreasing susceptibility of a subject to a poxvirus infection or pathogenesis, comprising administering a composition comprising a sufficient amount of antibody to decrease susceptibility of the subject to poxvirus infection or pathogenesis, wherein the antibody is a first antibody that binds to H3L envelope protein or an H3L envelope protein homolog and a second antibody that binds to B5R protein or B5R protein homolog, and wherein the antibody is not an antibody that binds to vaccinia protein L1R, D8L, A33R, A27L, A17L, L5, A21, H2, A28, A14, A56, A34, A36, A2, or a L1R, D8L, A33R, A27L, A17L, L5, A21, H2, A28, A14, A56, A34, A36, or A2 homolog.

57. The method of any of claims 54 to 56, wherein the poxvirus comprises a pathogenic poxvirus.

58. The method of claim 57, wherein the pathogenic poxvirus is selected from variola major and variola minor smallpox virus.

59. The method of claim 57, wherein the pathogenic poxvirus is selected from monkeypox, cowpox, Molluscum Contagiosum, vaccinia virus and camelpox virus.

60. The method of any of claims 54 to 56, further comprising administering vaccinia B5R or A27L poxvirus protein or a B5R or A27L poxvirus protein homolog.

61. The method of claim 60, wherein the vaccinia B5R or A27L poxvirus protein or B5R or A27L poxvirus protein homolog is present on one or more IMV, CEV or EEV forms of smallpox.

62. The method of any of claims 54 to 56, wherein the composition is administered prior to, concurrently with, or following poxvirus infection, contact with or exposure to a poxvirus, or vaccination with a poxvirus.

63. The method of claim 62, wherein the poxvirus is selected from variola major or variola minor smallpox virus.

64. The method of claim 63, wherein the poxvirus is selected from monkeypox, cowpox, Molluscum Contagiosum and camelpox.

65. The method of any of claims 54 to 56, wherein the method reduces, decreases, inhibits, or ameliorates onset, progression, severity, duration, frequency or probability of one or more symptoms associated with a poxvirus infection or pathogenesis.

66. The method of claim 65, wherein the symptom is selected from: high fever, fatigue, headache, backache, malaise, rash or lesions, delirium, vomiting, diarrhea, or excess bleeding.

67. The method of any of claims 54 to 56, wherein the first or second antibody is human, humanized or chimeric.

68. The method of any of claims 54 to 56, wherein the first or second antibody is monoclonal or polyclonal.

69. The method of any of claims 64 to 56, wherein the first or second antibody is an antibody subsequence.

* * * * *

UNITED STATES PATENT AND TRADEMARK OFFICE
CERTIFICATE OF CORRECTION

Page 1 of 1

PATENT NO. : 7,393,533 B1
APPLICATION NO. : 11/269054
DATED : July 1, 2008
INVENTOR(S) : Shane Crotty, Philip L. Felgner and David Huw Davies It is certified that error appears in the above-identified patent and that said Letters Patent is hereby corrected as shown below:

In the Specification

Col. 1, lines 14-17:
replace "Work described herein was supported in part by grants U01AI056464 and AI058365, awarded by the National Institutes of Health. The United States Government may have certain rights in this invention."
with --This invention was made with government support under Grants U01AI056464 and AI058365 awarded by the National Institutes of Health. The government has certain rights in the invention.--

Signed and Sealed this
Eighth Day of October, 2013

Teresa Stanek Rea
*Deputy Director of the United States Patent and Trademark Office*